US006927214B1

(12) United States Patent
Teng et al.

(10) Patent No.: US 6,927,214 B1
(45) Date of Patent: Aug. 9, 2005

(54) NON-PEPTIDE GLP-1 AGONISTS

(75) Inventors: Min Teng, San Diego, CA (US); Larry Kenneth Truesdale, San Diego, CA (US); Dilip Bhumralkar, San Diego, CA (US); Dan Kiel, San Diego, CA (US); Michael D. Johnson, San Diego, CA (US); Christine Thomas, San Diego, CA (US); Anker Steen Jorgensen, Copenhagen (DK); Peter Madsen, Bagsvaerd (DK); Preben Houlberg Olesen, Copenhagen (DK); Liselotte Bjerre Knudsen, Valby (DK); Ingrid Vivika Petterson, Frederiksberg (DK); Johannes Cornelis de Jong, Bagsvaerd (DK); Carsten Behrens, Copenhagen (DK); Janos Tibor Kodra, Copenhagen (DK); Jesper Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/483,504

(22) Filed: Jan. 14, 2000

Related U.S. Application Data

(60) Provisional application No. 60/116,116, filed on Jan. 15, 1999.

(30) Foreign Application Priority Data

Jan. 15, 1999 (DK) .................................. PA 1999 00041

(51) Int. Cl.$^7$ ...................... A61K 31/33; A61K 31/495; C07D 239/00; C07D 241/36
(52) U.S. Cl. ........................ 514/183; 514/249; 544/335; 544/349; 544/353; 544/354; 544/355; 544/356
(58) Field of Search ................................ 514/183, 249; 544/335, 349, 353, 354, 355, 356

(56) References Cited

U.S. PATENT DOCUMENTS

| | | | |
|---|---|---|---|
| 4,022,777 A | * 5/1977 | Sam et al. ................... 544/345 |
| 4,200,748 A | 4/1980 | Wright, Jr. et al. ........... 544/99 |
| 4,349,674 A | 9/1982 | Freed, deceased et al. . 544/353 |
| 5,849,742 A | 12/1998 | App et al. ................... 514/249 |

FOREIGN PATENT DOCUMENTS

| | | |
|---|---|---|
| DE | 3 826 603 A1 | 2/1990 |
| EP | 0 018 493 A1 | 11/1980 |
| EP | 0 216 299 A1 | 4/1987 |
| EP | 0 277 794 A2 | 8/1988 |
| EP | 0 338 346 A2 | 10/1989 |
| FR | 1 469 360 | 1/1967 |
| GB | 966818 | 8/1964 |
| JP | 55167205 | * 12/1980 |
| WO | WO 87/06941 | 11/1987 |
| WO | WO 90/11296 | 10/1990 |
| WO | WO 91/11457 | 8/1991 |
| WO | WO 95/05378 | 2/1995 |
| WO | WO 95/24403 | 9/1995 |
| WO | WO 96/30370 | 10/1996 |
| WO | 9719934 | * 6/1997 |
| WO | WO 97/32858 | 9/1997 |
| WO | WO 98/20895 | 5/1998 |
| WO | WO 98/28414 | 7/1998 |
| WO | WO 98/52945 | 11/1998 |
| WO | WO 99/01423 | 1/1999 |
| WO | WO 99/01442 | 1/1999 |

OTHER PUBLICATIONS

Wozniak et al, Indian J. od Heterocyclic Chem. 4/2,75080(1994).*
Englehardt et al, DE 2433397,Feb, 1975, also cited as Chemical Abstract DN 82:156377.*
Page et al, ACS, Inorganic Chem. 37/17/4452–4459(1998).*
Chemical Abstract DN 122:314514, Wozniak et al, also cited as Indian J. Heterocyclic Chem. 4/2.75–80(1994).*
Chemical Abstract DN 103:37081 for CASRN 97183–62–5.*
Chemical Abstract DN 92:76440 for CASRN # 52312–40–0.*
Chemical Abstract DN117:192207 for CASRN# 143309087–9P.*
Chemical Abstract DN 75:129758 for CASRN # 33870–76–7P/7, 33870–77–8.*
Chemical Abstract DN 109:92044 for CASRN # 6640–47–7,90004–55–0P.*
Chemical AbstractDN 115:70795 for CASRN # 34972–22–0.*
Chemical Abstract DN 128:75375 for CASRN#6640–47–7, 200815–10–7P.*
Chemical Abstract DN 82:156377, also cited as Englehardt et al, DE 2433397, Feb. 1975.*
Chemical Abstract DN 129:224913, also cited as Page et.al, ACS, Inorganic Chem., 37/17/4452–4459(1998).*
Chemical Abstract DN 112:179028, also cited as JP 01261389, dated Oct. 1989.*
Chung et al, Chem. Commun. "Quinoxalino–fused sultines and their Application in Diels–Alder reactions" pp. 205–206 (1997).
J. J. Holst, Annu. Rev. Physiol., vol. 59, pp. 257–271 (1997).
Nauck et al., J. Clin. Invest., vol. 91, pp. 301–307 (1993).

(Continued)

Primary Examiner—Richard L. Raymond
Assistant Examiner—Sudhaker B. Patel
(74) Attorney, Agent, or Firm—Richard W. Book; Reza Green; Marc A. Began

(57) ABSTRACT

Novel non-peptide GLP-1 agonists, pharmaceutical compositions comprising them, use of the non-peptide GLP-1 agonists for the preparation of pharmaceutical compositions and methods for the treatment and/or prevention of disorders and diseases wherein an activation of the human GLP-1 receptor is beneficial, especially metabolic disorders such as IGT, Type 1 diabetes, Type 2 diabetes and obesity.

27 Claims, No Drawings

OTHER PUBLICATIONS

Qualmann et al., Acta Diabetol., vol. 32, pp. 13–16 (1995).
Nathan, M.D. et al., Diabetes Care, vol. 15, pp. 270–276 (1992).
Nauck et al., Diabetologia, vol. 36, pp. 741–744 (1993).
Kreymann et al., The Lancet, pp. 1300–1304, Dec. 5, 1987.
Rachman et al., Diabetologia, vol. 40, pp. 205–211 (1997).
Gutniak, M. D., Ph. D. et al., Diabetes Care, vol. 17, pp. 1039–1044 (1994).
Nauck et al., Diabetologia, vol. 39, pp. 1546–1553 (1996).
Creutzfeldt, M.D., F.R.C.P. et al., Diabetes Care, vol. 19, pp. 580–586 (1996).
Fehmann et al., Endocrinology, vol. 130, pp. 159–166 (1992).
Wang et al., Endocrinology, vol. 136, pp. 4910–4917 (1995).
Wang et al., The Journal of Clinical Investigation, vol. 99, pp. 2883–2889 (1997).
Edvell et al., Endocrinology, vol. 140, pp. 778–783 (1999).
Buteau et al., Diabetologia, vol. 42, pp. 856–864 (1999).
Xu et al., Diabetes, vol. 48, pp. 2270–2276 (1999).
Nauck et al., Diabetologia, vol. 29, pp. 46–52 (1986).
Holst et al., Diabetologia, vol. 40, pp. 984–986 (1997).
Flint et al., J. Clin. Invest., vol. 101, pp. 515–520 (1998).
Naslund et al., Drug News Perspect, vol. 11, pp. 92–97 (1998).
Ranganath et al., Gut, vol. 38, pp. 916–919 (1996).
Naslund et al., Digestive Diseases and Sciences, vol. 43, pp. 945–952 (1998).
Naslund et al., Am J Clin Nutr, vol. 68, pp. 525–530 (1998).
Deacon et al., Diabetes, vol. 44, pp. 1126–1131 (1995).
Knudsen et al., European Journal of Pharmacology, vol. 318, pp. 429–435 (1996).
Horn et al., Receptors and Channels, vol. 5, pp. 305–314 (1998).
Adelhorst et al., The Journal of Biological Chemistry, vol. 269, No. 9, pp. 6275–6278 (1994).
Mechanism et al., The Journal of Biological Chemistry, vol. 273, No. 29, pp. 17979–17982 (1998).
Willms et al., Journal of Clinical Endocrinology and Metabolism, vol. 81, No. 1, pp. 327–332 (1996).
Makino et al., Heterocycles, vol. 26, pp. 1215–1220 (1987).
Abstract of Iijima et al., Yakugaku Zasshi, vol. 108, No. 5, pp. 437–442 (1988).
Abstract of Cascieri et al., J. Biol. Chem., vol. 274, No. 13, pp. 8694–8697 (1999).
Abstract of O.S. Moustafa, Phosphorus, Sulfur Silicon Relat. Elem., vol. 131, pp. 49–57 (1997).
Abstract of Guillon et al., Pharm. Pharmacol. Commun., vol. 4, No. 7, pp., 319–324 (1998).
Abstract of Tomoda et al., Bull. Chem. Soc. Jpn., vol. 71, No. 5, pp. 1125–1135 (1998).
Abstract of Piras et al., Farmaco, vol. 48, pp. 1249–1259 (1993).
Abstract of Collins et al., Bioorg. Med. Chem. Lett., vol. 2, No. 9, pp. 915–918 (1992).
Abstract of Shinde et al., Indian Drugs, vol. 27, pp. 32–34 (1989).
Abstract of Iijima et al., Chem. Pharm. Bull., vol. 37, No. 3, pp. 618–620 (1989).
Abstract of Mahajanshetti et al., Indian J. Chem., vol. 12, No. 1, pp. 54–56 (1974).

\* cited by examiner

NON-PEPTIDE GLP-1 AGONISTS

This application is related to U.S. Provisional Application Ser. No. 60/116,116, filed Jan. 15, 1999, and claims the benefit of Denmark PA 199900041, filed Jan. 15, 1999.

FIELD OF THE INVENTION

The present invention relates to novel non-peptide GLP-1 agonists, pharmaceutical compositions comprising them, use of the non-peptide GLP-1 agonists for the preparation of pharmaceutical compositions and methods for the treatment and/or prevention of disorders and diseases wherein an activation of the human GLP-1 receptor is beneficial, especially metabolic disorders such as IGT (impaired glucose tolerance), Type 1 diabetes, Type 2 diabetes and obesity.

BACKGROUND OF THE INVENTION

GLP-1 (glucagon like peptide-1) is a 30 amino acid long peptide hormone secreted by the L-cells in the intestine.

GLP-1 consists of two native forms, GLP-1 (7-36) and GLP-1 (7-37), of the following amino acid sequences:

```
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36
Ile-Ala-Trp-Leu-Val-Lys-Gly-Arg-x
``` wherein X is $NH_2$ for GLP-1(7-36) and Gly for GLP-1(7-37).

GLP-1 is a so-called incretin and its primary mechanisms of actions are to:

Stimulate insulin secretion in a physiological and glucose-dependent manner

Decrease glucagon secretion

Inhibit gastric emptying

Decrease appetite

Stimulate growth/proliferation of β-cells.

Stimulating insulin secretion and at the same time decreasing glucagon secretion is probably what makes GLP-1 a very efficient blood glucose lowering agent (1). The very efficient blood glucose lowering as well as the glucose dependency of its action makes it an ideal candidate for the treatment of Type 2 diabetes (2–10). Furthermore, it may be useful for the treatment of Type 1 diabetes in combination with insulin (11). GLP-1 offers something that no other existing drug or drug candidate can provide: very efficient blood glucose lowering, even in SU (sulphonylurea)-failures (6), without the risk of serious hypoglycaemia. Apart from these major effects, GLP-1 has also been shown to increase the rate of insulin biosynthesis (12,13) and restore the ability of the β-cells to respond rapidly to rising plasma glucose in terms of first phase insulin release in rats (14). Thus, GLP-1 would be expected to be able to prevent or delay the progression from IGT to full blown Type 2 diabetes. Patients treated with GLP-1 compared to eg metformin or sulphonylureas, will be better managed and may as a result thereof have a much later transfer to insulin requiring therapy.

Recently, GLP-1 compounds have been shown to stimulate growth and proliferation of β-cells (15–17), thereby also supporting use of GLP-1 compounds and GLP-1 agonists for increasing the number of β-cells in a patient in vivo.

An important and perhaps primary defect in Type 2 diabetes patients may be an impaired incretin function (18,19). In fact, in the rather few patients with Type 2 diabetes so far investigated for this, all had a greatly decreased or absent insulin response to the "other" incretin hormone, namely GIP (Gastric Inhibitory Polypeptide) (19, 20). Because GIP is the "first-in-line" incretin and GIP signalling is defective, meal-induced insulin secretion is also defective. This cannot be overcome with endogenous or exogenous GIP because the patients are insensitive to GIP, but it may be compensated for with GLP-1 (20). In contrast to GIP, the insulinotropic action of GLP-1 is preserved in diabetic patients (21). Replacing the incretin deficiency may also be why GLP-1 treatment is so effective.

The ability of GLP-1 to decrease appetite and energy intake is now firmly established, both in normal, lean people and in obese people (22–24). Obese subjects have been shown to have an attenuated GLP-1 release in response to meals (25,26). This may further add to the potential of GLP-1 as being able to decrease weight in Type 2 diabetes patients. This use of GLP-1 is described further in WO No 98/20895 to Novo Nordisk A/S and WO No 98/28414 to Eli Lilly and Company.

GLP-1 is rapidly metabolised by the proteolytic enzyme Dipeptidyl Peptidase-IV (27) into an inactive or perhaps even antagonistic metabolite (28), complicating the use of GLP-1 as a drug.

The use of GLP-1 and analogues of GLP-1 as well as fragments thereof in the treatment of Type 1 and Type 2 diabetes and obesity are disclosed in several publications.

WO No 87/06941 and WO No 90/11296 to The General Hospital Corporation disclose GLP-1 fragments, including GLP-1(7-37) and GLP-1(7-36), and functional derivatives thereof for use as insulinotropic agents.

Furthermore, WO No 91/11457 to Buckley et al. discloses analogues of the active GLP-1 peptides 7-34, 7-35, 7-36, and 7-37 for use in the treatment of Type 2 diabetes and WO No 98/08871 to Novo Nordisk A/S discloses derivatives of GLP-1 for use in the treatment of diabetes and obesity which are especially useful as they are both metabolically stable and very potent.

However, peptides are generally not known to be orally available.

Best care for patients would obviously be achieved if a drug was orally available. The provision of orally available non-peptide GLP-1 agonists would therefore constitute a highly valuable contribution to the art.

The GLP-1 receptor is a so-called 7 transmembrane (7TM) G-protein coupled receptor. These receptors are transmembrane proteins consisting of a N-terminal extracellular part, a transmembrane core and three extracellular and three intracellular loops. The receptors are coupled to a G-protein (consisting of three subunits) and then further to an effector system. The effector system for the GLP-1 receptor is the adenylyl cyclase enzyme. Upon activation of the receptor, adenylyl cyclase catalyses the formation of the second messenger cAMP from ATP.

U.S. Pat. No. 5,670,360 to Novo Nordisk A/S discloses the cloning and use of the GLP-1 receptor. Five superfamilies of these receptors are known. Of these the glucagon-secretin (B) family consists of the receptors for GLP-1, glucagon, GIP, secretin, VIP, PACAP, calcitonin, PTH, CRF, GRF and a few more.

The (B) family is characterised by a relative large N-terminal domain of the receptor. The natural ligands for these receptors are all large peptides and the binding (and consecutive activation) of the receptors by their natural ligands is believed to involve both the N-terminal domain and the transmembrane region.

Small non-peptide agonists for peptide receptors are generally considered very difficult to find.

The above characteristics of the (B) family receptors seem to further complicate the provision of an agonist and so far no small non-peptide agonists have been described for a receptor in the (B) family.

However, surprisingly we have found a whole new class of non-peptide GLP-1 agonists which activate the human GLP-1 receptor.

They may be characterised by activating the human GLP-1 receptor without competing with GLP-1 for the GLP-1 binding site in a competition binding assay.

Furthermore, experiments have shown that the affinity of the receptor for GLP-1 changes upon incubation with some of the compounds according to the invention.

It is believed that the compounds of the invention stabilise another conformation of the receptor than that stabilised by GLP-1.

G-protein coupled receptors are theoretically thought to exist in different conformations: R and R*, where R is the inactive receptor conformation and R* the active. The most recent literature speculates that there may be one or more intermediate states (31).

One understanding of antagonists and inverse agonists is that they are able to bind to and stabilise the inactive conformation of the receptor whereas agonists bind to and stabilise the active conformation. It is not really known what a partial agonist does in these models.

The compounds according to the invention may introduce a new model in order to accommodate their characteristics. In this model we introduce a further receptor conformation R** which is another active receptor conformation.

R* would then be the conformation that GLP-1 under normal circumstances stabilises where R** is the conformation that the compounds according to the invention stabilises. A model with two different active receptor conformations may also offer an explanation for why some of the compounds according to the invention when tested in the assays are partial and not full agonists because one conformation may be able to elicit partial agonism only and the other full agonism.

Definitions

The following is a detailed definition of the terms used to describe the compounds of the invention:

"Halogen" designates an atom selected from the group consisting of F, Cl, Br or I.

The term "lower alkyl" in the present context designates a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "lower alkenyl" as used herein represents a branched or straight hydrocarbon group having from 2 to 6 carbon atoms and at least one double bond. Examples of such groups include, but are not limited to, vinyl, 1-propenyl, 2-propenyl, isopropenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "lower alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "lower alkanoyl" in the present context designates a group —C(O)—H or —C(O)-lower alkyl wherein lower alkyl has the above meaning. Representative examples include, but are not limited to, formyl, acetyl, propionyl, butyryl, valeryl, hexanoyl, heptanoyl and the like.

The term "cycloalkyl" as used herein represents a saturated carbocyclic group having from 3 to 10 carbon atoms. Representative examples are cyclopropyl, cyclobutyl, cyclopentyl, cyclohexyl, cycloheptyl, cyclooctyl and the like.

The term "cycloalkenyl" as used herein represents a carbocyclic group having from 3 to 10 carbon atoms containing at least one double bond. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a saturated or partially unsaturated 3 to 10 membered ring containing one or more heteroatoms selected from nitrogen, oxygen and sulfur. Representative examples are pyrrolidinyl, piperidyl, piperazinyl, morpholinyl, thiomorpholinyl, aziridinyl, tetrahydrofuranyl and the like.

The term "aryl" as used herein represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "heteroaryl" as used herein represents a heterocyclic aromatic ring system containing one or more heteroatoms selected from nitrogen, oxygen and sulfur such as furanyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothienyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-lower alkyl", "heteroaryl-lower alkyl", "aryl-lower alkenyl" etc. mean a lower alkyl or alkenyl as defined above, substituted by an aryl or heteroaryl as defined above, for example:

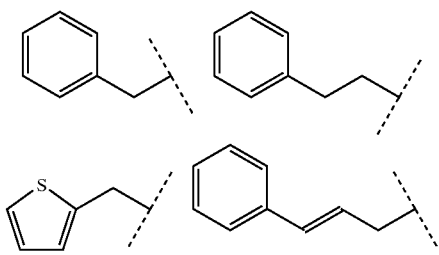

Certain of the above defined terms may occur more than once in the structural formulae, and upon such occurrence each term shall be defined independently of the other.

Within the context of the present invention, a non-peptide is understood to refer to any chemical compound which is not a peptide. In this context a peptide is defined as a linear sequence of natural amino acids coupled by peptide bonds of a length of at least 6 amino acids including derivatives thereof wherein one or more of the amino acid residues have been chemically modified, eg by alkylation, acylation, ester formation or amide formation.

Within the context of the present invention, a GLP-1 agonist is understood to refer to any compound which fully or partially activates the human GLP-1 receptor.

Within the context of the present invention, a partial GLP-1 agonist is understood to refer to any compound which increases the activity of the human GLP-1 receptor but which compared to GLP-1 is not able to effect a full response ($E_{max}$<100% relative to GLP-1).

Within the context of the present invention, a GLP-1 antagonist is understood to refer to any compound which decreases the activity of the human GLP-1 receptor seen after stimulation with GLP-1.

Within the context of the present invention an inverse GLP-1 agonist is understood to refer to any compound which not only decreases the activity of the human GLP-1 receptor seen after stimulation with GLP-1 but also decreases the activity of the non-stimulated receptor (basal activity).

Within the context of the present invention a metabolic disorder is understood to refer to any disorder associated with the metabolism or resulting from a defect of the metabolism.

Within the context of the present invention GLP-1 is understood to refer to either or both of the above two native forms GLP-1 (7-36) and GLP-1 (7-37) unless otherwise specified.

DETAILED DESCRIPTION OF THE INVENTION

The present invention relates to compounds of the general formula (I):

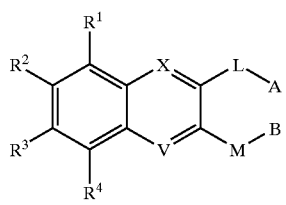

(I)

wherein
$R^1$, $R^2$, $R^3$ and $R^4$ independently are hydrogen, halogen, —CN, —CF$_3$, —NO$_2$, —OR$^5$, lower alkyl, —SR$^5$, —S(O)$_2$NR$^5$R$^6$, —S(O)NR$^5$R$^6$, —S(O)$_2$R$^5$, —S(O)R$^5$, —C(O)NR$^5$R$^6$, —CH$_2$OR$^5$, —CH$_2$NR$^5$R$^6$, —NR$^5$R$^6$, —C(O)R$^5$ or —C(O)OR$^5$, wherein $R^5$ and $R^6$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, or $R^5$ and $R^6$ together with the nitrogen atom to which they are bound form a 3 to 8 membered heterocyclic ring optionally containing one or more further heteroatoms selected from nitrogen, oxygen and sulfur and optionally containing one or more double bonds, in which the cycloalkyl, cycloalkenyl, heterocyclyl, aryl and heteroaryl rings may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH$_3$, —C(O)NH$_2$, —OCH$_2$C(O)NH$_2$, —NH$_2$, —N(CH$_3$)$_2$, —CH$_2$N(CH$_3$)$_2$, —SO$_2$NH$_2$, —OCHF$_2$, —CF$_3$ and —OCF$_3$, one of X and V is =N—, and the other is =CD— or =N—, wherein D is hydrogen, halogen, —CN, —CF$_3$, —NO$_2$, —OR$^7$, —NR$^7$R$^8$, lower alkyl, aryl, —C(O)NR$^7$R$^8$, —CH$_2$OR$^7$, —CH$_2$NR$^7$R$^8$ or —C(O)OR$^7$, wherein $R^7$ and $R^8$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, or $R^7$ and $R^8$ together with the nitrogen atom to which they are bound form a 3 to 8 membered heterocyclic ring optionally containing one or more further heteroatoms selected from nitrogen, oxygen and sulfur and optionally containing one or more double bonds, in which the cycloalkyl, cycloalkenyl, heterocyclyl, aryl and heteroaryl rings may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH$_3$, —C(O)NH$_2$, —OCH$_2$C(O)NH$_2$, —NH$_2$, —N(CH$_3$)$_2$, —CH$_2$N(CH$_3$)$_2$, —SO$_2$NH$_2$, —OCHF$_2$, —CF$_3$ and —OCF$_3$, L and M independently are a valence bond, —(CH$_2$)$_m$S(CH$_2$)$_n$—, —(CH$_2$)$_m$O(CH$_2$)$_n$—, —(CH$_2$)$_m$S(O)(CH$_2$)$_n$—, —(CH$_2$)$_m$S(O)$_2$(CH$_2$)$_n$—, —(CH$_2$)$_m$CH=CH(CH$_2$)$_n$—, —(CH$_2$)$_m$C≡C(CH$_2$)$_n$—, —(CH$_2$)$_m$CHR$^9$(CH$_2$)$_n$—, —(CH$_2$)$_m$NR$^9$(CH$_2$)$_n$—, —(CH$_2$)$_m$C(O)NR$^9$(CH$_2$)$_n$—, —(CH$_2$)$_m$C(O)O(CH$_2$)$_n$—, —S(CH$_2$)$_m$C(O)O(CH$_2$)$_n$—, —S(O)$_2$(CH$_2$)$_m$C(O)O(CH$_2$)$_n$—, —S(O)$_2$(CH$_2$)$_m$C(O)(CH$_2$)$_n$—, —S(O)$_2$NR$^9$(CH$_2$)$_m$C(O)O(CH$_2$)$_n$—, —S(CH$_2$)$_m$C(O)NR$^9$(CH$_2$)$_n$—, —(CH$_2$)$_m$OC(O)(CH$_2$)$_n$—, —(CH$_2$)$_m$C(O)(CH$_2$)$_n$—, —(CH$_2$)$_m$C(NOR$^9$)(CH$_2$)$_n$—, —(CH$_2$)$_m$NR$^9$S(O)$_2$(CH$_2$)$_n$—, —(CH$_2$)$_m$S(O)$_2$NR$^9$(CH$_2$)$_n$—, —(CH$_2$)$_m$CHOR$^9$(CH$_2$)$_n$—, —(CH$_2$)$_m$P(O)(OR$^9$)O(CH$_2$)$_n$—, —S(O)$_2$(CH$_2$)$_m$CONR$^9$(CH$_2$)$_n$—, —S(O)$_2$(CH$_2$)$_m$OC(O)NR$^9$(CH$_2$)$_n$C(O)O(CH$_2$)$_r$—, —NR$^9$O(CH$_2$)$_n$—, —NR$^9$NR$^{9a}$C(O)NR$^{9b}$(CH$_2$)$_n$—, —NR$^9$(CH$_2$)$_m$NR$^{9a}$C(O)(CH$_2$)$_n$— or —NR$^9$(CR$^{9c}$R$^{9d}$)$_n$—, wherein R$^9$, R$^{9a}$ and R$^{9b}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, in which the cycloalkyl, cycloalkenyl, heterocyclyl, aryl and heteroaryl rings may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH$_3$, —C(O)NH$_2$, —OCH$_2$C(O)NH$_2$, —NH$_2$, —N(CH$_3$)$_2$, —CH$_2$N(CH$_3$)$_2$, —SO$_2$NH$_2$, —OCHF$_2$, —CF$_3$ and —OCF$_3$, R$^{9c}$ and R$^{9d}$ independently are hydrogen or lower alkyl, m, n and r independently are 0, 1, 2, 3 or 4, A and B independently are hydrogen, halogen, —CF$_3$, —CF$_2$CF$_3$, —CN, —NO$_2$, lower alkyl, lower alkenyl, lower alkynyl, cycloalkyl, hydroxy, in which the cycloalkyl ring may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH$_3$, —C(O)NH$_2$, —OCH$_2$C(O)NH$_2$, —NH$_2$, —N(CH$_3$)$_2$, —CH$_2$N(CH$_3$)$_2$, —SO$_2$NH$_2$, —OCHF$_2$, —CF$_3$ and —OCF$_3$, or A and B independently are

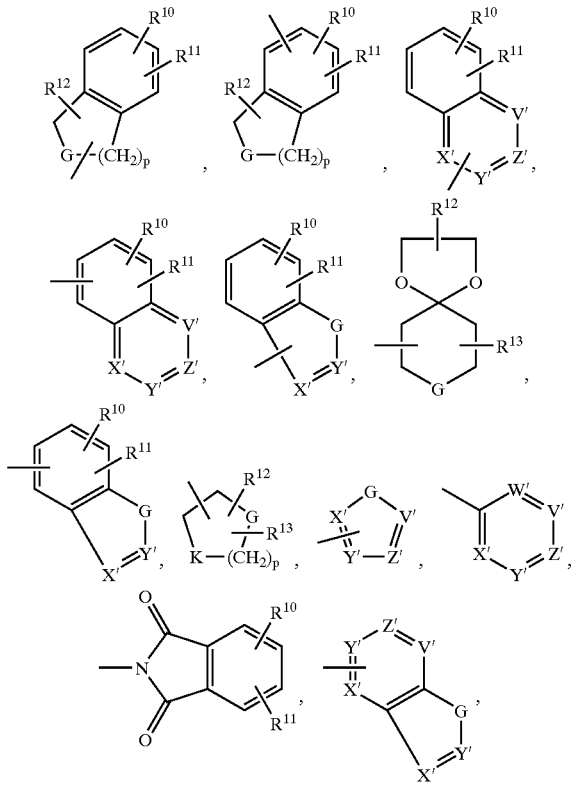

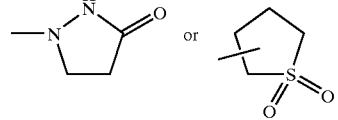

wherein p is 1, 2 or 3,

X' is —N= or —CR$^{14}$=,

Y' is —N= or —CR$^{15}$=,

Z' is —N= or —CR$^{16}$=,

V' is —N= or —CR$^{17}$=,

W' is —N= or —CR$^{18}$=,

G is —CR$^{18a}$R$^{18b}$, —N$^+$O$^-$—, —NR$^{19}$—, —O— or —S—,

K is —CR$^{18c}$R$^{18d}$—, —NR$^{20}$, —O— or —S—,

R$^{10}$, R$^{11}$, R$^{12}$, R$^{13}$, R$^{14}$, R$^{15}$, R$^{16}$, R$^{17}$, R$^{18}$, R$^{18a}$, R$^{18b}$, R$^{18c}$ and R$^{18d}$ independently are hydrogen, halogen, —CN, —CF$_3$, —OCF$_3$, —OCH$_2$CF$_3$, —OCF$_2$CHF$_2$, —NO$_2$, —OR$^{21}$, —NR$^{21}$R$^{22}$, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —SCF$_3$, —SR$^{21}$, —CHF$_2$, —OCHF$_2$, —OS(O)$_2$CF$_3$, —OS(O)$_2$R$^{21}$, —NR$^{21}$S(O)$_2$R$^{22}$, —S(O)$_2$NR$^{21}$R$^{22}$, —S(O)NR$^{21}$R$^{22}$, —S(O)$_2$R$^{21}$, —S(O)R$^{21}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —S(O)$_2$NR$^{21}$(CH)$_5$C(O)OR$^{22}$, —C(O)NR$^{21}$(CH)$_5$C(O)OR$^{22}$ or —C(O)NR$^{21}$R$^{22}$ where R$^{12}$ and R$^{13}$ furthermore independently may represent oxo, or two of the groups R$^{10}$ to R$^{18d}$ when defined in the same ring together may form a bridge —O(CH$_2$)$_q$O— or —CH$_2$O(CH$_2$)$_q$O—, in which the cycloalkyl, cycloalkenyl, heterocyclyl, aryl and heteroaryl rings may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH$_3$, —C(O)NH$_2$, —OCH$_2$C(O)NH$_2$, —NH$_2$, —N(CH$_3$)$_2$, —CH$_2$N(CH$_3$)$_2$, —SO$_2$NH$_2$, —OCHF$_2$, —CF$_3$ and —OCF$_3$, wherein R$^{21}$ and R$^{22}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyl-lower alkyl, heterocyclyl-lower alkenyl, heterocyclyl-lower alkynyl, heteroaryl-lower alkyl, heteroaryl-lower alkenyl or heteroaryl-lower alkynyl, or R$^{21}$ and R$^{22}$ together with the nitrogen atom to which they are bound form a 3 to 8 membered heterocyclic ring optionally containing one or more further heteroatoms selected from nitrogen, oxygen and sulfur and optionally containing one or more double bonds, in which the cycloalkyl, cycloalkenyl, heterocyclyl, aryl and heteroaryl rings may optionally be substituted with one or more substituents independently selected from halogen, lower alkyl, lower alkanoyl, —OH, —CH$_2$OH, —NO$_2$, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃, $R^{19}$ and $R^{20}$ independently are hydrogen, —OR²³, —NR²³R²⁴, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —C(O)NR²³R²⁴ or —C(O)OR²³, in which the cycloalkyl, cycloalkenyl, heterocyclyl, aryl and heteroaryl rings may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃, wherein $R^{23}$ and $R^{24}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, or $R^{23}$ and $R^{24}$ together with the nitrogen atom to which they are bound form a 3 to 8 membered heterocyclic ring optionally containing one or more further heteroatoms selected from nitrogen, oxygen and sulfur and optionally containing one or more double bonds, in which the cycloalkyl, cycloalkenyl, heterocyclyl, aryl and heteroaryl rings may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃, q is 1, 2 or 3, s is 0, 1, 2 or 3, or A and B may be connected and together form a C₂₋₃-alkylene radical, with the provisos that when L represents a group wherein n or r is 0, A is not halogen, —CN or —NO₂, and when M represents a group wherein n or r is 0, B is not halogen, —CN or —NO₂, as well as any optical or geometric isomer or tautomeric form thereof including mixtures of these or a pharmaceutically acceptable salt thereof.

In one embodiment the compounds have the general formula (II):

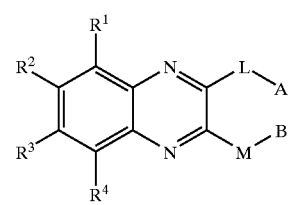

(II)

wherein $R^1$, $R^2$, $R^3$, $R^4$, L, M, A and B are as defined for formula (I).

In another embodiment the compounds have the general formula (III):

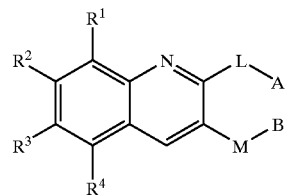

(III)

wherein $R^1$, $R^2$, $R^3$, $R^4$, L, M, A and B are as defined for formula (I).

$R^1$, $R^2$, $R^3$ and $R^4$ are preferably independently hydrogen, halogen, —CN, —CF₃, —NO₂, lower alkyl, lower alkoxy, —S(O)₂NR⁵R⁶, —S(O)NR⁵R⁶, —S(O)₂R⁵, —C(O)NR⁵R⁶, —SR⁵, —C(O)R⁵ or —C(O)OR⁵, wherein $R^5$ and $R^6$ are as defined for formula (I).

More preferably, $R^1$, $R^2$, $R^3$ and $R^4$ are independently hydrogen, halogen, —CN, —CF₃, lower alkyl, lower alkoxy, —SR⁵, —S(O)₂R⁵, —C(O)OR⁵, —C(O)R⁵, —NO₂ or —C(O)NR⁵R⁶, wherein $R^5$ and $R^6$ are as defined for formula (I). $R^5$ and $R^6$ are preferably independently hydrogen, phenyl or lower alkyl, wherein phenyl optionally is substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃.

Even more preferably, $R^1$, $R^2$, $R^3$ and $R^4$ are independently hydrogen, halogen, —CN, —CF₃, —NO₂, —C(O)phenyl, lower alkyl or lower alkoxy, wherein phenyl optionally is substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃.

Of these $R^1$, $R^2$, $R^3$ and $R^4$ are preferably independently hydrogen, halogen, —CF₃, —NO₂ or —C(O)phenyl.

In one embodiment three of the groups $R^1$ to $R^4$ are hydrogen and one of them is different from hydrogen. In one preferred embodiment thereof one of $R^1$ to $R^4$ is halogen, especially chloro. In another preferred embodiment thereof $R^3$ is —NO₂.

In another embodiment two of the groups $R^1$ to $R^4$ are hydrogen and the other two are different from hydrogen. In one preferred embodiment thereof $R^1$ and $R^4$ are both hydrogen and $R^2$ and $R^3$ are both halogen, especially chloro. In another preferred embodiment thereof $R^1$ and $R^4$ are both hydrogen and $R^2$ and $R^3$ are both —NO₂.

L is preferably a valence bond, —(CH₂)ₘS(CH₂)ₙ—, —(CH₂)ₘS(O)(CH₂)ₙ—, —(CH₂)ₘS(O)₂(CH₂)ₙ—, —(CH₂)ₘCHR⁹(CH₂)ₙ—, —S(O)₂(CH₂)ₘC(O)O(CH₂)ₙ—, —S(O)₂(CH₂)ₘC(O)(CH₂)ₙ—, —S(O)₂NR⁹(CH₂)ₘC(O)O(CH₂)ₙ—, —S(O)₂(CH₂)ₘOC(O)NR⁹(CH₂)ₙC(O)O(CH₂)ᵣ— or —S(O)₂(CH₂)ₘCONR⁹(CH₂)ₙ—, wherein m, n, r and R⁹ are as defined for formula (I).

More preferably, L is a valence bond, —S—, —S(O)—, —S(O)₂(CH₂)ₙ—, —S(O)₂(CH₂)₂C(O)O(CH₂)ₙ—, —S(O)₂(CH₂)₂C(O)(CH₂)ₙ—, —S(O)₂NH(CH₂)₂C(O)O(CH₂)ₙ—, —S(O)₂(CH₂)₄OC(O)NH(CH₂)₂C(O)O— or —S(O)₂(CH₂)₂CONH(CH₂)ₙ—, wherein n is as defined for formula (I).

Among these L is preferably a valence bond, —S—, —S(O)—, —S(O)₂—, —S(O)₂CH₂—, —S(O)₂(CH₂)₂—, —S(O)₂(CH₂)₂C(O)O—, —S(O)₂(CH₂)₂C(O)(CH₂)₂—, —S(O)₂NH(CH₂)₂C(O)O—, —S(O)₂(CH₂)₄OC(O)NH(CH₂)₂C(O)O— or —S(O)₂(CH₂)₂CONH(CH₂)₂— and even more preferably L is —S(O)₂CH₂— or —S(O)₂—.

A is preferably lower alkyl, halogen, —CF₃, —OH, —NO₂, cycloalkyl, in which the cycloalkyl ring may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃, or A is

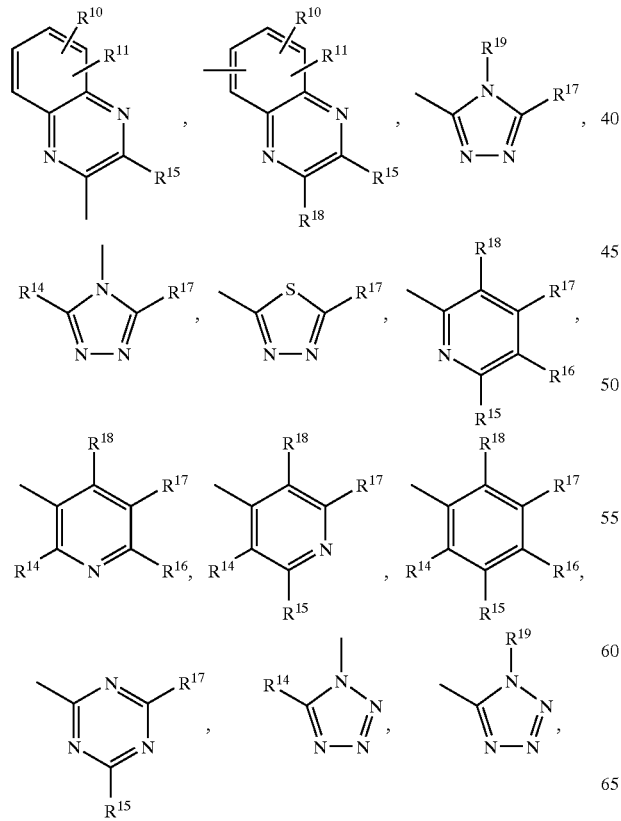

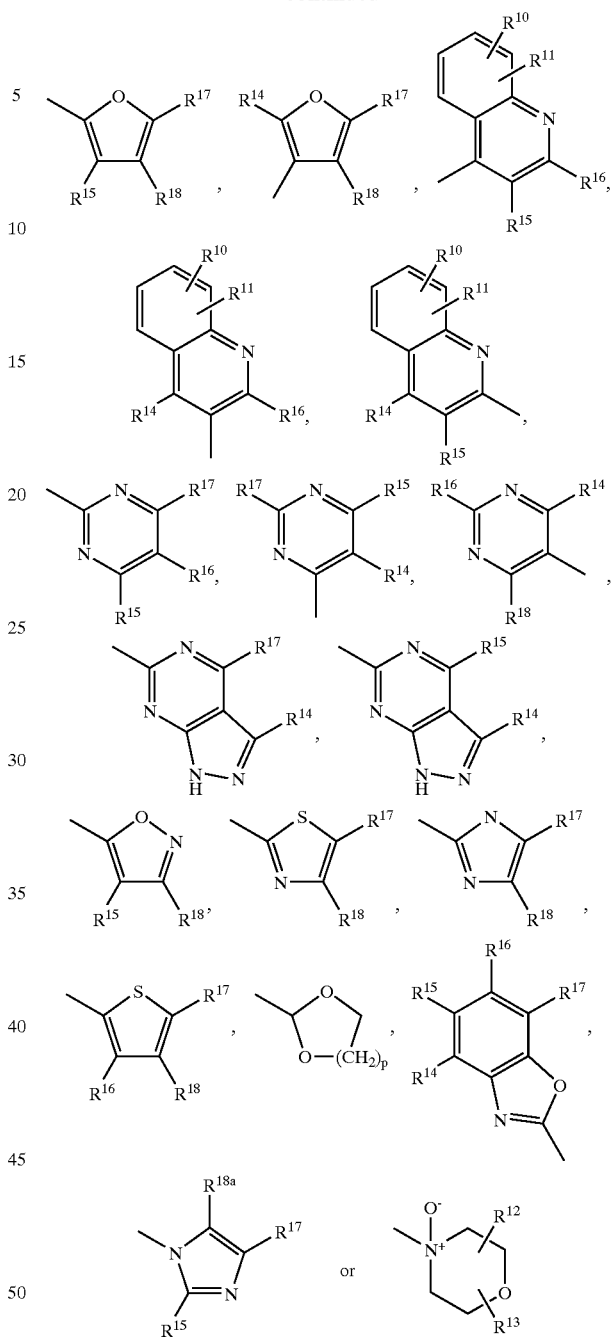

wherein R¹⁰, R¹¹, R¹², R¹³, R¹⁴, R¹⁵, R¹⁶R¹⁷, R¹⁸, R¹⁸, R¹⁸ᵃ and R¹⁹ are as defined for formula (I).

More preferably, A is lower alkyl, halogen, —CF₃, —OH, cycloalkyl, in which the cycloalkyl ring may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₂, —OCHF₂, —CF₃ and —OCF₃, or A is

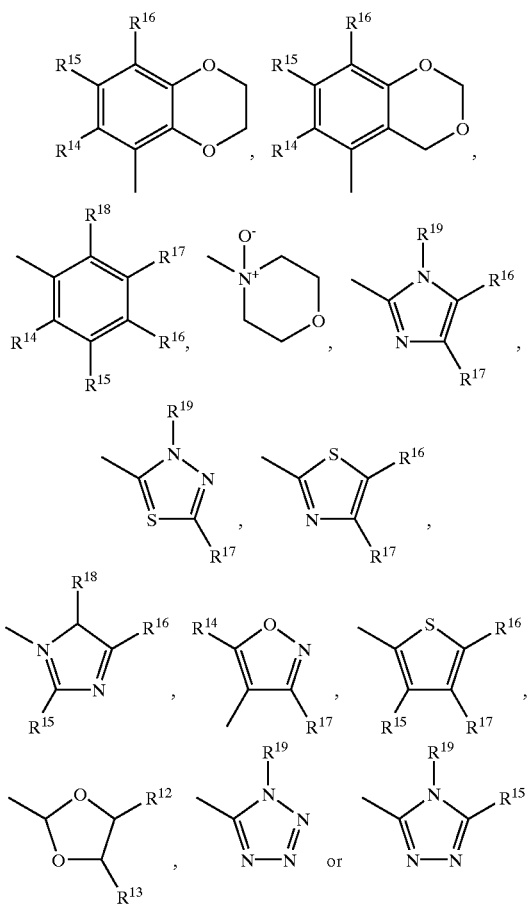

wherein $R^{12}$ to $R^{19}$ are as defined for formula (I).

Preferably, $R^{12}$ and $R^{13}$ are independently selected from hydrogen and lower alkyl, $R^{14}$ to $R^{18}$ are independently selected from hydrogen, lower alkyl, —$NO_2$, halogen, —$S(O)_2R^{21}$, —$CONR^{21}R^{22}$, —$OCHF_2$, —$S(O)_2NR^{21}(CH)_sC(O)OR^{22}$, wherein s is 1 or 2, $R^{21}$ and $R^{22}$ are independently hydrogen, lower alkyl or pyridyl, and $R^{19}$ is hydrogen, lower alkyl or phenyl.

Even more preferably, A is lower alkyl, halogen, —$CF_3$, —OH, cycloalkyl, or A is

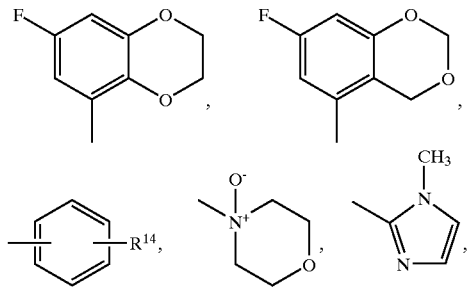

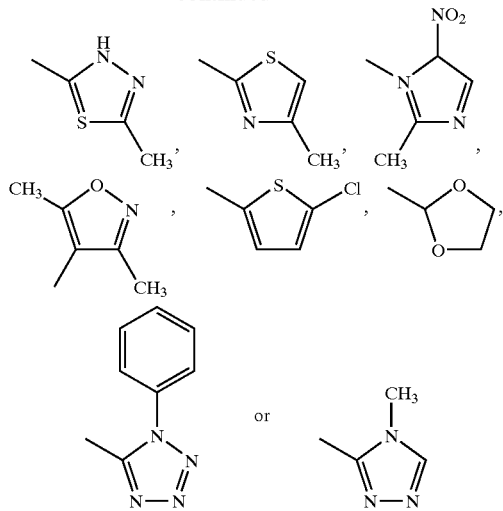

wherein $R^{14}$ is —$S(O)_2CH_3$, —$CONH_2$, —CONH-pyridyl, —$OCHF_2$ or —$S(O)_2NH(CH)_2C(O)OCH_3$.

In one preferred embodiment thereof A is lower alkyl.

M is preferably a valence bond, —$(CH_2)_mS(CH_2)_n$—, —$(CH_2)_mS(O)_2(CH_2)_n$—, —$(CH_2)_mNR^9(CH_2)_n$—, —$NR^9(CR^{9c}R^{9d})_n$—, —$(CH_2)_mC(O)O(CH_2)_n$—, —$NR^9O(CH_2)_n$—, —$(CH_2)_mCH=CH(CH_2)_n$—, —$NR^9NR^{9a}C(O)NR^{9b}(CH_2)_n$—, —O— or —$(CH_2)_mCHR^9(CH_2)_n$— wherein m, n, $R^9$, $R^{9a}$, $R^{9b}$, $R^{9c}$ and $R^{9d}$ are as defined for formula (I).

More preferably, M is a valence bond, —C(O)O—, —CH=CH—, —$N(CH_3)$—, —$CH_2S(O)_2$—, —NH—, —$CH_2CH_2$—, —$N(CH_3)O$—, $NHOCH_2$—, —S—, —$NHCH_2CH_2NHC(O)$—, —$NHC(CH_3)_2$—, —$CH_2S$—, —$NHCH_2$—, —$NHCH_2CH_2$—, —O— or —$CH_2$—.

Even more preferably, M is a valence bond, —C(O)O—, —CH=CH—, —$N(CH_3)$—, —$CH_2S(O)_2$—, —NH—, —$CH_2CH_2$—, —$N(CH_3)O$—, $NHOCH_2$—, —S—, —$NHCH_2CH_2NHC(O)$— or —$NHC(CH_3)_2$—.

In a preferred embodiment thereof M is a valence bond, —NH— or —$N(CH_3)$—.

B is preferably hydrogen, halogen, —$CF_3$, —$CF_2CF_3$, lower alkyl, cycloalkyl, in which the cycloalkyl ring may optionally be substituted with one or more substituents independently selected from halogen, lower alkyl, lower alkanoyl, —OH, —$CH_2OH$, —$NO_2$, —CN, —C(O)OH, —O-lower alkyl, —$C(O)OCH_3$, —$C(O)NH_2$, —$OCH_2C(O)NH_2$, —$NH_2$, —$N(CH_3)_2$, —$CH_2N(CH_3)_2$, —$SO_2NH_2$, —$OCHF_2$, —$CF_3$ and —$OCF_3$, or B is

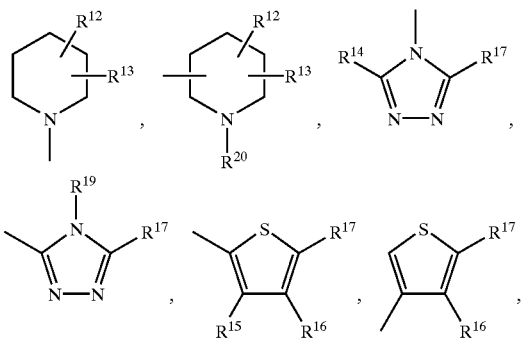

-continued

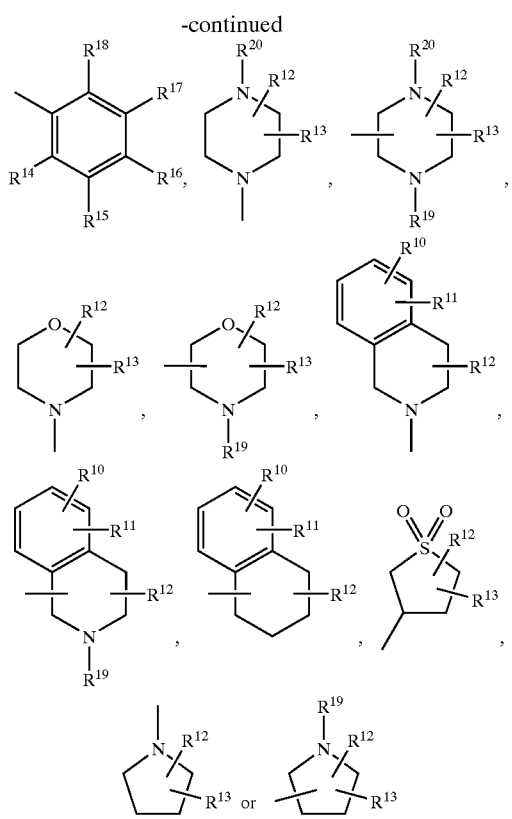

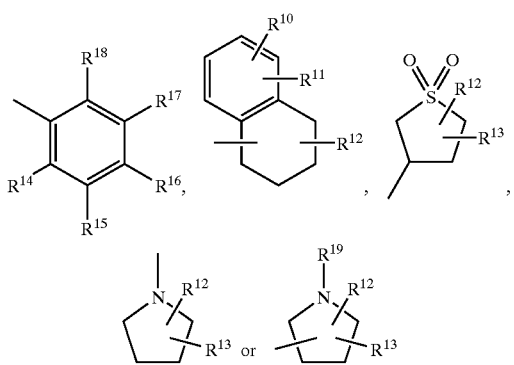

wherein $R^{10}$ to $R^{19}$ are as defined for formula (I).

Preferably, $R^{10}$ and $R^{11}$ are independently hydrogen, lower alkyl, halogen, —$OCF_3$, —$OCHF_2$, —$CF_3$ or —$NO_2$, $R^{12}$ and $R^{13}$ are independently hydrogen, hydroxy or lower alkyl, $R^{14}$ to $R^{18}$ are independently hydrogen, lower alkyl, halogen, —$OCF_3$, —$OCHF_2$, —$CF_3$ or —$NO_2$, and $R^{19}$ is hydrogen or lower alkyl.

Even more preferably, B is hydrogen, —$CF_3$, lower alkyl, cycloalkyl,

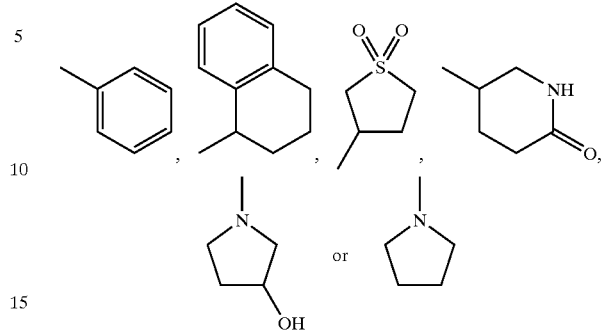

In a preferred embodiment thereof B is —$CF_3$ or lower alkyl, and especially preferably B is lower alkyl.

In another preferred embodiment the present compounds have the general formula (IV):

(IV)

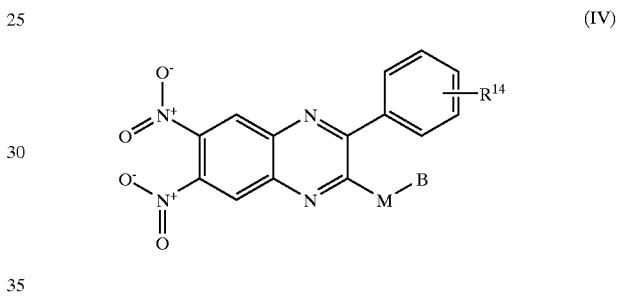

wherein M, B and $R^{14}$ are as defined for formula (I) or as defined in anyone of the preferred embodiments above.

In another preferred embodiment the present compounds have the general formula (V):

(V)

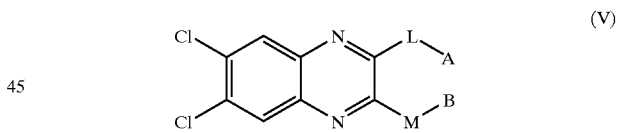

wherein L is —$S(CH_2)_n$—, —$S(O)(CH_2)_n$— or —$S(O)_2$ $(CH_2)_n$—, and n, A, M and B are as defined for formula (I) or as defined in anyone of the preferred embodiments above.

In a preferred embodiment of the above formulae (IV) and (V) M is a valence bond and B is —$CF_3$ or lower alkyl.

In another preferred embodiment of the above formulae (IV) and (V) M is —$NR^9$—, wherein $R^9$ is hydrogen or lower alkyl and B is lower alkyl or

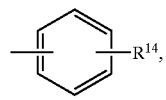

wherein $R^{14}$ is hydrogen, lower alkyl, halogen, —$OCF_3$, —$OCHF_2$, —$CF_3$ or —$NO_2$.

In a further aspect the present invention relates to a compound of the general formula (I'):

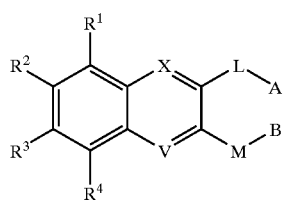

wherein
R¹, R², R³ and R⁴ independently are hydrogen, halogen, —CN, —CF₃, —NO₂, —OR⁵, lower alkyl, —SR⁵, —S(O)₂NR⁵R⁶, —S(O)NR⁵R⁶, —S(O)₂R⁵, —C(O)NR⁵R⁶, —CH₂OR⁵, —CH₂NR⁵R⁶ or —C(O)OR⁵;
wherein R⁵ and R⁶ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or R⁵ and R⁶ together with the nitrogen atom to which they are bound form a 3 to 8 membered heterocyclic ring optionally containing one or more further heteroatoms selected from nitrogen, oxygen and sulfur and optionally containing one or more double bonds;
one of X and V is =N—; and the other is =CD— or =N—;
wherein D is hydrogen, halogen, —CN, —CF₃, —NO₂, —OR⁷, —NR⁷R⁸, lower alkyl, aryl, —C(O)NR⁷R⁸, —CH₂OR⁷, —CH₂NR⁷R⁸ or —C(O)OR⁷;
wherein R⁷ and R⁸ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or R⁷ and R⁸ together with the nitrogen atom to which they are bound form a 3 to 8 membered heterocyclic ring optionally containing one or more further heteroatoms selected from nitrogen, oxygen and sulfur and optionally containing one or more double bonds;
L and M independently are a valence bond, —(CH₂)$_m$S(CH₂)$_n$—, —(CH₂)$_m$O(CH₂)$_n$—, (CH₂)$_m$S(O)(CH₂)$_n$—, —(CH₂)$_m$S(O)₂(CH₂)$_n$—, —(CH₂)$_m$CH=CH(CH₂)$_n$—, —(CH₂)$_m$C≡C(CH₂)$_n$—, —(CH₂)$_m$CHR⁹(CH₂)$_n$—, —(CH₂)$_m$NR⁹(CH₂)$_n$—, —(CH₂)$_m$C(O)NR⁹(CH₂)$_n$—, —(CH₂)$_m$C(O)O(CH₂)$_n$—, —S(CH₂)$_m$C(O)O(CH₂)$_n$—, —S(CH₂)$_m$C(O)NR⁹(CH₂)$_n$—, —(CH₂)$_m$OC(O)(CH₂)$_n$—, —(CH₂)$_m$C(O)(CH₂)$_n$—, —(CH₂)$_n$C(NOR⁹)(CH₂)$_n$—, —(CH₂)$_m$NR⁹S(O)₂(CH₂)$_n$—, —(CH₂)$_m$S(O)₂NR⁹(CH₂)$_n$—, —(CH₂)$_m$CHOR⁹(CH₂)$_n$— or —(CH₂)$_m$P(O)(OR⁹)O(CH₂)$_n$—;
wherein R⁹ is hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl;
m and n independently are 0, 1, 2 or 3;
A and B independently are hydrogen, halogen, —CF₃, —CF₂CF₃, —CN, —NO₂, lower alkyl, lower alkenyl, lower alkynyl,

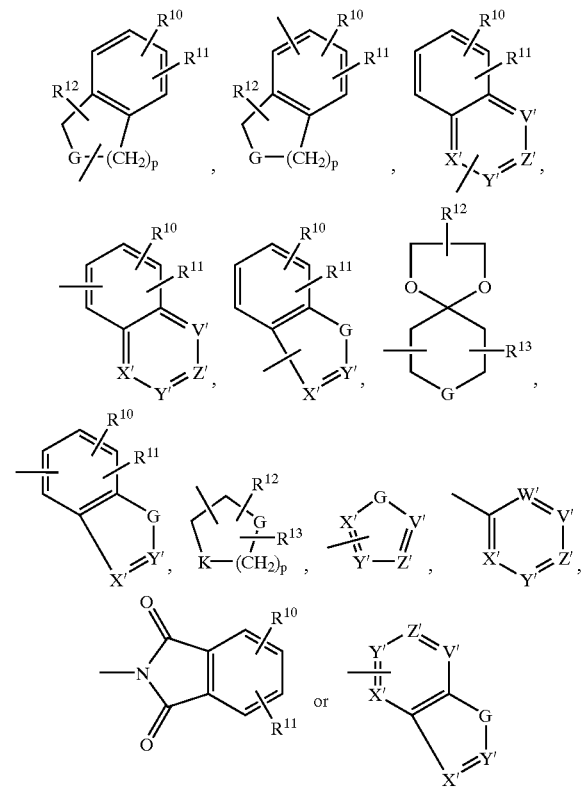

wherein
p is 1, 2 or 3;
X' is —N= or —CR¹⁴=;
Y' is —N= or —CR¹⁵=;
Z' is —N= or —CR¹⁶=;
V' is —N= or —CR¹⁷=;
W' is —N= or —CR¹⁸=;
G is —NR¹⁹—, —O— or —S—;
K is —NR²⁰—O— or —S—;
R¹⁰, R¹¹, R¹², R¹³, R¹⁴, R¹⁵, R¹⁶, R¹⁷ and R¹⁸ independently are hydrogen, halogen, —CN, —CF₃, —OCF₃, —OCH₂CF₃, —OCF₂CHF₂, —NO₂, —OR²¹, —NR²¹R²², lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —SCF₃, —SR²¹, —CHF₂, —OCHF₂, —OS(O)₂CF₃, —OS(O)₂R²¹, —NR²¹S(O)₂R²², —S(O)₂NR²¹R²², —S(O)NR²¹R²², —S(O)₂R²¹, —S(O)R²¹, —(O)NR²¹R²², —CH₂C(O)NR²¹R²², —OCH₂C(O)NR²¹R²², —CH₂OR²¹, —CH₂NR²¹R²², —OC(O)R²¹ or —(O)

$OR^{21}$, where $R^{12}$ and $R^{13}$ furthermore independently may represent oxo; or two of the groups $R^{10}$ to $R^{18}$ when defined in the same ring together may form a bridge —OCH$_2$O—;

wherein $R^{21}$ and $R^{22}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or $R^{21}$ and $R^{22}$ together with the nitrogen atom to which they are bound form a 3 to 8 membered heterocyclic ring optionally containing one or more further heteroatoms selected from nitrogen, oxygen and sulfur and optionally containing one or more double bonds;

$R^{19}$ and $R^{20}$ independently are hydrogen, —$OR^{23}$, —$NR^{23}R^{24}$, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —$C(O)NR^{23}R^{24}$ or —$C(O)OR^{23}$;

wherein $R^{23}$ and $R^{24}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or $R^{23}$ and $R^{24}$ together with the nitrogen atom to which they are bound form a 3 to 8 membered heterocyclic ring optionally containing one or more further heteroatoms selected from nitrogen, oxygen and sulfur and optionally containing one or more double bonds;

with the provisos that when L represents a group wherein n is 0, A is not halogen, —CN or —NO$_2$; and when M represents a group wherein n is 0, B is not halogen, —CN or —NO$_2$;

as well as any optical or geometric isomer or tautomeric form thereof including mixtures of these or a pharmaceutically acceptable salt thereof.

In a preferred embodiment the invention relates to a compound of the general formula (II'):

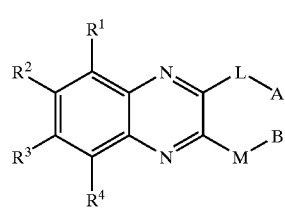

(II')

wherein $R^1$, $R^2$, $R^3$, $R^4$, L, M, A and B are as defined for formula (I').

Preferably, $R^1$, $R^2$, $R^3$ and $R^4$ are independently hydrogen, halogen, —CN, —CF$_3$, —NO$_2$, lower alkyl, lower alkoxy, —S(O)$_2$NR$^5$R$^6$, —S(O)NR$^5$R$^6$, —S(O)$_2$R$^5$, —C(O)NR$^5$R$^6$ or —C(O)OR$^5$, wherein $R^5$ and $R^6$ are as defined for formula (I').

In one preferred embodiment, $R^1$, $R^2$, $R^3$ and $R^4$ are independently hydrogen, halogen, —CN, —CF$_3$ or —S(O)$_2$R$^5$, wherein $R^5$ is as defined for formula (I').

In another preferred embodiment, $R^1$, $R^2$, $R^3$ and $R^4$ are independently hydrogen, halogen, —CN, —CF$_3$, lower alkyl, lower alkoxy or —C(O)NR$^5$R$^6$, wherein $R^5$ and $R^6$ independently are hydrogen or lower alkyl.

Among these, $R^1$, $R^2$, $R^3$ and $R^4$ are preferably independently hydrogen, halogen, —CN, lower alkyl or lower alkoxy.

In a further preferred embodiment two of the groups $R^1$ to $R^4$ are hydrogen and the other two are different from hydrogen.

Preferably, $R^1$ and $R^4$ are both hydrogen and $R^2$ and $R^3$ are as defined for formula (I') or as defined in the above preferred embodiments thereof.

In still a further preferred embodiment $R^2$ and $R^3$ are both halogen.

In a preferred embodiment of the invention L is a valence bond, —(CH$_2$)$_m$S(CH$_2$)$_n$—, —(CH$_2$)$_m$S(O)(CH$_2$)$_n$—, —(CH$_2$)$_m$S(O)$_2$(CH$_2$)$_n$— or —(CH$_2$)$_m$CHR$^9$(CH$_2$)$_n$—, wherein m, n and $R^9$ are as defined for formula (I).

Still more preferred L is a valence bond, —CH$_2$—, —CH$_2$S—, —S—, —S(O)— or —S(O)$_2$—.

Even more preferred L is —S—, —S(O)— or —S(O)$_n$—.

In a further preferred embodiment A is lower alkyl, halogen,

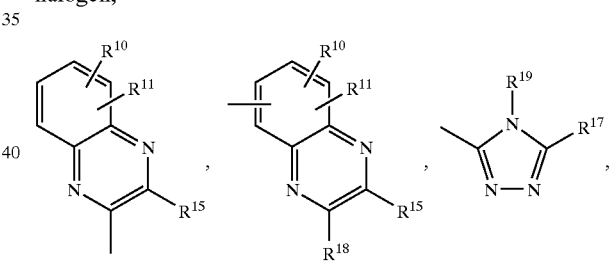

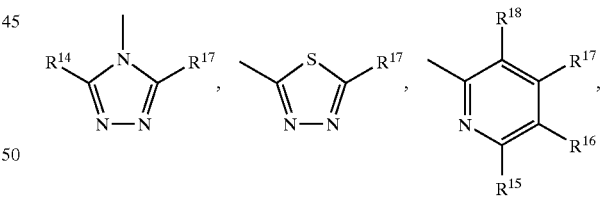

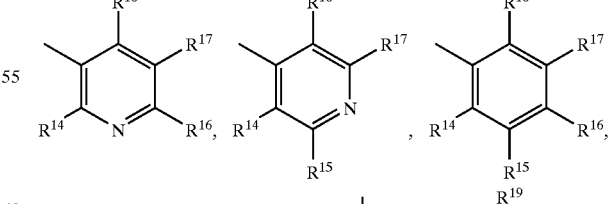

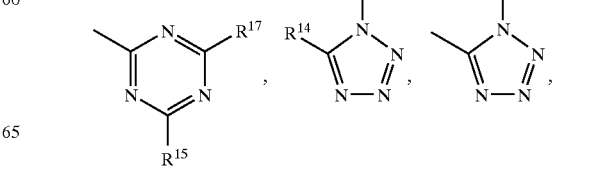

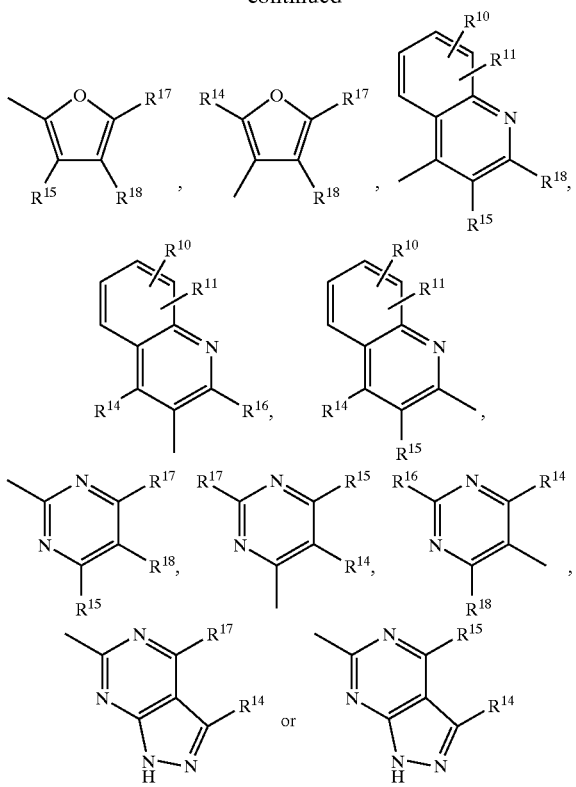

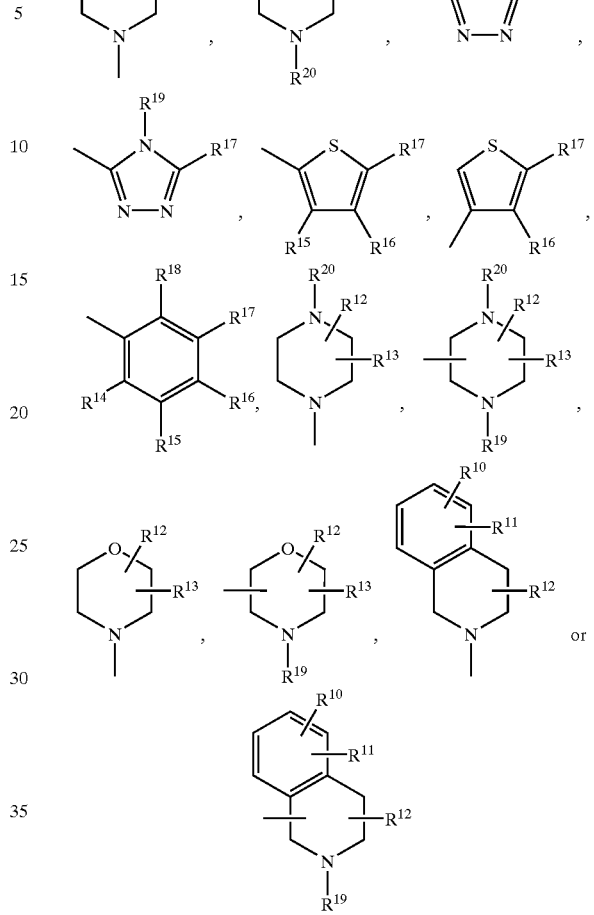

wherein $R^{10}$, $R^{11}$, $R^{14}$, $R^{15}$, $R^{16}$, $R^{17}$, $R^{18}$ and $R^{19}$ are as defined for formula (I')

$R^{10}$, $R^{11}$, $R^{14}$, $R^{15}$, $R^{16}$, $R^{17}$, $R^{18}$ and $R^{19}$ are preferably independently selected from hydrogen, halogen, lower alkyl, —$NH_2$, —$CF_2$, —CN, —S-(cycloalkyl-lower alkyl), —NHC(O)(cycloalkyl-lower alkyl), —C(O)$NH_2$, —S-lower alkyl, —O-lower alkyl phenyl, furanyl, thienyl, —NHC(O)O-lower alkyl and —C(O)$CH_3$. $R^{19}$ is preferably lower or hydrogen.

More preferred A is lower alkyl,

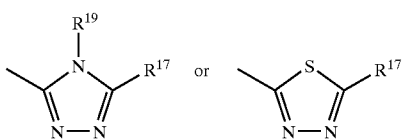

wherein $R^{17}$ and $R^{19}$ are as defined for formula (I) or in the above preferred embodiments thereof. $R^{17}$ is preferably lower alkyl, —$NH_2$ or —S-lower alkyl and $R^{19}$ is preferably hydrogen.

In still a preferred embodiment of the invention M is a valence bond, —$(CH_2)_m S(CH_2)_n$—, $(CH_2)_m CH=CH(CH_2)_n$— or —$(CH_2)_m CHR^9 (CH_2)_n$— wherein m, n and $R^9$ are as defined for formula (I').

Of these M is preferably a valence bond, —$CH_2 S$—, —CH=CH—, —$CH_2 CH_2$— or —$CH_2$—.

Even more preferred M is a valence bond.

In yet another preferred embodiment of the invention B is hydrogen, halogen, —$CF_3$, —$CF_2 CF_3$, lower alkyl, wherein $R^{10}$ to $R^{20}$ are as defined for formula (I').

$R^{10}$, $R^{11}$, $R^{12}$, $R^{13}$, $R^{14}$, $R^{15}$, $R^{16}$, $R^{17}$ and $R^{18}$ are preferably independently selected from hydrogen, halogen, lower alkyl, —$NH_2$, —$CF_3$, —CN, —S-(cycloalkyl-lower alkyl), —NHC(O)(cycloalkyl-lower alkyl), —C(O)$NH_2$, —S-lower alkyl, —O-lower alkyl, phenyl, furanyl, thienyl, —NHC(O)O-lower alkyl and —C(O)$CH_3$. $R^{19}$ and $R^{20}$ are preferably independently selected from lower alkyl and hydrogen.

More preferred B is —$CF_3$ or lower alkyl.

In a further aspect the invention relates to a compound of the formula (II') as defined above wherein $R^2$ and $R^3$ are both either halogen, —CN or —$CF_3$, L is —$S(CH_2)_n$—, —$S(O)(CH_2)_n$— or —$S(O)_2(CH_2)_n$— wherein n is 0, 1, 2 or 3, and $R^1$, $R^4$, A, M and B are as defined for formula (I') or as defined in the above preferred embodiments thereof.

In another aspect the invention relates to a compound of the formula (II') as defined above wherein L is —$S(CH_2)_n$—, —$S(O)(CH_2)_n$— or —$S(O)_2(CH_2)_n$—, wherein n is 0, 1, 2 or 3, M is a valence bond, B is —$CF_3$ or isopropyl, and $R^1$, $R^2$, $R^3$, $R^4$ and A are as defined for formula (III') or as defined in the above preferred embodiments thereof, with the proviso that when $R^1$, $R^2$, $R^3$ and $R^4$ are hydrogen, B is isopropyl and L is —$SCH_2$—, A must not be hydrogen.

In still another aspect the invention relates to a compound of the formula (II') as defined above wherein L is —$S(CH_2)_n$—, —$S(O)(CH_2)_n$— or —$S(O)_2(CH_2)_n$—, wherein n is 0, 1, 2 or 3, at least one of the groups $R^2$ and $R^3$ are —CN, and $R^1$, $R^4$, A, M and B are as defined for formula (I') or as defined in the above preferred embodiments thereof.

In still another aspect the invention relates to a compound of the formula (II') as defined above wherein L is —S(CH$_2$)$_n$—, —S(O)(CH$_2$)$_n$— or —S(O)$_2$(CH$_2$)$_n$—, wherein n is 0, 1, 2 or 3, $R^1$, $R^2$, $R^3$ and $R^4$ are as defined for formula (I), A is a heterocyclic ring, and M is —CH$_2$S—, —CH═CH—, —CH$_2$CH$_2$— or —CH$_2$—, and B is as defined for formula (I') above or as defined in the above preferred embodiments thereof, or M is a valence bond, and B is —CF$_3$, —CN, lower alkyl, lower alkenyl, lower alkynyl or halogen.

In a further aspect the invention relates to a compound of an EC$_{50}$ value as determined by the method for determining the ability to stimulate cAMP formation in a cell line expressing the cloned human GLP-1 receptor disclosed herein of less than 25 μM and having the general formula (III'):

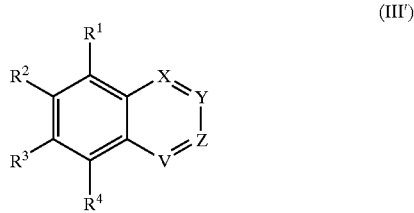

wherein
$R^1$, $R^2$, $R^3$ and $R^4$ independently are hydrogen, halogen, —CN, —CF$_3$, —NO$_2$, —OR$^5$, —NR$^5$R$^6$, lower alkyl, lower alkenyl, lower alkynyl, cycloalkyl, heterocyclyl, heteroaryl, —SR$^5$, —NR$^5$S(O)$_2$R$^6$, —S(O)$_2$NR$^5$R$^6$, —S(O)NR$^5$R$^6$, —S(O)$_2$R$^5$, —C(O)NR$^5$R$^6$, —CH$_2$OR$^5$, —CH$_2$NR$^5$R$^6$ or —C(O)OR$^5$;

wherein $R^5$ and $R^6$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or $R^5$ and $R^6$ together with the nitrogen atom to which they are bound form a 3 to 8 membered heterocyclic ring optionally containing one or more further heteroatoms selected from nitrogen, oxygen and sulfur and optionally containing one or more double bonds;

X, Y, Z and V independently are ═N—; ═C(L—A)—; ═C(M—B)— or ═CD—; with the proviso that one of X, Y, Z and V is ═N—; one is ═C(L—A)—; one is ═C(M—B)—; and the remaining is ═CD— or ═N—;

wherein D is hydrogen, halogen, —CN, —CF$_3$, —NO$_2$, —OR$^7$, —NR$^7$R$^8$, lower alkyl, aryl, —C(O)NR$^7$R$^8$, —CH$_2$OR$^7$, —CH$_2$NR$^7$R$^8$ or —C(O)OR$^7$;

wherein $R^7$ and $R^8$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or $R^7$ and $R^8$ together with the nitrogen atom to which they are bound form a 3 to 8 membered heterocyclic ring optionally containing one or more further heteroatoms selected from nitrogen, oxygen and sulfur and optionally containing one or more double bonds;

L and M independently are a valence bond, —(CH$_2$)$_m$S(CH$_2$)$_n$—, —(CH$_2$)$_m$O(CH$_2$)$_n$—, —(CH$_2$)$_m$S(O)(CH$_2$)$_n$—, —(CH$_2$)$_m$S(O)$_2$(CH$_2$)$_n$—, —(CH$_2$)$_m$CH═CH(CH$_2$)$_n$—, —(CH$_2$)$_m$C≡C(CH$_2$)$_n$—, —(CH$_2$)$_m$CHR$^9$(CH$_2$)$_n$—, —(CH$_2$)$_m$NR$^9$(CH$_2$)$_n$—, —(CH$_2$)$_m$C(O)NR$^9$(CH$_2$)$_n$—, —(CH$_2$)$_m$C(O)O(CH$_2$)$_n$—, —S(CH$_2$)$_m$C(O)O(CH$_2$)$_n$—, —S(CH$_2$)$_m$C(O)NR$^9$(CH$_2$)$_n$—, —(CH$_2$)$_m$OC(O)(CH$_2$)$_n$—, —(CH$_2$)$_m$C(O)(CH$_2$)$_n$—, —(CH$_2$)$_m$C(NOR$^9$)(CH$_2$)$_n$—, —(CH$_2$)$_m$NR$^9$S(O)$_2$(CH$_2$)$_n$—, —(CH$_2$)$_m$S(O)$_2$NR$^9$(CH$_2$)$_n$—, —(CH$_2$)$_m$CHOR$^9$(CH$_2$)$_n$— or —(CH$_2$)$_m$P(O)(OR$^9$)O(CH$_2$)$_n$—;

wherein $R^9$ is hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl;

m and n independently are 0, 1, 2 or 3;

A and B independently are hydrogen, halogen, —CF$_3$, —CF$_2$CF$_3$, —CN, —NO$_2$, lower alkyl, lower alkenyl, lower alkynyl,

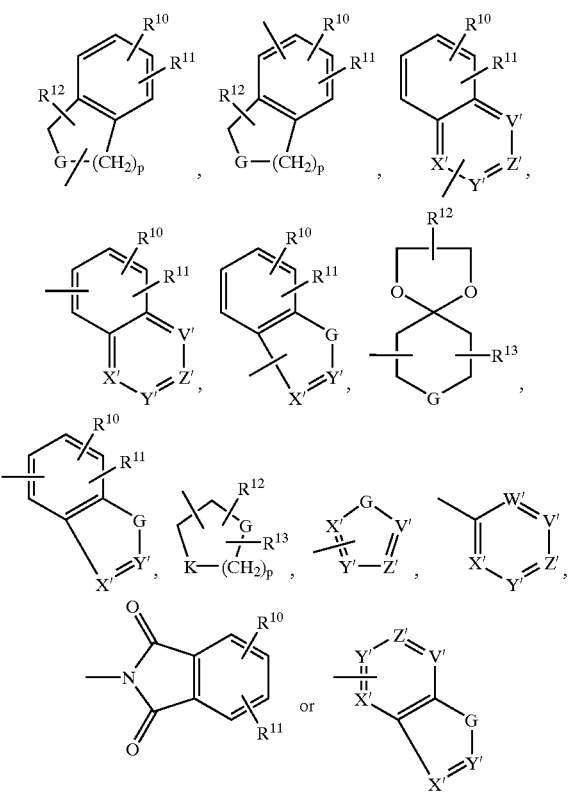

wherein
p is 1, 2 or 3;

X' is —N= or —CR$^{14}$=;
Y' is —N= or —CR$^{15}$=;
Z' is —N= or —CR$^{16}$=;
V' is —N= or —CR$^{17}$=;
W' is —N= or —CR$^{18}$=;
G is —NR$^{19}$—, —O— or —S—;
K is —NR$^{20}$—O— or —S—;
R$^{10}$, R$^{11}$, R$^{12}$, R$^{13}$, R$^{14}$, R$^{15}$, R$^{16}$, R$^{17}$ and R$^{18}$ independently are hydrogen, halogen, —CN, —CF$_3$, —OCF$_3$, —OCH$_2$CF$_3$, —OCF$_2$CHF$_2$, —NO$_2$, —OR$^{21}$, —NR$^{21}$R$^{22}$, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —SCF$_3$, —SR$^{21}$, —CHF$_2$, —OCHF$_2$, —OS(O)$_2$CF$_3$, —OS(O)$_2$R$^{21}$, —NR$^{21}$S(O)$_2$R$^{22}$, —S(O)$_2$NR$^{21}$R$^{22}$, —S(O)NR$^{21}$R$^{22}$, —S(O)$_2$R$^{21}$, —S(O)R$^{21}$, —(O) NR$^{21}$R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$ or —(O) OR$^{21}$, where R$^{12}$ and R$^{13}$ furthermore independently may represent oxo; or two of the groups R$^{10}$ to R$^{18}$ when defined in the same ring together may form a bridge —OCH$_2$O—;
wherein R$^{21}$ and R$^{22}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or R$^{21}$ and R$^{22}$ together with the nitrogen atom to which they are bound form a 3 to 8 membered heterocyclic ring optionally containing one or more further heteroatoms selected from nitrogen, oxygen and sulfur and optionally containing one or more double bonds;
R$^{19}$ and R$^{20}$ independently are hydrogen, —OR$^{23}$, —NR$^{23}$R$^{24}$, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl, —C(O)NR$^{23}$R$^2$1 or —C(O)OR$^{23}$;
wherein R$^{23}$ and R$^{24}$ independently are hydrogen, lower alkyl, lower alkenyl, lower alkynyl, cycloalkyl, cycloalkenyl, aryl, heterocyclyl, heteroaryl, cycloalkyl-lower alkyl, cycloalkyl-lower alkenyl, cycloalkyl-lower alkynyl, cycloalkenyl-lower alkyl, cycloalkenyl-lower alkenyl, cycloalkenyl-lower alkynyl, aryl-lower alkyl, aryl-lower alkenyl, aryl-lower alkynyl, heterocyclyl-lower alkyl, heterocyclyl-lower alkenyl, heterocyclyl-lower alkynyl, heteroaryl-lower alkyl, heteroaryl-lower alkenyl or heteroaryl-lower alkynyl; or R$^{23}$ and R$^{24}$ together with the nitrogen atom to which they are bound form a 3 to 8 membered heterocyclic ring optionally containing one or more further heteroatoms selected from nitrogen, oxygen and sulfur and optionally containing one or more double bonds;

with the provisos that
when L represents a group wherein n is 0, A is not halogen, —CF$_3$, —CN or —NO$_2$; and
when M represents a group wherein n is 0, B is not halogen, —CF$_3$, —CN or —NO$_2$;
as well as any optical or geometric isomer or tautomeric form thereof including mixtures of these or a pharmaceutically acceptable salt thereof.

The cycloalkyl, cycloalkenyl, heterocyclyl, aryl and heteroaryl ring systems defined in the above formulae (I'), (II') and (III') may optionally be substituted by one or more substituents, for example selected from the group consisting of halogen, lower alkyl, lower alkanoyl such as formyl, acetyl, propionyl, butyryl, valeryl, hexanoyl and the like, —OH, —CH$_2$OH, —NO$_2$, —CN, —CO$_2$H, —O-lower alkyl, aryl-lower alkyl, —CO$_2$CH$_3$, —CONH$_2$, —OCH$_2$CONH$_2$, —NH$_2$, —N(CH$_3$)$_2$, —CH$_2$N(CH$_3$)$_2$, —SO$_2$NH$_2$, —OCHF$_2$, —CF$_3$, —OCF$_3$ and the like. When the ring systems in question are substituted with more than one substituent the substituents may be the same or different. The above ring systems may also be substituted by two substituents forming a bridge, for example —OCH$_2$O— or —OCH$_2$CH$_2$O—.

The compounds according to the invention are preferably characterised by having a molecular weight of up to 1000, preferably of up to 600.

Preferably, the compounds according to the invention have an EC$_{50}$ value as determined by the method for determining the ability to stimulate cAMP formation in a cell line expressing the cloned human GLP-1 receptor disclosed in the following of less than 25 µM, such as of less than 10 µM, more preferred of less than 2 µM and even more preferred of less than 1 µM.

In a further aspect the invention relates to a non-peptide GLP-1 agonist which activates the human GLP-1 receptor. Agonist activity may eg be determined by the assays described in example 172.

Compounds may also be shown to be active by measuring insulin release from isolated human islets. This can be done according to the method disclosed in Eizirik D L, Korbutt G S, Hellerström C. Prolonged exposure of human pancreatic islets to high glucose concentrations in vitro impairs the beta-cell function. J. Clin. Invest. 90:1263–1268, 1992.

In a preferred embodiment the non-peptide GLP-1 agonist activates the human GLP-1 receptor without competing with GLP-1 in a competition binding assay.

This may be determined by measuring a compound that behaves as an agonist in the assays described in example 172 in a standard receptor binding assay. Plasma membranes may be used prepared as in example 172. Binding assays may be carried out in polypropylene tube. The buffer may be 25 mM HEPES, 0.1% BSA, pH 7.4. GLP-1 and test compounds may be dissolved and diluted as described in Example 172. Tracer (labelled GLP-1) may be prepared as described in (28). Tracer (30.000 cpm)+plasma membrane (0.5–2 µg) may be mixed with test compound and incubated at 37° C. for 1 hour. Non-specific binding may be determined with 10$^{-7}$ M GLP-1. Bound and unbound tracer may be separated by vacuum filtration. The filters can be counted in a γ-scintillation counter. The binding of the tracer in the absence of the test compounds and GLP-1 is set to 100%. A compound which does not compete with GLP-1 in a competition binding assay will not displace the tracer. Therefore, the tracer will display an unchanged binding of 100% in this assay whereas different concentrations of GLP-1 will compete with the tracer resulting in a decreased binding of the tracer in the range of between 0 and up to 100%.

In a further preferred embodiment the non-peptide GLP-1 agonist potentiates the binding of GLP-1 to the human GLP-1 receptor in a competition binding assay.

Such a potentiating effect may be demonstrated eg by the competition binding assay described above. Compounds that potentiate the binding will result in more than 100% tracer bound.

In a preferred embodiment the non-peptide GLP-1 agonist stabilises an active conformation of the human GLP-1 receptor different from the one(s) which GLP-1 stabilises.

This may be determined eg by performing a saturation experiment determining the affinity of GLP-1 with and without the presence of the compound in question. The saturation experiment is a standard receptor pharmacology experiment whereby the true affinity of a compound for a receptor can be measured (32). The protocol for the binding assay described above may be used except for that here the tracer is diluted and two sets of samples are measured, one with $10^{-6}$ M GLP-1 added (to determine non-specific binding) and one without (to determine total binding). The specific binding (total minus non-specific) is then plotted vs the concentration of tracer added. A curve fitting program (eg the saturation/scatchard template in GraphPad Prism®) may then determine the number of binding sites and the affinity. There may be more than one binding site with different affinities. When such an experiment is performed with GLP-1 one may observe one or two different binding sites dependent on the temperature at which the experiment is performed. It may be shown that the compounds in question stabilise a conformation different from that which GLP-1 normally stabilises by performing the saturation experiment described above in the presence of a high concentration of the compound in question. If the affinity of GLP-1 for the receptor is different when the compound is present, then the compound must stabilise a conformation of the receptor different from the one(s) which GLP-1 normally stabilises. This conformation is then characterised by having a different affinity for GLP-1.

The non-peptide GLP-1 agonists according to the invention may be either partial or full agonists.

In a further preferred embodiment the non-peptide GLP-1 agonist is a partial agonist.

Such partial agonists may be less likely of causing the receptor to desensiuse because they do not fully activate the receptor and therefore also do not fully activate the desensifisation signals.

Preferably, the non-peptide partial agonists have an $E_{max}$ of less than 90%, preferably less than 80% and more preferred in the range of 35 to 75% of that of GLP-1.

This may be determined eg by the assays described in example 172.

However, agonists of an $E_{max}$ of 90% or more as well as full agonists and agonists having an $E_{max}$ of more than 100% being efficient at lower dosages may also be usable. Thus, in another preferred embodiment the non-peptide GLP-1 agonist is a full agonist.

In still a further preferred embodiment the non-peptide GLP-1 agonist has at least a 10 fold selectivity towards the human GLP-1 receptor compared to the human glucagon receptor and/or the human GIP receptor. This may be determined eg by the assays described in example 172 using cells expressing the human glucagon receptor and/or the human GIP receptor and comparing the formation of cAMP with the amount obtained using the cells expressing the human GLP-1 receptor.

In another preferred embodiment the agonistic effect mediated by the non-peptide GLP-1 agonists can be antagonised by a GLP-1 antagonist.

This may be due to the fact that the non-peptide GLP-1 agonists bind to the same binding site as the GLP-1 antagonist.

An example of such a GLP-1 antagonist is 6-(2,5-dichlorobenzyl)-1-hydroxy-2-[2-(4-morpholinyl)ethyl]-1,6-dihydropyrrolo[3',4'5,6]pyrido[3,4-b]indol-3(2H)-one.

6-(2,5-Dichlorobenzyl)-1-hydroxy-2-[2-(4-morpholinyl)ethyl]-1,6-dihydropyrrolo[3',4',5,6]-pyrido[3,4-b]indol-3(2H)-one may be prepared according to the method below:

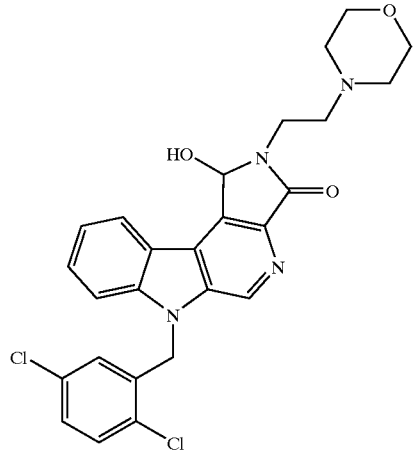

6-(2,5-Dichlorobenzyl)-1-hydroxy-2-[2-(4-morpholinyl)ethyl]-1,6-dihydropyrrolo[3',4',5,6]-pyrido[3,4-b]indol-3(2H)-one was prepared by a slight modification of a reported procedure (Dodd et al., *J Org. Chem.* 1993, 58, 7587): A solution of 9-(2,5-dichlorobenzyl)-N-[2-(4-morpholinyl)ethyl]-9H-β-carboline-3-carboxamide (400 mg, 0.83 mmol) in anhydrous tetrahydrofuran (12 ml) was stirred and cooled to −78° C. under nitrogen. When an internal temperature of −78° C. was attained, a 1.0 M methyl lithium in diethylether, cumene solution (4.2 mL, 4.2 mmol) was added by syringe over a period of 0.3 hours. The reaction mixture developed a very dark blue colour after complete addition of methyl lithium. The solution was stirred at −78° C. for 2 hours, and the dry ice-acetone bath was then replaced with an ice-water bath. After 0.5 hour, anhydrous DMF (3070 mg, 4.2 mmol) was added dropwise, and the reaction mixture was stirred at room temperature for another 15 hours. The solution was cooled to 0° C., and distilled water was slowly added while maintaining the internal temperature of the reaction mixture 0–5° C. The solution was concentrated to about 10 ml under reduced pressure, excess dichloromethane was added, and the mixture was washed with water. The organic phase was dried (Na$_2$SO$_4$), and the solvents were removed in vacuo.

The resulting crude residue was washed several times with ether. Purification of the crude material by column chromatography on silica with 4% 2M MH$_3$—CH$_3$OH in dichloromethane as eluent furnished the lactame (106 mg) as a pale yellow solid. A 241 mg portion (60%) of unreacted starting material was recovered by evaporating combined ether layers and chromatography fractions.

$^1$H NMR (CDCl$_3$) δ 8.76 (s, 1H), 8.48 (d, J=7.6 Hz, 1H), 7.66 (td, J=8.2 Hz, 0.91 Hz, 1H), 7.46 (t, J=7.4 Hz, 1H), 7.35–7.40 (4-line multiplet, 2H), 7.18 (dd, J=8.5 Hz, 2.4 Hz, 1H), 6.42 (d, J=2.3 Hz, 1H), 6.17 (s, 1H), 5.56(s, 2H), 4.46 (dt, J=9.6 Hz, 2.7 Hz, 1H), 3.83 (t, J=4.3 Hz, 4H), 3.47 (td, J=9.8 Hz, 1.5 Hz, 1H), 2.78–2.86 (m, 3H), 2.51–2.64 (m, 3H), 1.50–2.30 (v. br. s, 1H).

MS (APCI); (M+H)⁺ m/z 511.

In another embodiment of the invention the non-peptide agonists may activate the human receptor both in the absence of GLP-1 and in the presence of GLP-1 but only activate the rat GLP-1 receptor in the presence of GLP-1.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms which the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds which on administration undergo chemical conversion by metabolic processes before becoming active pharmacological substances. In general, such prodrugs will be functional derivatives of the compounds of the general formula (I) which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention activate the human GLP-1 receptor and are accordingly useful for the treatment and/or prevention of disorders and diseases in which such an activation is beneficial.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

Furthermore, the invention relates to the use of a compound according to the invention for the preparation of a pharmaceutical composition for the treatment and/or prevention of a disorder or disease wherein an activation of the human GLP-1 receptor is beneficial.

The invention also relates to a method for the treatment and/or prevention of disorders or diseases wherein an activation of the human GLP-1 receptor is beneficial the method comprising administering to a subject in need thereof an effective amount of a compound according to the invention.

Owing to the efficiency of the present compounds to activate the human GLP-1 receptor they are useful for the treatment and/or prevention of disorders and diseases, such as metabolic disorders, wherein an activation of the said receptor is beneficial. Accordingly, they may find use in the treatment and/or prevention of hyperglycaemia, dyslipidemia, Type 1 diabetes, Type 2 diabetes, hypertriglyceridemia, syndrome X, insulin resistance, IGT, obesity, diabetes as a consequence of obesity, diabetic dyslipidemia, hyperlipidemia, cardiovascular diseases and hypertension. Furthermore, they may find use in the treatment and/or prevention of appetite regulation and energy expenditure disorders such as eating disorders eg bulimia, and other conditions where a weight reduction is required. They may also find use in the treatment and/or prevention of anxiety, movement disorder, aggression, psychosis, seizures, panic attacks, hysteria or sleep disorders. A further application is for the inhibition of intestinal motility.

In a preferred embodiment of the invention the present compounds are used for the manufacture of a medicament for the treatment and/or prevention of hyperglycemia.

In yet a preferred embodiment of the invention the present compounds are used for the manufacture of a medicament for lowering blood glucose in a mammal.

In a preferred embodiment of the invention the present compounds are used for the preparation of a pharmaceutical composition for the treatment and/or prevention of IGT.

In another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In still a further embodiment of the invention the present compounds are used for the preparation of a pharmaceutical composition for the treatment and/or prevention of an appetite regulation or energy expenditure disorder.

In a further aspect of the invention the present compounds may be administered in combination with one or more further pharmacologically active substances eg selected from antidiabetics, antiobesity agents, antihypertensive agents and agents for the treatment and/or prevention of complications resulting from or associated with diabetes.

Suitable antidiabetics comprise insulin, GLP-1 derivatives such as those disclosed in WO 98/08871 to Novo Nordisk A/S which is incorporated herein by reference as well as orally active hypoglycaemic agents.

The orally active hypoglycaemic agents preferably comprise sulphonylureas, biguanides, meglitinides, oxadiazolidinediones, thiazolidinediones, glucosidase inhibitors, glucagon antagonists such as those disclosed in WO 99/01423 to Novo Nordisk A/S and Alanex Corporation, potassium channel openers such as those disclosed in WO 97/26265 and WO 99/03861 to Novo Nordisk A/S which are incorporated herein by reference, insulin sensitizers, DPP-IV inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents, compounds lowering food intake, PPAR and RXR agonists and agents acting on the ATP-dependent potassium channel of the β-cells.

In one embodiment of the invention the present compounds are administered in combination with insulin.

In a further embodiment the present compounds are administered in combination with a sulphonylurea eg tolbutamide, glibenclamide, glipizide or glicazide.

In another embodiment the present compounds are administered in combination with a biguanide eg metformin.

In yet another embodiment the present compounds are administered in combination with a meglitinide eg repaglinide.

In still another embodiment the present compounds are administered in combination with a thiazolidinedione eg troglitazone, ciglitazone, pioglitazone, rosiglitazone or the compounds disclosed in WO 97/41097 to Dr. Reddy's Research Foundation, such as 5-[[4-[(3,4-dihydro-3-methyl-4-oxo-2-quinazolinylmethoxy]phenyl]methyl]-2,4-thiazolidinedione.

Furthermore, the present compounds may be administered in combination with the insulin sensitizers disclosed in WO 99/19313 to Dr. Reddy's Research Foundation, such as 3-[4-[2-(phenoxazin-10-yl)ethoxy]phenyl]-2-ethoxypropanoic acid and 3-[4-[2-(phenoxazin-10-yl)ethoxy]phenyl]-2-ethoxypropanoic acid, sodium salt.

In a further embodiment the present compounds are administered in combination with an α-glucosidase inhibitor eg miglitol or acarbose.

In another embodiment the present compounds are administered in combination with an agent acting on the ATP-dependent potassium channel of the β-cells eg tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg in combination with a sulphonylurea and metformin, a sulphonylurea and acarbose, repaglinide and metformin, insulin and a sulphonylurea, insulin and metformin, insulin and troglitazone, insulin and lovastatin, etc.

Furthermore, the compounds according to the invention may be administered in combination with one or more antiobesity agents or appetite regulating agents.

Such agents may be selected from the group consisting of CART agonists, NPY antagonists, MC4 agonists, orexin antagonists, H3 antagonists, TNF agonists, CRF agonists, CRF BP antagonists, urocortin agonists, β3 agonists, MSH (melanocyte-stimulating hormone) agonists, MCH (melanocyte-concentrating hormone) antagonists, CCK agonists, serotonin re-uptake inhibitors, mixed serotonin and noradrenergic compounds, 5HT agonists, bombesin agonists, galanin antagonists, growth hormone, growth hormone releasing compounds, TRH agonists, uncoupling protein 2 or 3 modulators, leptin agonists, DA agonists (bromocriptin, doprexin), lipase/amylase inhibitors, PPAR modulators, RXR modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Furthermore, the present compounds may be administered in combination with one or more antihypertensive agents. Examples of antihypertensive agents are β-blockers such as alprenolol, atenolol, timolol, pindolol propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-n-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite | 1.0 mg |
| Magnesii stearas Ph. Eur. | q.s. |

Coating:

| | |
|---|---|
| HPMC approx. | 9 mg |
| Mywacett 9-40 T* approx. | 0.9 mg |

*Acylated monoglyceride used as plasticizer for film coating.

If desired, the pharmaceutical composition of the invention may comprise the compound of the formula (I) in combination with further pharmacologically active substances such as those described in the foregoing.

The present invention is further illustrated by the following representative examples which are, however, not intended to limit the scope of the invention in any way.

EXAMPLES

Abbreviations:
APCI: Atmospheric Pressure Chemical Ionisation
DMF: N,N-dimethylformamide
mCPBA: meta-chloroperoxybenzoic acid Some of the NMR data shown in the following are only selected data.

General procedure (A) for the preparation of 3-substituted 2-chloroquinoxalines:

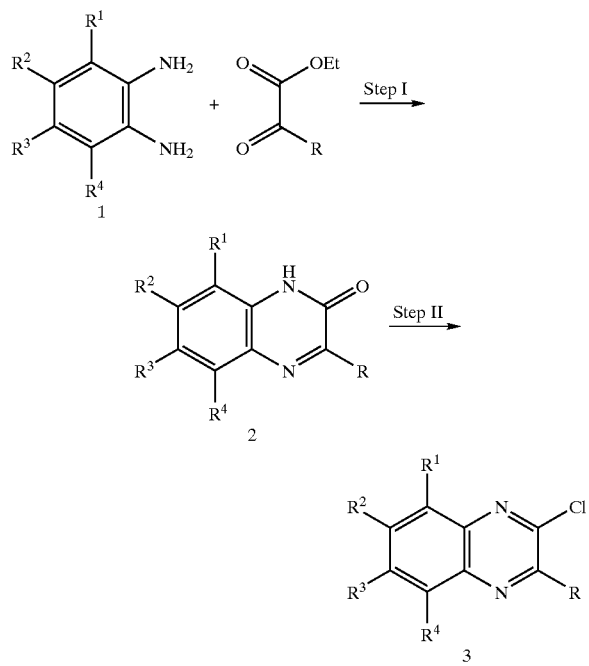

wherein $R^1$ to $R^4$ are as defined for formula (I) and R represents $CF_3$, $C_{1-6}$-alkyl, phenyl, phenyl-$C_{1-6}$-alkyl or 2-furanyl.

Step I:

The 1,2-diaminobenzene (1) (30.0 mmol, 1 equiv.) is dissolved in DMF (25 ml). Acetic acid (3.0 ml) is added followed by the appropriate α-ketoester (30.0 mmol, 1 equiv.). The solution is stirred at ambient temperature for 30 min. The reaction volume is reduced to one-third by evaporation in vacuo. Water (20 ml) is added, and the resulting suspension is chilled on an ice bath for 20 min. The precipitated 3-substituted quinoxaline-2-one (2) is collected by filtration, and dried in vacuo overnight.

Step II:

The 3-substituted quinoxaline-2-one (2) (18.0 g, 64.0 mmol) prepared in step I and a catalytic amount of 4-dimethylaminopyridine (0.50 g) is boiled in phosphoryl chloride (130 ml) for 4 hours. After cooling to room temperature, the mixture is poured slowly onto crushed ice (0.5 kg). The precipitate is collected by filtration and dried in vacuo overnight to obtain the 3-substituted 2-chloroquinoxaline (3).

The procedure was used for the preparation of the examples 15, 16 and 36–46.

The following compounds prepared by the general procedure. These compounds were used as starting materials for some of the other examples prepared.

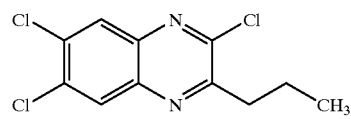

$^1$H NMR (CDCl$_3$): δ 1.0 (t, 3H), 1.81 (m, 2H), 3.05 (t, 2H), 8.05 (s, 1H), 8.12 (s, 1H);

MS (APCI positive): 275.0.

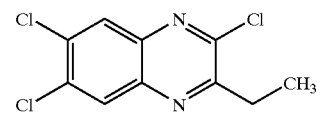

$^1$H NMR (CDCl$_3$): δ 1.35 (t, 3H), 3.11 (q, 2H), 8.17 (s, 1H), 8.03 (s, 1H).

MS (APCI positive): 261.7.

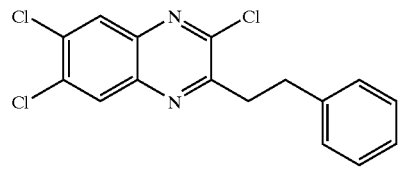

$^1$H NMR (CDCl$_3$): δ 3.2 (t, 2H), 3.5 (t, 2H), 7.3 (s, 5H), 8.1 (s, 1H), 8.2 (s, 1H).

MS (APCI positive): 335.0.

Furthermore, the procedure was used for the preparation of some of the other starting materials used in the examples including the starting material for example 91.

General procedure (B) for the synthesis of 3-substituted 2-mercaptoquinoxaline starting materials from 3-substituted 2-chloroquinoxalines illustrated by the preparation of the starting material for example 35:

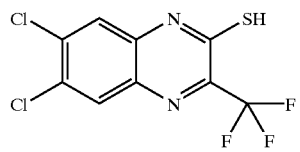

To a solution of 2,6,7-trichloro-3-trifluoromethylquinoxaline (300 mg, 1.0 mmol) in 3 ml of DMF was added NaSH.2H$_2$O (92 mg, 1.0 mmol). The solution turned wine-red color and was stirred at room temperature for 2 h. DMF was removed and the residue was added 5 ml of 10% HCl. EtOAc was added to extract the organic phase. Solvent was removed and the residue was purified by column chromatography to yield the corresponding mercapto product as a yellow solid (295 mg).

$^1$H NMR (acetone-d$_6$): δ 8.2 (s, 1H), 7.8 (s, 1H).

MS APCI (297).

The procedure was used for the preparation of some of the starting materials used in the examples including the starting materials for the examples 117, 130 and 115.

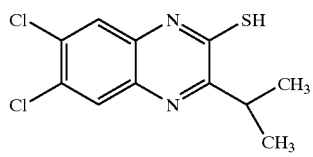

¹H NMR (CDCl₃): δ 1.2 (d, 6H), 4.0 (m, 1H), 7.6 (s, 1H), 8.0 (s, 1H), 14.3 (s, 1H).
MS (APCI positive): 273.0.

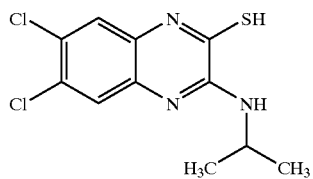

¹H NMR (CDCl₃): δ 1.8 (d, 6H), 4.43 (m, 1H), 8.25 (s, 1H), 8.32 (s, 1H).
MS (APCI positive): 288.0.

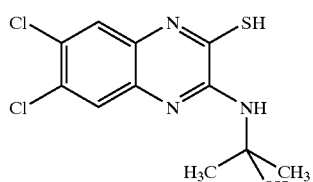

¹H NMR (CDCl₃) δ 1.49 (s, 9H), 7.32 (bs, 1H), 7.58 (s, 1H), 7.70 (s, 1H).
MS (APCI positive): 302.0.

General procedure (C) for the synthesis of 2,3-dichloroquinoxalines from 2,3-dihydroxyquinoxalines:

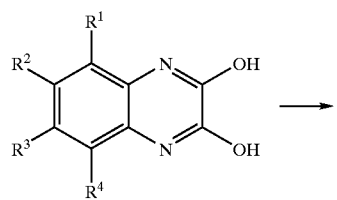

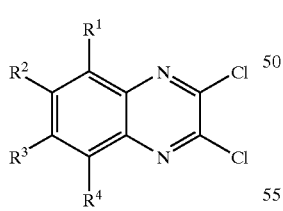

The corresponding 2,3-dihydroxyquinoxaline (4.0 mmol) was suspended in phosphorous oxychloride. About 6 ml of DMF was added to make it homogeneous and the reaction was heated at reflux overnight. The reaction was quenched by slowly pipetting into ice water. The aqueous mixture was then extracted twice with ethyl acetate. The organic layers were combined and concentrated in vacuo to a beige solid.

The procedure was used for the preparation of some of the starting materials used in the examples including the starting materials for the examples 133, 141, 139 and 134.

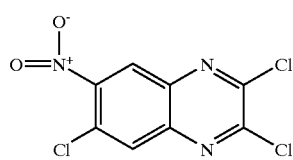

¹H NMR (CDCl₃): δ 8.18 (s, 1H), 8.45 (s, 1H).
MS (APCI negative): 276.9.

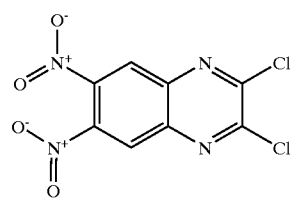

¹H NMR (DMSO-6): δ 8.96 (s, 2H).
MS (APCI positive): 289.9.

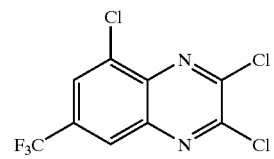

¹H NMR (DMSO-d₆): δ 8.36 (s, 1H), 8.41 (s, 1H).
MS (APCI positive): 301.9.

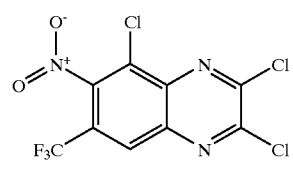

¹H NMR (CDCl₃): δ 8.34 (s, 1H).
MS (APCI positive): 346.9.

Example 1

6,7-Dichloro-2-isopropyl-3-(5-methyl-1,3,4-thiadiazol-2-ylsulfanyl)quinoxaline

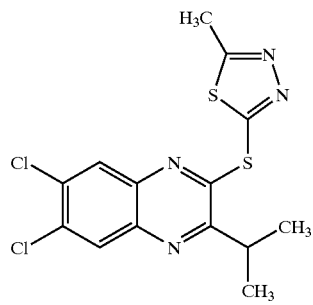

To a solution of 2,6,7-trichloro-3-isopropylquinoxaline (51 mg, 0.18 mmol) in DMF (4 ml) was added potassium fluoride 40% wt on alumina (80 mg, 0.55 mmol) followed by 2-mercapto-5-methyl-1,3,4-thiadiazole (26 mg, 0.20 mmol). The reaction mixture was stirred at room temperature overnight. The product was purified by flash column chromatography using ethyl acetate:hexanes 1:5 affording the title compound as a white solid.

$^1$H NMR (CDCl$_3$): δ 1.42 (d, 6H), 2.89 (s, 3H), 3.42 (m, 1H), 8.06 (s, 1H), 8.17 (s, 1H).

MS (APCI (M+H)$^+$) m/z 371.

Example 2

6,7-Dichloro-2-trifluoromethyl-3-(5-methyl-1,3,4-thiadiazol-2-ylsulfanyl)quinoxaline

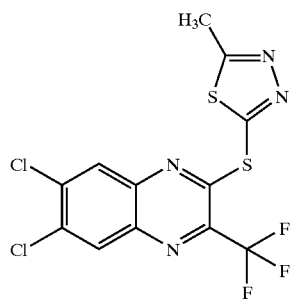

Using the same procedure as described in example 1 the title compound was obtained as a pale yellow solid.

$^1$H NMR (CDCl$_3$): δ 2.92 (s, 3H), 8.12 (s, 1H), 8.31 (s, 1H).

MS (APCI (M+H)$^+$) m/z 397.

Example 3

6,7-Dichloro-2-isopropyl-3-(4-amino-1,3,5-triazin-2-ylsulfanyl)quinoxaline

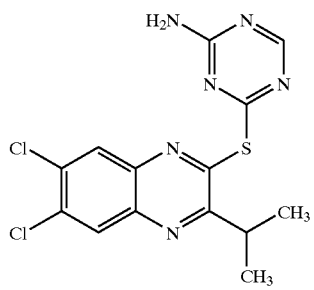

Using the same procedure as described in example 1 the title compound was obtained as a white solid.

$^1$H NMR (CDCl$_3$): δ 1.18 (d, 6H), 3.50 (m, 1H), 8.33 (s, 1H), 8.37 (s, 1H).

MS (APCI (M+H)$^+$) m/z 367.

Example 4

Bis-(6,7-dichloro-2-isopropylquinoxalin-3-yl)sulfide

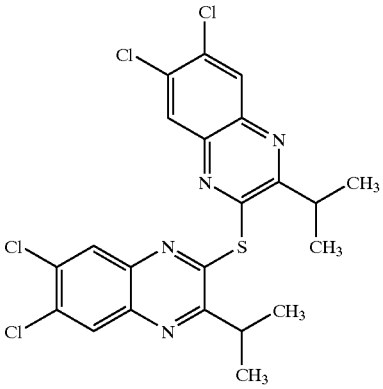

To a solution of 2,6,7-trichloro-3-isopropylquinoxaline (105 mg, 0.38 mmol) in DMF (3 ml) was added sodium hydrosulfide (21 mg, 0.23 mmol). The reaction mixture was stirred at 55–60° C. in an oil bath overnight. The product was purified by a plug filtration through silica gel using ethyl acetate:hexanes 1:20 followed by preparative thin layer chromatography using ethyl acetate:hexanes 1:60. Extraction of the product band using chloroform afforded the title compound as a white solid in 20% yield.

$^1$H NMR (CDCl$_3$): δ 1.40 (d, 12H), 3.53 (m, 2H), 7.86 (s, 2H), 8.20 (s, 2H).

MS (APCI (M+H)$^+$) m/z 511.

Example 5

6,7-Dichloro-2-(5-methyl-1,3,4-thiadiazol-2-ylsulfanyl)quinoxaline

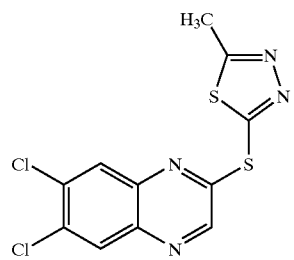

To a solution of 2,6,7-trichloroquinoxaline (60 mg, 0.26 mmol) in DMF (4 ml) was added potassium fluoride 40% wt on alumina (112 mg, 0.77 mmol), causing the burgundy solution to turn amber. 2-Mercapto-5-methyl-1,3,4-thiadizole (34 mg, 0.26 mmol) was added and the solution became reddish amber. The reaction was capped and stirred at room temperature overnight. The product was purified by flash column chromatography using ethyl acetate:hexanes (1:3) to afford the title compound.

$^1$H NMR (CDCl$_3$): δ 2.89 (s, 3H), 8.13 (s, 1H), 8.22 (s, 1H), 8.78 (s, 1H).

MS (APCI (M+H)$^+$) m/z 328.9.

Example 6

6,7-Dichloro-2-isopropyl-3-(5-methyl-1,3,4-thiadiazol-2-ylsulfinyl)quinoxaline

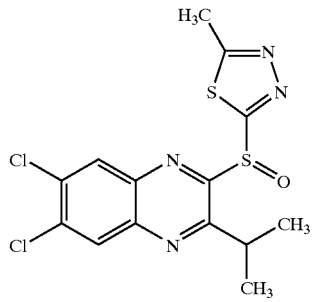

A solution of 6,7-dichloro-2-isopropyl-3-(5-methyl-1,3,4-thiadiazol-2-ylsulfanyl)quinoxaline (168 mg, 0.45 mmol) prepared as described in example 1 in dichloromethane (6 ml) was stirred in a dry ice/acetone bath at −78° C. while mCPBA (142 mg, 0.45 mmol) was added. After 8.5 hours, the reaction was quenched by addition of a saturated solution of sodium bi-carbonate. The layers were separated and the aqueous layer was extracted twice with chloroform. Evaporation of the solvent yielded a pale yellow solid. The product was purified by flash column chromatography using ethyl acetate:hexanes 1:3 to afford the title compound.

$^1$H NMR (CDCl$_3$): δ 1.38 (d, 3H), 1.45 (d, 3H), 2.82 (s, 3H), 3.84 (m, 1H), 8.26 (s, 1H), 8.36 (s, 1H).

MS (APCI (M+H)$^+$) m/z 386.9.

Example 7

6,7-Dichloro-2-isopropyl-3-(5-methyl-1,3,4-thiadiazol-2-ylsulfonyl)quinoxaline

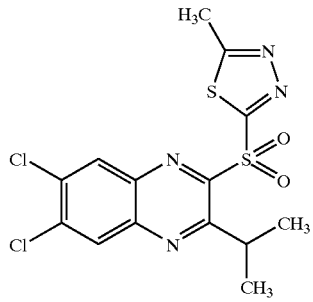

To a solution of 6,7-dichloro-2-isopropyl-3-(5-methyl-1,3,4-thiadiazol-2-ylsulfanyl)quinoxaline (110 mg, 0.30 mmol) in 1,2-dichloroethane was added mCPBA (209 mg, 0.59 mmol). After stirring overnight at room temperature, the reaction was quenched by addition of a saturated solution of sodium bicarbonate. After separating the layers, the aqueous layer was extracted twice with ethyl acetate. The organic layers were combined and concentrated under reduced pressure yielding a yellow solid. Purification by HPLC afforded the title compound as a white solid.

$^1$H NMR (CDCl$_3$): δ 1.48 (d, 6H), 2.99 (s, 3H), 4.21 (m, 1H), 8.01 (s, 1H), 8.28 (s, 1H).

MS (APCI (M+H)$^+$) m/z 403.

Example 8

6,7-Dichloro-2-isopropyl-3-(5-methylsulfanyl-1,3,4-thiadiazol-2-ylsulfanyl)-quinoxaline

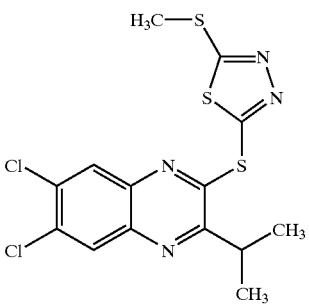

To a solution of 2,6,7-trichloro-3-isopropylquinoxaline (69 mg, 0.25 mmol) in DMF (4 ml) was added potassium fluoride 40% wt on alumina (109 mg, 0.75 mmol) followed by addition of 2-mercapto-5-methylsulfanyl-1,3,4-thiadiazole (44 mg, 0.26 mmol). The reaction was stirred overnight at room temperature. The product was purified by flash column chromatography using ethyl acetate:hexanes 1:20 to afford the title compound.

$^1$H NMR (CDCl$_3$): δ 1.43 (d, 6H), 2.87 (s, 3H), 3.41 (m, 1H), 8.09 (s, 1H), 8.18 (s, 1H).

MS (APCI (M+H)$^+$) m/z 403.4.

Example 9

6,7-Dichloro-2-isopropyl-3-(5-cyclopropylmethylsulfanyl-1,3,4-thiadiazol-2-ylsulfanyl)quinoxaline

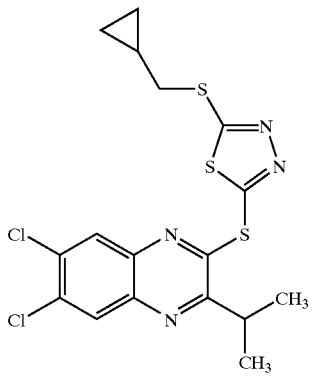

To a solution of 2,6,7-trichloro-3-isopropylquinoxaline (65 mg, 0.23 mmol) in DMF (4 ml) was added potassium fluoride 40% wt on alumina (103 mg, 0.71 mmol) followed by addition of 2-cyclopropylmethylsulfanyl-5-mercapto-1,3,4-thiadiazole (53 mg, 0.26 mmol). The reaction was stirred overnight at room temperature. The product was purified by flash column chromatography using ethyl acetate:hexanes 1:20 affording the title compound.

$^1$H NMR (CDCl$_3$): δ 0.39 (m, 2H), 0.68 (m, 2H), 1.31 (m, 1H), 1.43 (d, 6H), 3.37 (m, 3H), 8.10 (s, 1H), 8.18 (s, 1H).

MS (APCI (M+H)$^+$) m/z 442.9.

Example 10

6,7-Dichloro-2-isopropyl-3-(4-methyl-5-trifluoromethyl-4H-1,2,4-triazol-3-ylsulfanyl)-quinoxaline

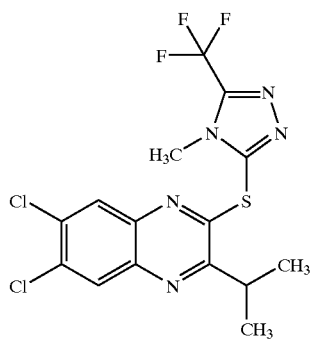

To a solution of 2,6,7-trichloro-3-isopropylquinoxaline (64 mg, 0.23 mmol) in DMF (4 ml) was added potassium fluoride 40% wt on alumina (1.1 mg, 0.70 mmol) followed by addition of 3-mercapto-5-trifluoromethyl-1,2,4-triazole (43 mg, 0.24 mmol). The reaction was stirred overnight at room temperature. Purification by flash column chromatography using ethyl acetate:hexanes 1:5 afforded 6,7-dichloro-2-isopropyl-3-(5-trifluoromethyl-4H-1,2,4-triazol-3-ylsulfanyl)quinoxaline in 83% yield.

To a solution of the above 6,7-dichloro-2-isopropyl-3-(5-trifluoromethyl-4H-1,2,4-triazol-3-ylsulfanyl)quinoxaline (78 mg, 0.19 mmol) in tetrahydrofuran (5 ml) was added triethylamine (0.05 ml, 0.38 mmol) followed by addition of iodomethane (0.02 ml, 0.29 mmol). The reaction was stirred under nitrogen overnight at room temperature. Purification by flash column chromatography using ethyl acetate:hexanes 1:10 afforded the title compound.

$^1$H NMR (CDCl$_3$): δ 1.45 (d, 6H), 3.37 (m, 1H), 4.03 (s, 3H), 7.78 (s, 1H), 8.15 (s, 1H).

MS (APCI (M+H)$^+$) m/z 422.

Example 11

5-[6,7-Dichloro-3-(1,4-dioxa-8-azaspiro[4,5]dec-8-yl)quinoxalin-2-ylmethylsulfanyl]4H-1,2,4-triazol-3-ylamine

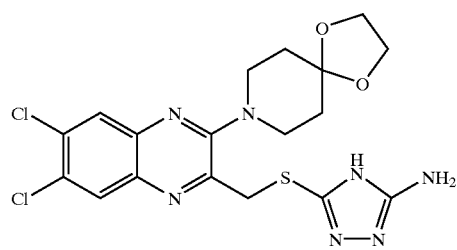

To a solution of 2,6,7-trichloro-3-chloromethylquinoxaline (107 mg, 0.38 mmol) in DMF (5 ml) was added 3-amino-5-mercapto-1,2,4-triazole (44 mg, 0.38 mmol) followed by addition of triethylamine (0.05 ml, 0.38 mmol). After 5 hours, potassium fluoride 40% wt on alumina (143 mg, 1.1 mmol) was added, followed by 1,4-dioxa-8-aza-spiro[4,5]decane (0.05 ml, 0.42 mmol). The reaction was stirred overnight at room temperature. Purification by flash column chromatography using ethyl acetate afforded the title compound.

$^1$H NMR (CDCl$_3$): δ 1.87 (m, 4H), 3.48 (m, 4H), 3.99 (s, 4H), 4.56 (s, 2H), 7.92 (s, 1H), 7.99 (s, 1H).

MS (APCI (M+H)$^+$) m/z 468.1.

Example 12

3-(6,7-Dichloro-3-isopropylquinoxalin-2-ylsulfanyl) propionic Acid Ethyl Ester

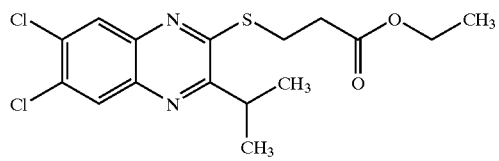

To a solution of 6,7-dichloro-3-isopropylquinoxaline-2-thiol (36 mg, 0.13 mmol) in DMF was added potassium carbonate (55 mg, 0.40 mmol) followed by ethyl 3-bromopropionate (0.02 ml, 0.16 mmol). The reaction was stirred at room temperature for 4 days. Purification by flash column chromatography using ethyl acetate:hexanes 1:40 afforded the title compound.

$^1$H NMR (CDCl$_3$): δ 1.27 (t, 3H), 1.34 (d, 6H), 2.82 (m, 2H), 3.37 (m, 1H), 3.52 (m, 2H), 4.20 (m, 2H), 8.00 (s, 1H), 8.09 (s, 1H).

MS (APCI (M+H)$^+$) m/z 373.

The following examples 13 to 17 are also useful as intermediates for the preparation of further compounds according to the invention.

Example 13

2,6,7-Trichloro-3-styrylquinoxaline

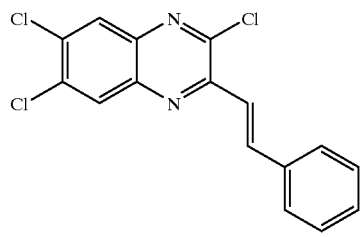

This compound was prepared according to the procedure described in Collins, J. L.; Dambek, P. J.; Goldstein, S. W.; Faraci, W. S. *Bioorg. Med. Chem. Lett.* 1992, 2, 915–8.

Example 14

2,6,7-Trichloro-3-[2-(4-fluorophenyl)vinyl]quinoxaline

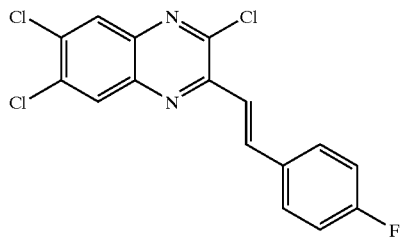

6,7-Dichloro-3-methyl-1H-quinoxalin-2-one (5 g, 22 mmol) (prepared as described in: Collins, J. L.; Dambek, P. J.; Goldstein, S. W.; Faraci, W. S. *Bioorg. Med. Chem. Lett.* 1992, 2, 915–8) was dissolved in a mixture of glacial acetic add (100 ml) and 98% sulfuric acid (10 ml). 4-Fluorobenzaldehyde (2.3 ml, 22 mmol) was added and the resulting mixture was stirred at reflux temperature for 3.5 hours. The mixture was allowed to cool to 85° C. and then poured onto ice (500 ml). The solid was filtered, washed with water and ethyl acetate and dried in vacuo at 30° C. overnight to afford 7.2 g (99%) of 6,7-dichloro-3-[2-(4-fluorophenyl)vinyl]-1H-quinoxalin-2-one.

$^1$H NMR (DMSO-d$_6$): δ 7.28 (t, 2H), 7.45 (s, 1H), 7.54 (d, 1H), 7.82 (dd, 2H), 8.00 (s, 1H), 8.07 (s, 1H), 12.6 (br s, 1H).

The above 6,7-dichloro-3-[2-(4-fluorophenyl)vinyl]-1H-quinoxalin-2-one (2.0 g, 6 mmol), 4-dimethylaminopyridine (0.2 g) and phosphorous oxychloride (POCl$_3$) were mixed and refluxed for 30 minutes. After cooling, the mixture was poured onto ice (500 ml). The solid was filtered, washed with water and dried in vacuo at 30° C. overnight to afford 1.8 g (83%) of the title compound.

$^1$H NMR (DMSO-d$_6$): δ 7.34 (t, 2H), 7.71 (d, 1H), 7.92 (dd, 2H), 8.05 (d, 1H), 8.40 (s, 1H), 8.45 (s, 1H).

Example 15

2,6,7-Trichloro-3-methylquinoxaline

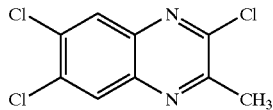

POCl$_3$ was added to 6,7-Dichloro-3-methyl-1H-quinoxalin-2-one (10 g, 44 mmol) and 4-dimethylaminopyridine (1 g) and the mixture was refluxed for 0.5 hours. After cooling, the mixture was poured onto ice (500 ml), filtered and washed with water to afford the title compound.

$^1$H NMR (DMSO-d$_6$): δ 2.79 (s, 3H), 8.25 (s, 1H), 8.28 (s, 1H).

Example 16

2-Chloro-6,7-difluoro-3-methylquinoxaline

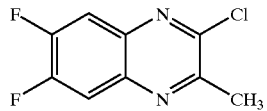

6,7-Difluoro-3-methyl-1H-quinoxalin-2-one (2 g, prepared from 4,5-difluoro-1,2-phenylene-diamine and pyruvic acid according to general procedure (A), step 1) was mixed with POCl$_3$ (20 ml) and 4-dimethylaminopyridine (10 mol %) and the mixture was refluxed for 2 hours. The mixture was allowed to cool and poured onto ice (300 ml), filtered and washed with water to afford the title compound.

$^1$H NMR (DMSO-d$_6$): δ 2.83 (s, 3H), 7.76 (m, 2H).

Example 17

2-Chloro-6,7-difluoro-3-styrylquinoxaline

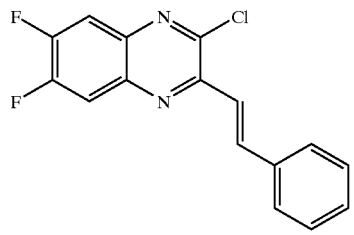

6,7-Difluoro-3-methyl-1H-quinoxalin-2-one (2 g, 10.2 mmol) was dissolved in a mixture of glacial acetic acid (40 ml) and 98% sulfuric acid (4 ml). Benzaldehyde (1.08 g, 10.2 mmol) was added and the resulting mixture was stirred at reflux temperature for 3.5 hours. The mixture was allowed to cool to 85° C. and then poured onto ice (400 ml). The solid was filtered, washed with water and ethyl acetate and dried in vacuo at 30° C. overnight to afford 2.5 g (88%) of 6,7-difluoro-3-styryl-1H-quinoxalin-2-one.

$^1$H NMR (DMSO-d$_6$): δ 7.20 (dd, 1H), 7.4–7.5 (m, 3H), 7.57 (d, 1H), 7.73 (d, 2H), 7.85 (dd, 1H), 8.04 (d, 1H), 12.6 (s, 1H).

The above 6,7-difluoro-3-styryl-1H-quinoxalin-2-one (2.65 g, 0.93 mmol) was mixed with 4-dimethylaminopyridine (0.27 g) and POCl$_3$ (27 ml) and the mixture was refluxed for 30 minutes. After cooling, the mixture was poured onto ice (400 ml) and the solid was filtered, washed with water (3×) and dried in vacuo overnight. Column chromatography on silica gel, eluting with ethyl acetate:heptane 1:20 afforded 1.6 g (56%) of the title compound.

$^1$H NMR (CDCl$_3$): δ 7.4–7.5 (m, 3H), 7.65–7.75 (m, 4H), 7.84 (dd, 1H), 8.08 (d, 1H).

Example 18

2,6,7-Trichloro-3-(1-methyl-1H-tetrazol-5-ylsulfanylmethyl)quinoxaline

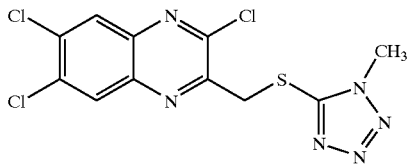

To a solution of 2,6,7-trichloro-3-chloromethylquinoxaline (500 mg, 1.78 mmol) in DMF (7 ml) was added 5-mercapto-1-methyltetrazole (206 mg, 1.78 mmol) followed by triethylamine (0.25 ml). The resulting dark reaction mixture was stirred at room temperature for 5 hours. Then it was partitioned between ethyl acetate and water. The organic layer was separated and concentrated to an oil. The oil was further purified by column chromatography (ethyl acetate:hexanes 1:2) to afford the title compound as a rusty powder.

$^1$H NMR (DMSO-$d_6$): δ 3.91 (s, 3H), 4.90 (s, 2H), 8.30 (s, 1H), 8.36 (s, 1H).

MS (APCI (M+H)$^+$) m/z 360.9.

Example 19

6,7-Dichloro-2-methanesulfonyl-3-trifluoromethylquinoxaline

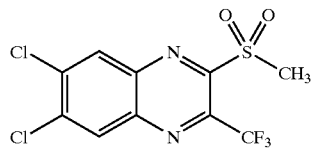

To a solution of 2,6,7-trichloro-3-trifluoromethylquinoxaline (64 mg, 0.2 mmol) in DMF (1 ml) was added methanesulfinic acid, sodium salt (43 mg, 0.4 mmol). The reaction mixture was stirred at room temperature overnight, then it was partitioned between ethyl acetate and water. The organic layer was separated and concentrated to an oil. This oil was further purified by column chromatography (ethyl acetate:hexanes 1:3) to yield the title compound as a white solid.

$^1$H NMR (CDCl$_3$): δ 3.54 (s, 3H), 8.40 (s, 1H), 8.48 (s, 1H).

MS (APCI positive) 344.9.

Example 20

6,7-Dichloro-2-trifluoromethyl-3-isopropylsulfonylquinoxaline

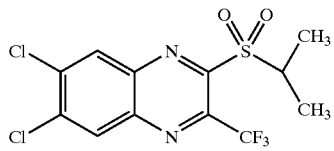

To a solution of 2,6,7-trichloro-3-trifluoromethylquinoxaline (74 mg, 0.25 mmole) in DMF (1 ml) was added isopropyl mercaptan followed by potassium carbonate. The reaction mixture was left at room temperature for 5 hours. Aqueous work-up afforded the desired sulfide as an oil. The oil was dissolved in 1,2-dichloroethane (2 ml). To this solution was added mCPBA (0.5 mmol). The reaction mixture was left at room temperature for 3 hours followed by aqueous work-up and column chromatography to yield the title compound as a white solid.

$^1$H NMR (CDCl$_3$): 1.48 (d, 6H), 4.35 (m, 1H), δ 8.39 (s, 1H), 8.47 (s, 1H).

MS (APCI (M+H)$^+$) m/z 372.9.

Example 21

5-(3,6,7-Trichloroquinoxalin-2-ylmethylsulfanyl)-1H-1,2,4-triazol-3-ylamine

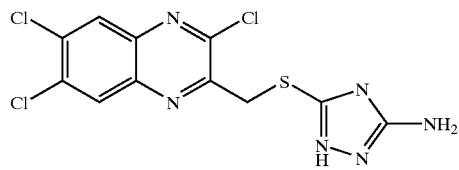

2,6,7-Trichloro-3-chloromethylquinoxaline (105 mg, 0.37 mmol) and 3-amino-5-mercapto-1,2,4-triazole (48 mg, 0.41 mmol) were dissolved in DMF (3 ml). Triethylamine (0.2 ml, 1.1 mmol) was added and the dark brown solution was allowed to stand at room temperature overnight. After evaporation of the solvent under reduced pressure, the residue was taken up in ethyl acetate and water. The layers were separated and the aqueous layer was extracted twice with ethyl acetate. The combined organic extracts were concentrated in vacuo, and the residue was purified by flash column chromatography using ethyl acetate to afford the title compound.

$^1$H NMR (MeOH-$d_4$): δ 4.61 (s, 2H), 8.17 (s, 2H).

MS (APCI (M+H)$^+$) m/z 360.9.

Example 22

6-Chloro-2-methyl-3-(5-methyl-1,3,4-thiadiazol-2-ylsulfanyl)quinoxaline

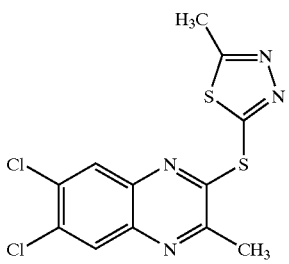

Step 1:

Ethyl pyruvate (4.2 ml, 39 mmol) was added to solution of 4-chloro-1,2-phenylenediamine (5.0 g, 35 mmol) in methanol (100 ml). The mixture was stirred at room temperature for 4 hours. The precipitate was filtered off, washed with methanol and dried to afford 4.95 g (73%) of a 6:4 mixture of 7-chloro-3-methyl-quinoxalin-2(1H)-one and 6-chloro-3-methyl-quinoxalin-2(1H)-one, respectively. A portion of this mixture (2.0 g, 10.28 mmol) was reacted with phenylphosphonic dichloride (4.0 g, 20.55 mmol) at 150° C. for 4 hours. The mixture was cooled, water (75 ml) was added and the pH was adjusted to 7 with aqueous ammonia. The precipitate was filtered off and washed with water. The product was purified by flash column chromatography using ethyl acetate:hexanes 1:9 affording 2,6-dichloro-3-methylquinoxaline and 3,6-dichloro-2-methylquinoxaline, respectively.

2,6-Dichloro-3-methylquinoxaline: Pale red solid M.p. 128–9° C. (Litt. M.p. 128–9° C.; Heterocycles 23(8), 2069–2074, 1985).

3,6-Dichloro-2-methylquinoxaline: Red solid M.p. 124–6° C. $^1$H NMR (CDCl$_3$): δ 2.85 (s, 3H), 7.69 (dd, 1H), 7.96 (d, 1H), 7.98 (d, 1H).

Step 2:

A mixture of 3,6-dichloro-2-methylquinoxaline (43 mg, 0.202 mmol), potassium carbonate (56 mg, 0.404 mmol) and 2-mercapto-5-methylthiadiazole (27 mg, 0.202 mmol) in acetone (3 ml) was stirred while caesium fluoride (37 mg, 0.242 mmol) and two drops of DMF were added. The mixture was stirred and heated at 50° C. overnight. The cooled mixture was filtered through decalite and the filtrate was evaporated. The residue was purified by flash column chromatography using ethyl acetate:toluene 1:9 to afford 29 mg (47%) of the title compound.

M.p. 194.5–196.5° C. $^1$H NMR (DMSO-d$_6$) δ 2.78 (s, 3H), 2.86 (s, 3H), 7.86 (dd, 1H). 8.08 (d, 1H), 8.17(d, 1H).

Example 23

6-Chloro-3-methyl-2-(5-methyl-1,3,4-thiadiazol-2-ylsulfanyl)quinoxaline

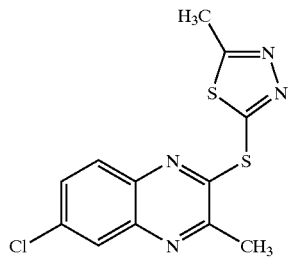

2,6-Dichloro-3-methylquinoxaline was reacted with 2-mercapto-S-methylthiadiazole in analogy with the method outlined in example 22, step 2 to yield 18 mg (42%) of the title compound as a pale red solid.

M.p. 189–90° C. $^1$H NMR (DMSO-d$_6$) δ 2.77 (s, 3H), 2.84 (s, 3H), 7.83 (dd, 1H), 8.07(d, 1H), 8.16 (d, 1H).

Example 24

6-Chloro-2-methoxy-3-(5-methyl-1,3,4-thiadiazol-2-ylsulfanyl)quinoxaline

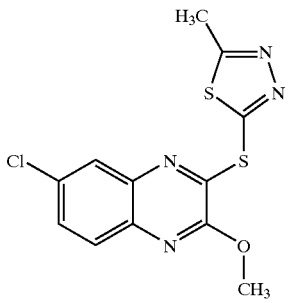

Step 1:
A suspension of 2,3,6-trichloroquinoxaline (J. Med. Chem. 33, 2240–54,1990) (5.84 g, 25 mmol) in dry methanol (70 ml) was stirred at 50° C. while methanolic sodium methoxide (30 mmol) (prepared from 0.7 g of sodium and 70 ml of dry methanol) was added over 5 hours. After the addition was complete, heating and stirring was continued for a further 16 hours. The mixture was cooled in an ice bath, the precipitate filtered off, washed with a small amount of methanol and dried to afford 4.28 g of a mixture consisting of 2,3-dimethoxy-6-chloroquinoxaline, 2,6-dichloro-3-methoxyquinoxaline and 3,6-dichloro-2-methoxyquinoxaline, respectively.

A 3 g portion of the latter mixture was purified by flash column chromatography using toluene:hexanes 7:3 as eluent yielding pure 3,6-dichloro-2-methoxyquinoxaline.

M.p. 113–4° C. (methanol). $^1$H NMR (CDCl$_3$): δ 4.18 (s, 3H), 7.54 (dd, 1H), 7.88 (d, 1H), 7.89 (d, 1H).

Step 2:
A mixture of 3,6-dichloro-2-methoxyquinoxaline (50 mg, 0.218 mmol), potassium carbonate (31 mg, 0.224 mmol) and 2-mercapto-5-methylthiadiazole (31 mg, 0.219 mmol) in 3 ml of acetone was stirred while adding caesium fluoride (40 mg, 0.262 mmol) and two drops of DMF. The mixture was stirred and heated at 55° C. for 16 hours. The cooled mixture was filtered and washed with acetone. The organic solution was evaporated and the residue was crystallised from methanol to afford 13 mg (18%) of the title compound as off white crystals.

M.p. 186–8° C. $^1$H NMR (CDCl$_3$): δ 2.90 (s, 3H), 4.20 (s, 3H), 7.52 (dd, 1H), 7.87 (d, 1H), 7.88 (d, 1H).

Example 25

2,6-Dichloroquinoline-3-carbaldehyde

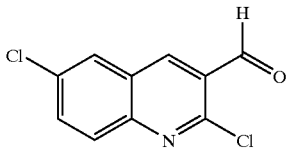

POCl$_3$ (31.1 g, 210 mmol) was added to DMF (6.5 g, 90 mmol) while keeping the temperature below 5° C. 4-Chloroacetanilide (5.07 g, 30 mmol) was added in one portion and the reaction mixture was heated to 75° C. for 4 hours. The reaction mixture was cooled to room temperature and poured onto ice. The separated crystals were filtered and dried. Yield 220 mg. M.p. 188-190° C.

Example 26

2,6,7-Trichloroquinoline-3-carbaldehyde

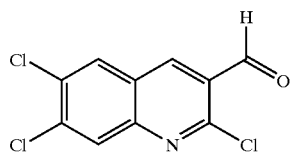

The title compound was prepared by the same method as described in example 25 starting from 3,4-dichloro-acetanilide. M.p. 190–1° C.

Example 27

2-Chloro-6-ethoxyquinoline-3-carbaldehyde

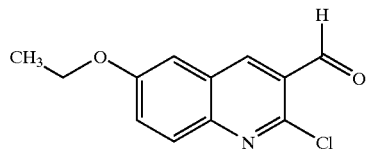

The title compound was prepared by the same method as described in example 25 starting from 4-ethoxy-acetanilide. M.p. 163–4° C.

Example 28

2-Chloro-6-ethoxyquinoline-3-carbaldehyde-O-methyl-oxime

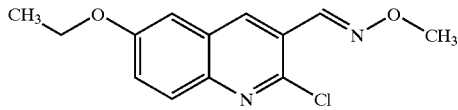

To a solution of 2-chloro-6-ethoxyquinoline-3-carbaldehyde (0.235 g, 1.0 mmol) in ethanol O-methylhydroxylamine hydrochloride (0.10 g, 1.1 mmol) was added. The reaction mixture was heated to reflux for 0.5 hours. After cooling to room temperature the precipitated compound was filtered and dried. Yield 180 mg. M.p. 142–4° C.

Example 29

6-Chloro-2-methylsulfanylquinoline-3-carbaldehyde

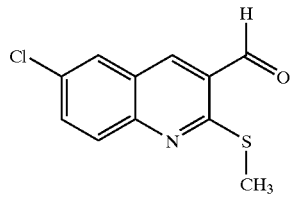

To a solution of 2,6-dichloroquinoline-3-carbaldehyde (113 mg, 0.5 mmol) in DMF (5 ml) sodium hydrosulfide nona-hydrate (105 mg, 1.5 mmol) and potassium carbonate (250 mg) were added. The reaction mixture was stirred at room temperature for 1 hour and methyl iodide (260 mg, 2.0 mmol) was added. Water was added and the separated compound was filtered off, dried and re-crystallised from ethanol. Yield 70 mg. M.p. 154–5° C.

Example 30

6-Ethoxy-2-methylsulfanylquinoline-3-carbaldehyde

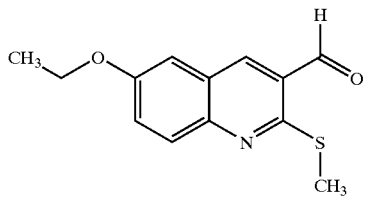

The title compound was prepared as described in example 29 starting from 2-chloro-6-ethoxyquinoline-3-carbaldehyde. M.p. 124–5° C.

Example 31

6,7-Dichloro-3-methylsulfonylquinoxaline-2-carboxylic Acid Ethyl Ester

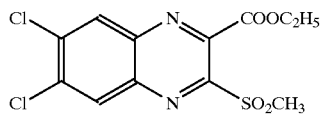

and

Example 32

6,7-Dichloro-3-methylsulfonylquinoxaline-2-carboxylic Acid Ethyl ester-$N^4$-oxide

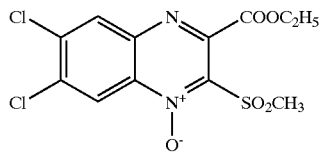

To a solution of ethyl 3,6,7-trichloroquinoxalinyl carboxylate (182 mg, 0.6 mmol) in DMF (2.5 ml) was added NaHS.2H$_2$O (110.4 mg, 1.2 mmol). The reaction mixture was stirred at room temperature for 3 hours and was partitioned in water and ethyl acetate. The organic layer was concentrated to a red solid. Without further purification, this red solid was re-dissolved in ethyl acetate (3 ml). A large excess of iodomethane (2 ml) was added to the above solution followed by a large excess of triethylamine (2 ml). The red colour instantly became yellowish. Then, the reaction mixture was washed with water once and concentrated to a yellow oil which was dissolved in dichloromethane (2 ml). To this was added mCPBA (440 mg, 47% pure, 1.2 mmol). The reaction mixture was stirred at room temperature for 2 hours and concentrated to a solid. This solid was purified by column chromatography with ethyl acetate:hexane (1:3) to yield a mixture of examples 31 and 32 in a ratio of 9:1 as a white solid. The two compounds were separated by HPLC.

EXAMPLE 31: $^1$H NMR (CDCl$_3$): δ 1.5 (t, 3H), 3.4 (s, 3H), 4.6 (q, 2H), 8.4 (s, 2H); MS (APCI positive) 349.

EXAMPLE 32: $^1$H NMR (CDCl$_3$): δ 1.5 (t, 3H), 3.6 (s, 3H), 4.5 (q, 2H), 8.2 (s, 1H), 8.4 (s, 1H); MS (APCI positive) 365.

Example 33

6,7-Dichloro-2-methyl-3-(isobutyl-1-sulfonyl)quinoxaline

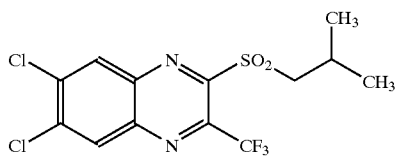

Using the same procedure as described in example 20, the title compound was synthesised as a white powder.

$^1$H NMR (CDCl$_3$): δ 1.2 (d, 6H), 2.5 (m, 1H), 3.6 (d, 2H), 8.4 (s, 1H), 8.5 (s 1H); MS (APCI positive) 387.

Example 34

Tert-butyl 2-{[6,7-dichloro-3-(trifluoromethyl)-2-quinoxalinyl]sulfonyl}ethylcarbamate

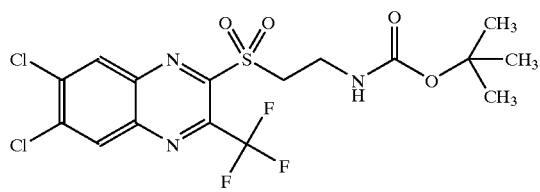

To a solution of 2,6,7-trichloro-3-trifluoromethylquinoxaline (100 mg, 0.33 mmol) in DMF (3 ml) was added one small scoop of potassium fluoride 40% wt on alumina followed by tertbutyl N-(2-mercaptoethyl)carbamate (0.06 ml, 0.37 mmol). The reaction mixture was stirred at room temperature overnight. The solvent was evaporated in vacuo and the residue was dissolved in ethyl acetate. Water was added, the layers were separated and the aqueous layer was extracted twice with ethyl acetate. After combining and concentrating the organic layers, the crude alkylation product was dissolved in 1,2-dichloroethane (5 ml), then mCPBA (574 mg, 1.32 mmol) was added and the mixture was stirred at room temperature overnight.

The reaction mixture was quenched by addition of a saturated solution of sodium bicarbonate. The layers were separated and the aqueous layer was extracted twice with 1,2-dichloroethane. The product was purified by flash column chromatography using ethyl acetate:hexane 1:5.

$^1$H NMR (CDCl$_3$): δ 0.39 (s, 9H), 3.80 (m, 2H), 3.99 (m, 2H), 5.20 (bs, 1H), 8.44 (s, 1H), 8.47 (s, 1H). MS (APCI negative) 472.9.

Example 35

2-{[2,4-Bis(trifluoromethyl)benzyl]sulfonyl}-6,7-dichloro-3-(trifluoromethyl)quinoxaline

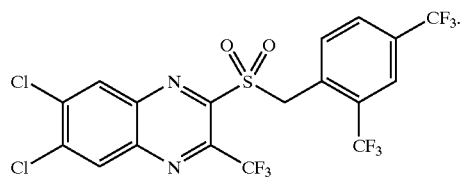

To a solution of 6,7-dichloro-3-trifluoromethyl-2-mercaptoquinoxaline (35 mg, 0.12 mmol) in DMF (2.5 ml) was added a small scoop of potassium carbonate followed by 2,4-bis(trifluoromethyl)benzyl bromide (0.04 ml, 0.13 mmol). The reaction mixture was stirred at room temperature for 5 hours. The solvent was evaporated in vacuo, the residue was dissolved in ethyl acetate and water was added. The layers were separated and the aqueous layer was extracted twice with ethyl acetate. The combined organic layers were concentrated under reduced pressure to a pale yellow solid. The crude alkylation product was dissolved in 1,2-dichloroethane to which was added mCPBA (1.1 g, 1.3 mmol). The oxidation reaction was stirred at room temperature overnight. The reaction was quenched by addition of a saturated solution of sodium bicarbonate. The layers were separated and the aqueous layer was extracted twice with 1,2-dichloroethane. The combined organic layers were concentrated under reduced pressure to a pale yellow solid. The product was purified by HPLC.

$^1$H NMR (CDCl$_3$): δ 5.29 (s, 2H), 7.89 (m, 1H), 8.01 (m, 2H), 8.39 (s, 1H), 8.50 (s, 1H). MS (APCI negative) 555.8.

Example 36

2,6,7-Trichloro-3-isopropylquinoxaline

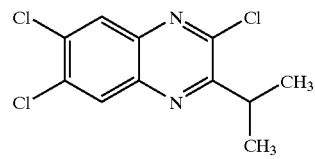

The title compound was prepared according to the general procedure (A).

$^1$H NMR (CDCl$_3$): δ 8.2 (s, 1H), 8.1 (s, 1H), 3.7 (m, 1H), 1.4 (d, 6H).

MS APCI (275).

Example 37

2,6,7-Trichloro-3-benzylquinoxaline

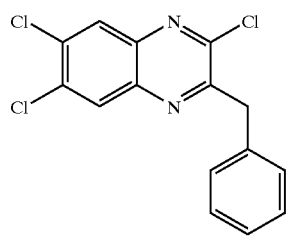

The title compound was prepared according to the general procedure (A).

$^1$H NMR (CDCl$_3$): δ 8.0 (s, 1H), 7.9 (s, 1H), 7.2 (m, 5H), 4.3 (s, 2H).

MS APCI (323.5).

Example 38

2,6,7-Trichloro-3-(furan-2-yl)quinoxaline

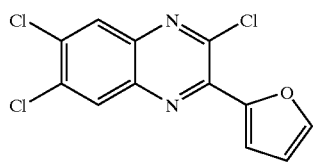

The title compound was prepared according to the general procedure (A).

$^1$H NMR (CDCl$_3$) δ 8.3 (s, 1H), 8.0 (s, 1H), 7.7 (m, 1H), 7.6 (m, 1H), 6.6 (m, 1H).

MS APCI (301).

Example 39

2,6,7-Trichloro-3-phenylquinoxaline

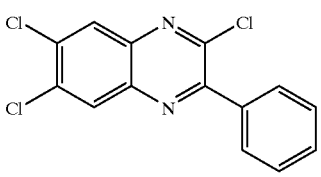

The title compound was prepared according to the general procedure (A).

$^1$H NMR (CDCl$_3$): δ 8.2 (s, 1H), 8.1 (s, 1H), 7.8 (m, 2H), 7.5 (m, 3H).

MS APCI (309).

Example 40

2,6,7-Trichloroquinoxaline

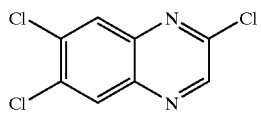

The title compound was prepared according to the general procedure (A).

$^1$H NMR (CDCl$_3$): δ 8.7 (s, 1H), 8.2 (s, 1H), 8.1 (s, 1H).

GCMS (232).

Example 41

2,6,7-Trichloro-3-chloromethylquinoxaline

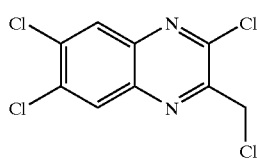

The title compound was prepared according to the general procedure (A).

$^1$H NMR (DMSO-d$_6$): δ 8.6 (s, 1H), 8.5 (s, 1H), 5.1 (s, 2H).

Example 42

2,6,7-Trichloro-3-ethoxycarbonylquinoxaline

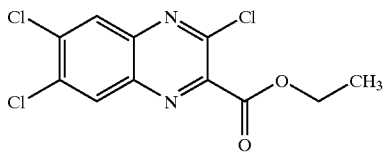

The title compound was prepared according to the general procedure (A).

$^1$H NMR (CDCl$_3$): δ 8.3 (s, 1H), 8.1 (s, 1H), 4.5 (q, 2H), 1.4 (t, 3H).

MS (305.1).

Example 43

2,6,7-Trichloro-3-trifluoromethylquinoxaline

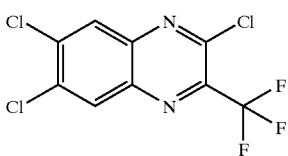

The title compound was prepared according to the general procedure (A).

$^1$H NMR (CDCl$_3$): δ 8.4 (s, 1H), 8.2 (s, 1H).

MS APCI (300).

Example 44

2-Chloro-3-isopropylquinoxaline

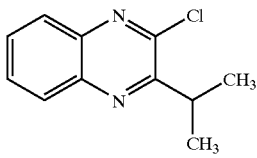

The title compound was prepared according to the general procedure (A).

$^1$H NMR (CDCl$_3$): δ 8.1 (d, 1H), 8.0 (d, 1H), 7.8 (m, 2H), 3.7 (m, 1H), 1.5 (d, 6H).

GCMS (204.6).

Example 45

2-Chloro-6,7-methoxy-3-phenylquinoxaline

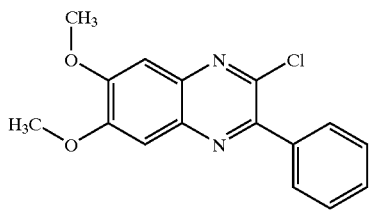

The title compound was prepared according to the general procedure (A).

$^1$H NMR (CDCl$_3$): δ 7.9 (m, 2H), 7.5 (m, 3H), 7.4 (s, 1H), 7.3 (s, 1H), 4.1 (d, 6H).

MS APCI (301.6).

Example 46

2,6-Dichloro-3-methylquinoxaline

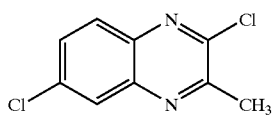

The title compound was prepared according to the general procedure (A).

Example 47

2,7-Dichloro-3-methoxyquinoxaline

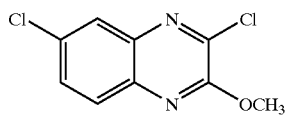

The title compound was prepared using the first step of example 24.

Example 48

2,6,7-Trichloro-3-[(4-amino-1H-pyrazolo[f3,4-d]-pyrimidin-3-ylsulfanyl)methyl]quinoxaline

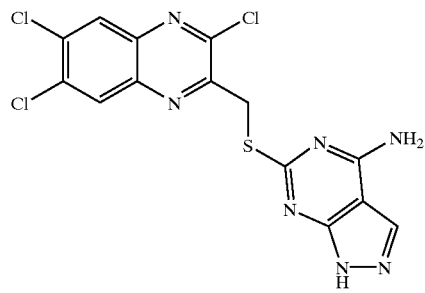

The title compound was prepared according to example 18 using 4-amino-1H-pyrazolo[3,4-d]pyrimidine-6-thiol.

$^1$H NMR (DMSO-d$_6$): δ 13.27 (b, 1H), 8.43 (s, 1H), 8.42 (s, 1H), 7.97 (s, 1H), 7.50 (b, 2H), 4.87 (s, 2H).

MS (412).

Example 49

2,6,7-Trichloro-3-[(1-phenyl-1H-tetrazol-5-yl)sulfanyl)methyl]quinoxaline

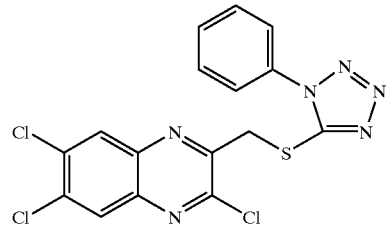

The title compound was prepared according example 18 using 1-phenyl-1H-tetrazole-5-thiol.

$^1$H NMR (DMSO-d$_6$): δ 8.44 (s, 1H), 8.42 (s, 1H), 7.67 (m, 5H), 5.07 (s, 2H).

MS APCI (423).

Example 50

6,7-Dichloro-3-isopropyl-2-(5-amino-1,3,4-thiadiazol-2-yl)sulfanylquinoxaline

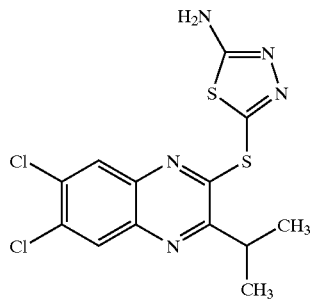

The title compound was prepared using the procedure described in example 1.

$^1$H NMR (MeOH-d$_4$): δ 8.1 (s, 1H), 7.9 (s, 1H), 3.3 (m, 1H), 1.4 (s, 6H).

MS (372.3).

Example 51

6,7-Dichloro-3-isopropyl-2-(5-cyclopropylmethylcarbonylamino-1,3,4-thiadiazol-2-yl)sulfanylquinoxaline

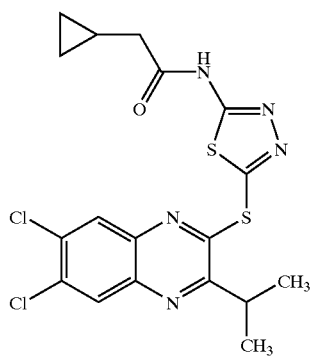

The title compound was prepared using the procedure described in example 1.

¹H NMR (CDCl₃): δ 12.7 (b, 1H), 8.1 (s, 1H), 8.0 (s, 1H), 3.45 (m, 1H), 2.05 (m, 1H), 1.5 (d, 6H), 1.2 (m, 2H), 1.0 (m, 2H).

MS APCI (440).

Example 52

7-Chloro-3-methoxy-2-(5-methyl-1,3,4-thiadiazol-2-yl)sulfanylquinoxaline

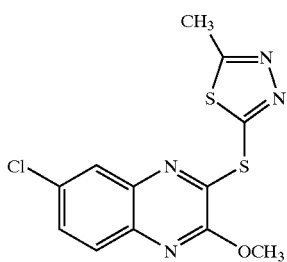

The title compound was prepared using the procedure described in example 1 using the product of example 47.

Example 53

6,7-Dichloro-3-isopropyl-2-(5-amino-1,3,4-triazol-2-yl)sulfanylquinoxaline

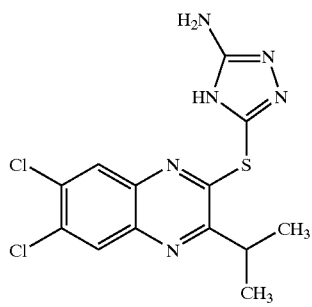

The title compound was prepared using the procedure described in example 1.

¹H NMR (DMSO-d₆): δ 12.7 (b, 1H), 8.35 (s, 1H), 8.05 (s, 1H), 6.3 (b, 2H), 3.5 (m, 1H), 1.4 (d, 6H).

MS (355).

Example 54

6,7-Dichloro-3-isopropyl-2-(3-chloro-5-triflouromethyl-2-pyridyl)sulfanylquinoxaline

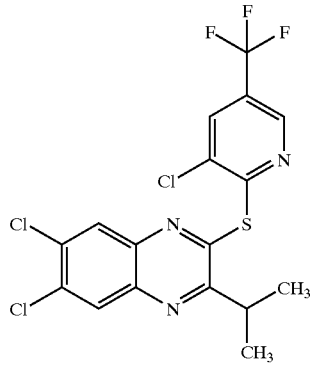

The title compound was prepared using the procedure described in example 1.

¹H NMR (CDCl₃): δ 8.5 (s, 1H), 8.2 (s, 1H), 8.0 (m, 2H), 3.5 (m, 1H), 1.4 (d, 6H).

MS (452).

Example 55

6,7-Dichloro-3-triflouromethyl-2-(5-methyl-1,3,4-thiadiazol-2-yl)sulfinylquinoxaline

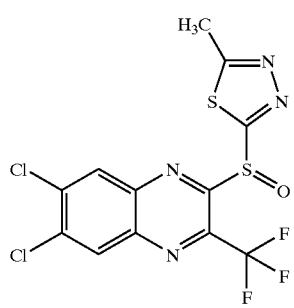

The title compound was prepared using the procedure described in example 6.

Example 56

6,7-Dichloro-3-methyl-2-(methylsulfonyl)quinoxaline

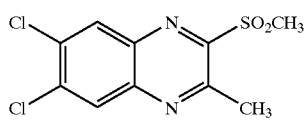

The title compound was prepared using the procedure described in example 19.

Example 57

(6,7-Dichloro-3(2-furanyl)quinoxalin-2yl)-2-propynylamine

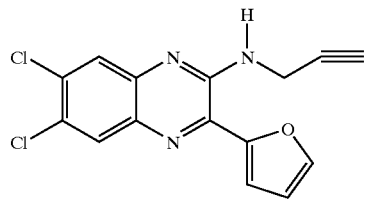

To a mixture of the compound prepared in example 38 (1.0 mmol) and propargylamine (1.0 mmol) in 4 ml of DMF was added caesium carbonate. The resulting mixture was stirred at room temperature overnight. DMF was removed in vacuo and the oily residue was purified by column chromatography to afford the title compound.

$^1$H NMR (DMSO-$d_6$): δ 8.07 (s, 1H), 8.05 (s, 1H), 7.87 (s, 1H), 7.79 (t, 1H), 7.41 (d, 1H), 6.83 (m, 1H), 4.31 (m, 2H), 3.08 (s, 1H); MS (318).

Example 58

(6,7-Dichloro-3-(2-furanyl)quinoxalin-2-yl)-2-hydroxyethylamine

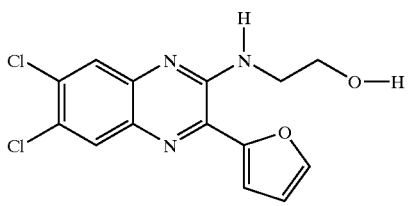

The compound was prepared using the same procedure as described for example 57 using ethanol amine instead of propargylamine.

$^1$H NMR (DMSO-$d_6$): δ 8.06 (s, 1H), 8.02 (s, 1H), 7.80 (s, 1H), 7.43 (d, 2H), 6.82 (m, 1H), 4.91 (b, 1H), 3.66 (m, 4H).

MS APCI (324).

Example 59

(6,7-Dichloro-3-methylsulfonylquinoxalin-2-yl) amine

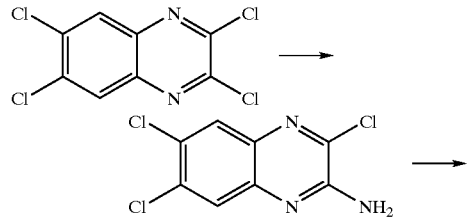

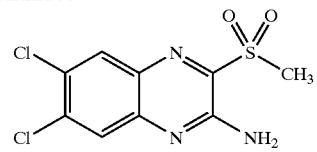

Dry ammonia gas was bubbled through a solution of tetrachloroquinoxaline (260 mg, 0.97 mmol) in dry DMF (20 ml), while stirring at 0° C. After 20 minutes, the reaction was allowed to warm to room temperature and bubbling was continued for an additional 15 minutes. The reaction mixture was then concentrated to dryness in vacuo. To a suspension of the resulting 2,6,7-trichloro-3-aminoquinoxaline in DMF was added methanesulfinic acid sodium salt (230 mg, 2.2 mmol). The reaction was stirred overnight at room temperature. After removing the solvent in vacuo, the residue was taken up in ethyl acetate and water. The layers were separated and the aqueous layer was extracted twice with ethyl acetate. The organic layers were combined and evaporated in vacuo. (6,7-Dichloro-3-methylsulfonylquinoxalin-2-yl) amine was purified by flash column chromatography using ethyl acetate:hexane 1:3 to obtain a yellow solid.

$^1$H NMR (CDCl$_3$): δ 3.43 (s, 3H), 6.14 (brd s, 2H), 7.81 (s, 1H), 8.05 (s, 1H).

MS (APCI positive) 291.9.

Example 60

2-Bromo-6,7-dichloro-3-trifluoromethylquinoxaline

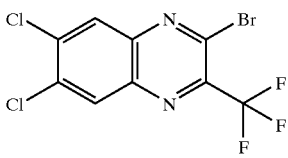

6,7-Dichloro-3-trifluoromethyl-1H-quinoxalin-2-one (500 mg, 1.8 mmol) was dissolved in phosphorus tribromide (2.0 ml), and the solution was heated at 140° C. for 16 hours. The reaction mixture was cooled to room temperature, before it was poured out on ice (100 g) and extracted with dichloromethane. The organic phase was separated and dried with anhydrous sodium sulphate, then taken to dryness by rotary evaporation to leave a pale brown powder.

Further purification using column chromatography and ethyl acetate:heptane (1:1) as eluent gave the title compound as a white powder. Yield: 295 mg (47%).

$^1$H-NMR (CDCl$_3$): δ 8.25 (s, 1H); 8.35 (s, 1H).

Anal. (calc. %; found %): C (31.25; 31.32); H (0.58; 0.61); N (8.10; 7.67).

Example 61

6,7-Dichloro-2-methylsulfonyl-3-styrylquinoxaline

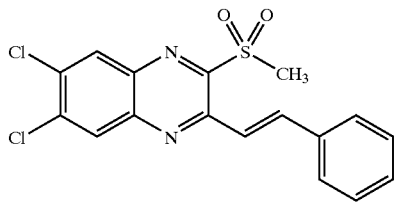

Using the same procedure as for the synthesis of example 19, the title compound was synthesised as a yellowish solid.

$^1$H NMR (CDCl$_3$): δ 3.54 (s, 3H), 7.42 (m, 3H), 7.72 (m, 2H), 8.05 (d, 1H), 8.20 (d, 1H), 8.19 (s, 1H), 8.28 (s, 1H).

MS (APCI positive) 379.

Example 62

6,7-Dichloro-2-methylsulfonyl-3-(methylsulfonyl)methyl-quinoxaline

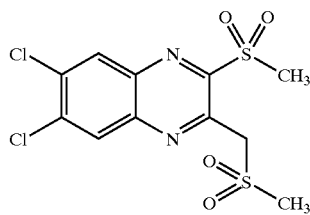

To a solution of 3-chloromethyl-2,6,7-trichloroquinoxaline (150 mg, 0.53 mmol) in DMF (3 ml) was added methanesulfinic acid, sodium salt (120 mg, 1.06 mmol). The reaction mixture was stirred at room temperature overnight. The solvent was removed and the residue was purified by column chromatography (ethyl acetate:hexane 1:2) to afford the title compounds as a white solid.

$^1$H NMR (CD$_3$CN) δ 3.14 (s, 3H), 3.47 (s, 3H), 5.30 (s, 2H), 8.30 (S, 2H).

MS (APCI positive) 369.

Example 63

6,7-Dichloro-2-isopropyl-3-(4-methylthiazol-2-ylsulfonyl)quinoxaline

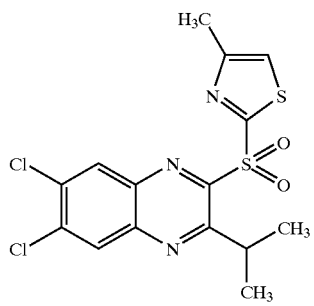

and

Example 64

6,7-Dichloro-2-isopropyl-3-(4-methylthiazol-2-ylsulfinyl)quinoxaline

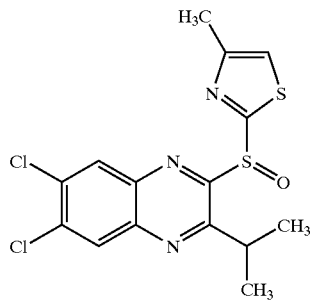

To a solution of 3-isopropyl-2,6,7-trichloroquinoxaline (100 mg, 0.364 mmol) in DMF (3 ml) was added 4-methylthiazole-2-thiol (45 mg, 0.38 mmol) followed by potassium carbonate (106 mg, 0.728 mmol). After stirring at room temperature for 5 hours, the reaction mixture was partitioned between water and ethyl acetate. The organic layer was separated and the aqueous layer was extracted with ethyl acetate one more time. The combined organic layers were concentrated to dryness. This residue was dissolved in dichloromethane (3 ml). To this solution was added mCPBA (157 mg, 0.73 mmol, 79% pure). The reaction mixture was stirred overnight at room temperature. The reaction was quenched by addition of a saturated solution of sodium bicarbonate. After separating the layers, the aqueous layer was extracted twice with ethyl acetate. The organic layers were combined and concentrated under reduced pressure yielding a white solid. This solid was further purified by column chromatography affording two components as a white solid.

EXAMPLE 63: $^1$H NMR (CD$_3$CN) δ 1.38 (d, 6H), 2.49 (s, 3H), 4.22 (m, 1H), 7.71 (s, 1H), 8.11 (s, 1H), 8.27 (s, 1H). MS (APCI positive) 402.

EXAMPLE 64: $^1$H NMR (CDCl$_3$): δ 1.37 (d, 3H), 1.39 (d, 3H), 2.42 (s, 3H), 3.91 (m, 1H), 7.19 (s, 1H), 8.24 (s, 1H), 8.37 (s, 1H). MS (APCI positive) 386.

Example 65

6,7-Dichloro-2-isopropyl-3-(1-methyl-1H-imidazol-5-ylsulfonyl)quinoxaline

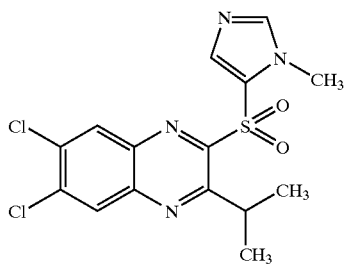

Using the same procedure as outlined in example 63, the title compound was obtained as a white solid.

$^1$H NMR (CDCl$_3$): δ 1.45 (d, 6H), 4.02 (s, 3H), 4.24 (m, 1H), 7.22 (s, 1H), 7.30 (s, 1H), 7.94 (s, 1H), 8.25 (s, 1H). MS (APCI positive) 385.

Example 66

6,7-Dichloro-2-isopropyl-3-(isopropyl-2-sulfonyl) quinoxaline

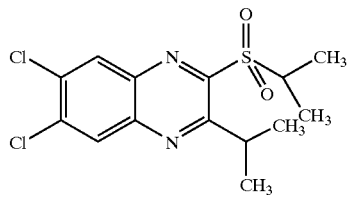

and

Example 67

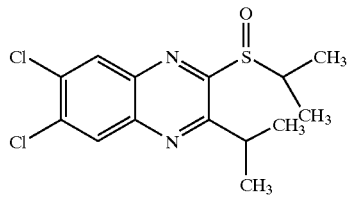

Using the same procedure as for the synthesis of examples 63 and 64, the title compounds were synthesised as white solids.

EXAMPLE 66: $^1$H NMR (CDCl$_3$): δ 1.43 (d, 6H), 1.51 (d, 6H), 4.20 (m, 1H), 4.38 (m, 1H), 8.18 (s, 1H), 8.25 (s, 1H). MS (APCI positive) 347.

EXAMPLE 67: $^1$H NMR (CDCl$_3$): δ 1.25 (d, 3H), 1.41 (m, 9H), 3.48 (m, 1H), 3.72 (m, 1H), 8.25 (s, 1H), 8.35 (s, 1H). MS (APCI positive) 331.

Example 68

6,7-Dichloro-2-isopropyl-3-(methylsulfonyl) quinoxaline

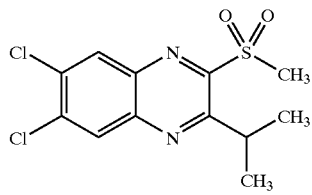

and

Example 69

6,7-Dichloro-2-isopropyl-3-(methylsulfinyl) quinoxaline

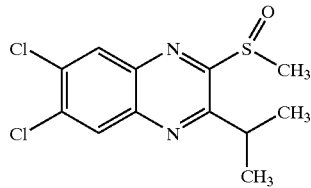

To a solution of 3-isopropyl-6,7-dichloroquinoxaline-2-thiol (110 mg, 0.40 mmol) in DMF (5 ml) was added iodomethane (0.5 ml, large excess) followed by potassium carbonate. The reaction mixture was stirred at room temperature for 10 min. The solvent was removed under reduced pressure and the residue was partitioned between water and ethyl acetate. The organic layer was separated and concentrated to dryness. The residue was re-dissolved in dichloromethane (5 ml) and mCPBA (215 mg, 0.6 mmol, 47% pure) was added. The reaction mixture was stirred for 2 hours at room temperature. The reaction was quenched by addition of a saturated solution of sodium bicarbonate. After separating the layers, the aqueous layer was extracted twice with ethyl acetate. The combined organic layers were concentrated under reduced pressure yielding a white solid. The solid was further purified by column chromatography affording two components as a white solid.

EXAMPLE 68: $^1$H NMR (CDCl$_3$): δ 1.43 (d, 6H), 3.51 (s, 3H), 4.10 (m, 1H), 8.20 (s, 1H), 8.28 (s, 1H); MS (APCI positive) 319.

EXAMPLE 69: $^1$H NMR (CDCl$_3$): δ 1.41 (d, 3H), 1.45 (d, 3H), 3.01 (s, 3H), 3.75 (m, 1H), 8.27 (s, 1H), 8.34 (s, 1H); MS (APCI positive) 303.

Example 70

6,7-Dichloro-3-isopropyl-2-quinoxalinyl-2-(2-methyl-5-nitro-1H-imidazol-1-yl)ethyl Sulfone

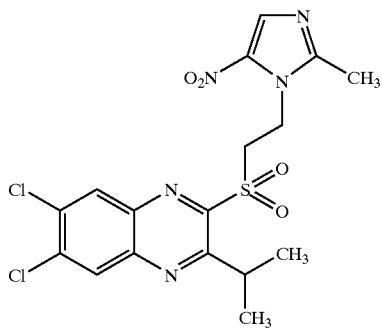

Using the same procedure as for the synthesis of example 68, the title compound was synthesised as pale yellow solids.

$^1$H NMR (CDCl$_3$): δ 1.35 (d, 6H), 2.49 (s, 3H), 3.96 (m, 1H), 4.16 (t, 2H), 4.96 (t, 2H), 7.86 (s, 1H), 8.13 (s, 1H), 8.20 (s, 1H).

MS (APCI positive) 458.

Example 71

3-{[(6,7-Dichloro-3-isopropyl-2-quinoxalinyl)sulfonyl]methyl}benzamide

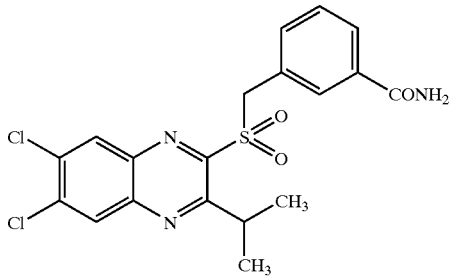

The title compound was prepared using the same procedure as described in example 68.

¹H NMR (CDCl₃): 1.36 (d, 6H), 4.04 (m, 1H), 5.04 (s, 2H), 7.47 (s, 1H), 7.72 (m, 2H), 8.08 (s, 1H), 8.25 (s, 1H), 8.34 (s, 1H).

MS (APCI positive) 438.

Example 72

6,7-Dichloro-2-{[(3,5-dimethyl-4-isoxazoyl)methyl]sulfonyl}-3-isopropylquinoxaline

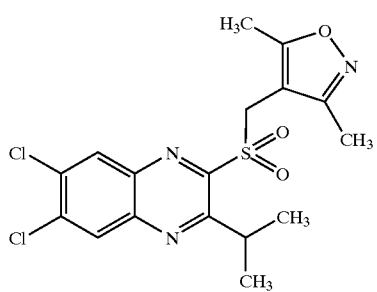

The title compound was prepared using the same procedure as described in example 68.

¹H NMR (CDCl₃): δ 1.40 (d, 6H), 2.35 (s, 3H), 2.47 (s, 3H), 4.04 (m, 1H), 4.78 (s, 2H), 8.24 (s, 1H), 8.29 (s, 1H).
MS (APCI positive) 414.

Example 73

6,7-Dichloro-3-isopropyl-2-(5-chloro-2-thienyl)methyl)quinoxaline

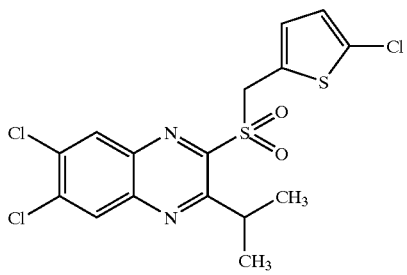

The title compound was prepared using the same procedure as described in example 68.

¹H NMR (CDCl₃): δ 1.38 (d, 6H), 4.04 (m, 1H), 5.10 (s, 2H), 6.81 (d, 1H), 7.01 (d, 1H), 8.2 (s, 2H).

MS (APCI positive) 435.

Example 74

6,7-Dichloro-2-{[2-(1,3-dioxolan-2-yl)ethyl]sulfonyl)-3-isopropylquinoxaline

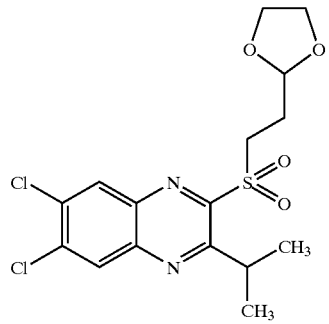

The title compound was prepared using the same procedure as described in example 68.

¹H NMR (CDCl₃): δ 1.42 (d, 6H), 2.37 (m, 2H), 3.85 (t, 2H), 3.92 (m, 2H), 4.03 (m, 2H), 4.11 (m, 1H), 5.12 (t, 1H), 6.81 (d, 1H), 7.01 (d, 1H), 8.20 (s, 2H), 8.26 (s, 1H).

MS (APCI positive) 405.

Example 75

6,7-Dichloro-2-[(cyclopropylmethyl)sulfonyl]-3-isopropylquinoxaline

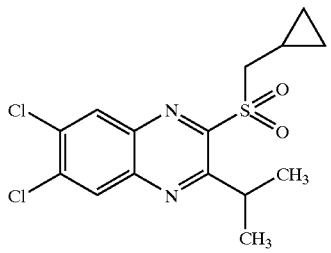

The title compound was prepared using the same procedure as described in example 68.

¹H NMR (CDCl₃): δ 0.51 (m, 2H), 0.73 (m, 2H), 1.32 (m, 1H), 1.43 (d, 6H), 3.66 (s, 2H), 4.17 (m, 1H), 8.18 (s, 1H), 8.26 (s, 1H).

MS (APCI positive) 359.

Example 76

6,7-Dichloro-3-isopropyl-2-[4-(methylsulfonyl)benzylsulfonyl]quinoxaline

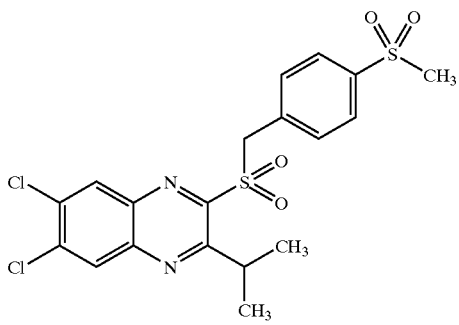

The title compound was prepared using the same procedure as described in example 68.

$^1$H NMR (DMSO-d$_6$): δ 1.27 (d, 6H), 3.19 (s, 3H), 3.92 (m, 1H), 5.38 (s, 2H), 7.80 (d, 2H), 7.91 (d, 2H), 8.51 (s, 1H), 8.67 (s, 1H).

MS (APCI positive) 473.

Example 77

6,7-Dichloro-2-(isopropylsulfonyl)-3-[isopropylsulfonyl)methyl]quinoxaline

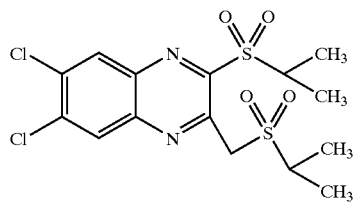

To a solution of 2,6,7-trichloro-3-chloromethylquinoxaline (0.88 mmol) in DMF was added potassium carbonate (1.76 mmol) and 2-isopropylthiol (1.76 mmol). The resulting mixture was stirred at room temperature overnight, followed by partitioning between ethyl acetate and water. The organic layer was dried over magnesium sulfate and concentrated to yield a brown oil upon column chromatography (ethyl acetate:petroleum ether 10:90) (46% yield).

The resulting oil was then dissolved in dichloromethane, followed by addition of mCPBA (4 equivalents). The resulting solution was stirred at room temperature overnight, followed by addition of saturated potassium carbonate. The organic layer was dried and concentrated to yield a crude solid which upon purification by column chromatography (ethyl acetate:petroleum ether 20:80) yielded the title compound as a white solid.

$^1$H NMR (CDCl$_3$): δ 1.37 (d, 6H), 1.41 (d, 6H), 3.42 (m, 1H), 4.18 (m, 1H), 5.21 (s, 2H), 8.25 (s, 1H), 8.26 (s, 1H).

MS (APCI positive) 425.0.

Example 78

6,7-Dichloro-2-isobutyl-3-(methylsulfonyl)quinoxaline

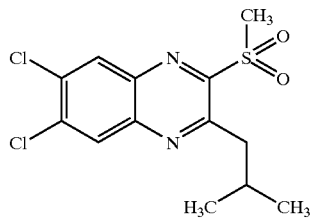

The title compound was prepared using the same procedure as described in example 19. A white solid was isolated and purified by column chromatography (ethyl acetate:petroleum ether 10:90).

$^1$H NMR (CDCl$_3$): δ 0.94 (d, 6H), 2.43 (m, 1H), 3.20 (d, 2H), 3.41 (s, 3H), 8.17 (s, 1H), 8.12 s, 1H).

MS (APCI positive) 333.0.

Example 79

2-(Sec-butyl)-6,7-dichloro-3-(methylsulfonyl)quinoxaline

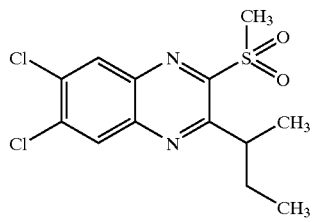

The title compound was prepared using the same procedure as described in example 19. A pale yellow solid was isolated and purified by column chromatography (ethyl acetate:petroleum ether 10:90).

$^1$H NMR (CDCl$_3$): δ 0.81 (t, 3H), 1.30 (d, 3H), 1.65 (m, 2H), 1.96 (m, 1H), 3.41 (s, 3H), 3.79 (m, 1H), 8.11 (s, 1H), 8.18 (s, 1H).

MS (APCI positive) 333.0.

Example 80

6,7-Dichloro-2-(methylsulfonyl)-3-phenethylquinoxaline

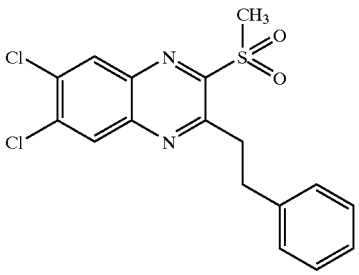

The title compound was prepared using the same procedure as described in example 19. An of off-white solid was isolated and purified by column chromatography (ethyl acetate:petroleum ether 10:90).

$^1$H NMR (CDCl$_3$): δ 3.16 (t, 2H), 3.41 (s, 3H), 3.64 (t, 2H), 7.15 (m, 2H), 7.24 (m, 3H), 8.12 (s, 1H), 8.18 (s, 1H).

MS (APCI positive) 381.0.

Example 81

6,7-Dichloro-3-propyl-2-(4-methylthiazol-2-ylsulfonyl)quinoxaline

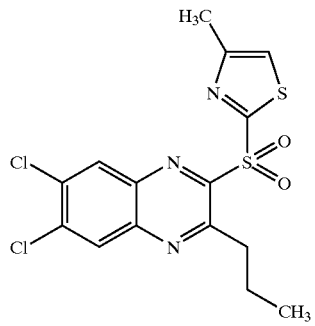

The title compound was prepared using the same procedure as described in example 7. A white solid was isolated and purified by column chromatography (ethyl acetate:petroleum ether 10:90).

$^1$H NMR (CDCl$_3$): δ 1.01 (t, 3H), 1.89 (m, 2H), 2.49 (s, 3H), 3.41 (t, 2H), 7.37 (s, 1H), 7.93 (s, 1H), 8.14 (s, 1H).

MS (APCI positive) 402.0.

Example 82

6,7-Dichloro-3-propyl-2-(4-methylthiazol-2-ylsulfinyl)quinoxaline

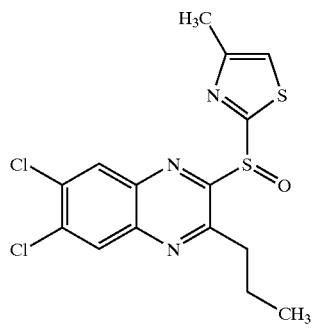

The title compound was prepared using the same procedure as described in example 6.

A white solid was isolated and purified by column chromatography (ethyl acetate:petroleum ether 10:90–30:70).

$^1$H NMR (CDCl$_3$): δ 0.94 (t, 3H), 1.79 (m, 2H), 2.29 (s, 3H), 3.15 (m, 2H), 7.09 (s, 1H), 8.07 (s, 1H), 8.22 (s, 1H).

MS (APCI positive) 386.0.

Example 83

2-Hydroxyethyl 3-{[6,7-dichloro-3-(trifuoromethyl)-2-quinoxalinyl]sulfonyl}propanoate

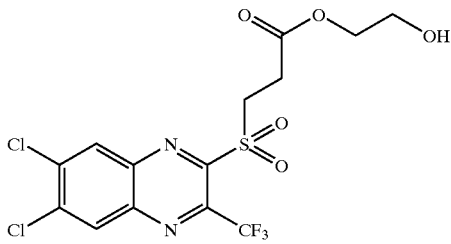

The title compound was prepared using the same procedure as described in example 7. The sulfide was prepared as described in example 12 and oxidised with mCPBA. A white solid was isolated and purified by column chromatography (ethyl acetate:petroleum ether 30:70).

$^1$H NMR (CDCl$_3$): δ 2.98 (t, 2H), 3.78 (t, 2H), 4.05 (t, 2H), 4.20 (t, 2H), 8.34 (s, 1H), 8.41 (s, 1H).

MS (APCI positive) 446.9.

Example 84

N-[6,7-Dichloro-3-(methylsulfonyl)-2-quinoxalinyl]-N-isopropylamine

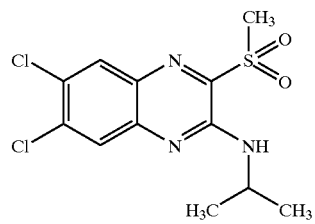

Step 1:

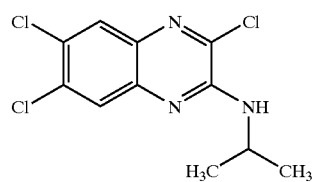

To a solution of 2,3,6,7-tetrachloroquinoxaline (2.12 mmol) in DMF was added caesium carbonate (2.34 mmol) and isopropyl amine (2.12 mmol). The reaction mixture was stirred at room temperature overnight, followed by partitioning between ethyl acetate and water. The organic layer was dried over magnesium sulfate and concentrated to yield a white solid which was purified by column chromatography (ethyl acetate:petroleum ether 10:90).

$^1$H NMR (CDCl$_3$): δ 1.23 (d, 6H), 4.31 (m, 1H), 5.44 (bs, 1H), 7.80 (s, 1H), 7.82 (s, 1H).

MS (APCI positive): 289.9.

Step 2:

The title compound was then prepared from the compound prepared in step 1 using the same procedure as described in example 19.41% yield of a yellow solid was isolated and purified by column chromatography (ethyl acetate:petroleum ether 10:90).

¹H NMR (CDCl₃): δ 1.25 (d, 6H), 3.34 (s, 3H), 4.30 (m, 1H), 6.76 (bs, 1H), 7.75 (s, 1H), 7.88 (s, 1H).
MS (APCI positive) 334.0.

Example 85

N-(6,7-Dichloro-3-(methylsulfonyl)-2-quinoxalinyl)-N-methyl-N-isopropylamine

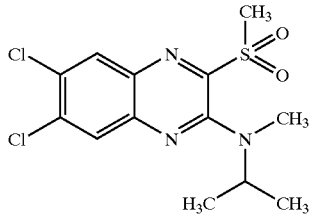

The title compound was prepared using the same procedure as described in example 84. A pale yellow solid was isolated and purified by column chromatography (ethyl acetate:petroleum ether 10:90).
¹H NMR (CDCl₃): δ 1.20 (d, 6H), 3.06 (s, 3H), 3.29 (s, 3H), 4.72 (m, 1H), 7.73 (s, 1H), 7.85 (s, 1H).
MS (APCI positive) 348.

Example 86

N-{6,7-Dichloro-3-(methylsulfonyl)-2-quinoxalinyl}-N-ethylamine

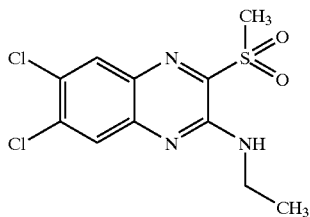

Using the same procedure as described in example 84, the title compound was obtained as a yellow solid.
¹H NMR (CDCl₃): δ 1.33 (t, 3H), 3.42 (s, 3H), 3.60 (m, 2H), 6.34 (s, 1H), 7.84 (s, 1H), 7.97 (s, 1H).
MS (APCI positive) 319.9.

Example 87

2-{[6,7-Dichloro-3-(dimethylamino)-2-quinoxalinyl]sulfonyl}ethanol

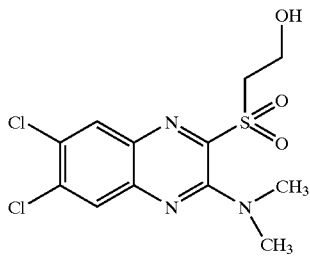

To a solution of 2,3,6,7-tetrachloroquinoxaline (330 mg, 1.2 mmol) in DMF (125 ml) was added potassium fluoride 40% wt on alumina (692 mg, 4.7 mmol) followed by 2-mercaptoethanol (102 mg, 1.3 mmol). The reaction mixture was stirred at room temperature for three days. Analysis by MS (APCI positive) showed that the reaction mixture contained mainly 2-alkylated and 2,3-dialkylated products. The reaction mixture was heated overnight in an oil bath (95° C.). The solvent was evaporated in vacuo and the residue was fractionated by flash column chromatography (ethyl acetate:hexane 1:5 to 1:0) to afford 2-[6,7-dichloro-3-(dimethylamino)-2-quinoxalinyl]sulfanyl}-1-ethanol. This compound (72 mg, 0.2 mmol) was dissolved in dichloromethane (6 ml) and 3-chloroperoxybenzoic acid (104 mg, 0.47 mmol) was added. After stirring at room temperature for 1 hour, the reaction was quenched by addition of sodium bicarbonate and water, then extracted with dichloromethane. The title compound was obtained as a yellow oil after purification by flash column chromatography (ethyl acetate:hexane 1:3).
¹H NMR (CDCl₃): δ 3.34 (s, 6H), 3.93 (m, 2H), 4.10 (m, 2H), 7.87 (s, 1H), 7.95 (s, 1H).
MS (APCI positive) 350.0.

Example 88

N-{6,7-Dichloro-3-(methylsulfonyl)-2-quinoxalinyl}N,N-dimethylamine

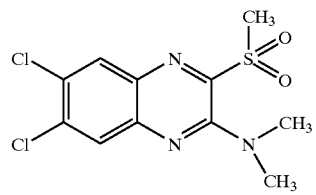

Using the same procedure as described in example 84, the title compound was obtained as a yellow solid.
¹H NMR (CDCl₃): δ 3.34 (s, 6H), 3.40 (s, 3H), 7.86 (s, 1H), 7.96 (s, 1H).
MS (APCI positive) 320.0.

Example 89

6,7-Dichloro-2-[(1-methyl-1H-tetrazol-5-yl)sulfinyl]-3-propylquinoxaline

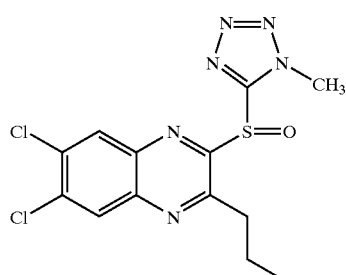

Using the same procedure as described in example 6, the title compound was obtained as a pale yellow solid.
¹H NMR (CDCl₃): δ 1.10 (t, 3H), 1.96 (m, 2H), 3.25 (m, 2H), 4.49 (s, 3H), 8.23 (s, 1H) 8.27 (s, 1H).
MS (APCI positive) 371.0.

Example 90

6,7-Dichloro-3-ethyl-2-(methylsulfonyl)quinoxaline

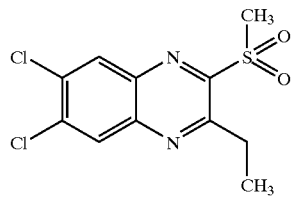

The title compound was obtained using the same procedure as described for the preparation of examples 15 and 19.

$^1$H NMR (CDCl$_3$): δ 1.47 (t, 3H), 3.48 (m, 2H), 3.50 (s, 3H), 8.21 (s, 1H), 8.27 (s, 1H).

MS (APCI positive) 305.0.

Example 91

6,7-Dichloro-2-(methylsulfonyl)-3-hexylquinoxaline

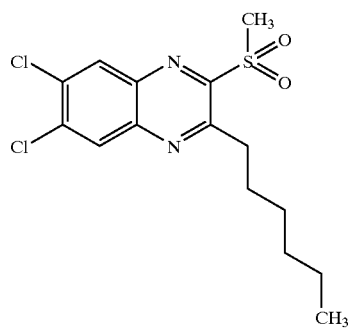

The title compound was obtained as an oil using the same procedure as described for the preparation of examples 15 and 19.

$^1$H NMR (CDCl$_3$): δ 0.89 (m, 3H), 1.35 (m, 4H), 1.46 (m, 2H), 1.92 (m, 2H), 3.40 (t, 2H), 3.50 (s, 3H), 8.21 (s, 1H), 8.26 (s, 1H).

MS (APCI positive) 361.0.

Example 92

6,7-Dichloro-2-(methylsulfonyl)-3-propylquinoxaline

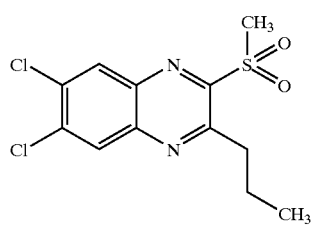

The title compound was obtained using the same procedure as described for the preparation of examples 15 and 19.

$^1$H NMR (CDCl$_3$): δ 1.09 (t, 3H), 1.95 (m, 2H), 3.38 (t, 2H), 3.50 (s, 3H), 8.19 (s, 1H), 8.24 (s, 1H).

MS (APCI positive) 319.0.

Example 93

6,7-Dichloro-2-(cyclopentylsulfonyl)-3-(trifluoromethyl)quinoxaline

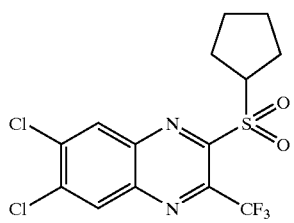

The title compound was using the same procedure as described in example 34.

$^1$H NMR (CDCl$_3$): δ 1.74 (m, 2H), 1.89 (m, 2H), 2.14 (m, 4H), 4.55 (m, 1H), 8.37 (s, 1H), 8.46 (s, 1H).

MS (APCI negative) 397.9.

Example 94

6,7-Dichloro-2-(isopentylsulfonyl)-3-(trifluoromethyl)quinoxaline

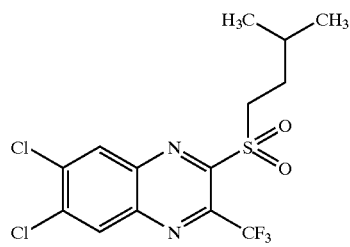

The title compound was obtained as a white solid using the same procedure as described in example 34.

$^1$H NMR (CDCl$_3$): δ 1.01 (d, 6H), 1.81 (m, 3H), 3.74 (m, 2H), 8.37 (s, 1H), 8.47 (s, 1H).

MS (APCI positive) 401.0.

Example 95

2-Chloro-6-nitro-3-trifluoromethylquinoxaline

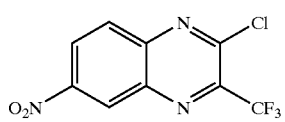

The title compound was obtained as an amber oil using the same procedure as described for the preparation of example 15.

$^1$H NMR (CDCl$_3$): δ 8.30 (bd, 1H), 8.74 (bq, 1H), 9.14 (d, 1H).

MS (APCI negative) 276.9.

Example 96

3-(6,7-Dichloro-3-trifluoromethylquinoxaline-2-sulfonyl)propionic Acid Methyl Ester

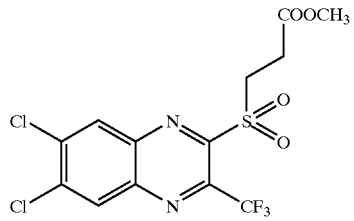

The title compound was obtained using the same procedure as described in example 34.

¹H NMR (CDCl₃): δ 2.84 (t, 2H), 3.50 (s, 3H), 3.98 (t, 2H), 8.69 (s, 1H), 8.72 (s, 1H).

MS (APCI positive) 417.0.

Example 97

2-[(5-Methyl-1,3,4-thiadiazol-2-yl)sulfanyl]-6-nitro-3-(trifluoromethyl)quinoxaline

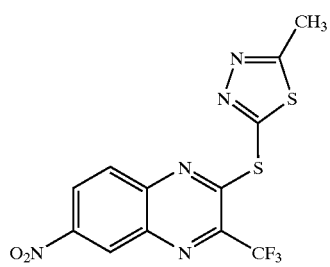

The title compound was obtained using the same procedure as described for example 1.

¹H NMR (CDCl₃): δ 2.91 (s, 3H), 8.23 (d, 1H), 8.73 (bq, 1H), 9.07 (d, 1H).

MS (APCI positive) 374.0.

Example 98

6,7-Dichloro-2-[(1-methyltetrazol-5-yl)sulfonyl]-3-propylquinoxaline

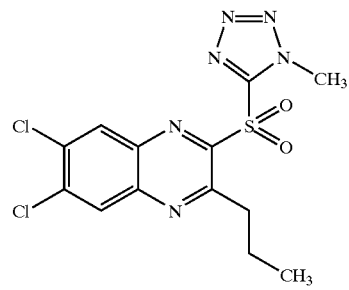

The title compound was obtained using the same procedure as described in example 34.

¹H NMR (CDCl₃): δ 1.14 (t, 3H), 2.02 (m, 2H), 3.47 (t, 2H), 4.44 (s, 3H), 7.93 (s, 1H), 8.29 (s, 1H).

MS (APCI positive) 387.0.

Example 99

6,7-Dichloro-2-[(1-phenyltetrazol-5-yl)sulfinyl]-3-propylquinoxaline

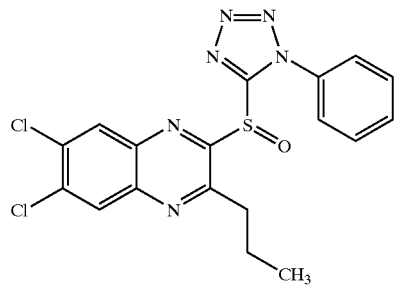

The title compound was obtained using the same procedure as described in example 34.

¹H NMR (CDCl₃): δ 1.07 (t, 3H), 1.75 (m, 2H), 3.05 (m, 2H), 7.46 (brd m, 3H), 7.57 (brd m, 2H), 7.74 (s, 1H), 8.53 (s, 1H).

MS (APCI positive) 433.0.

Example 100

6,7-Dichloro-2-(isopropylsulfonyl)-3-propylquinoxaline

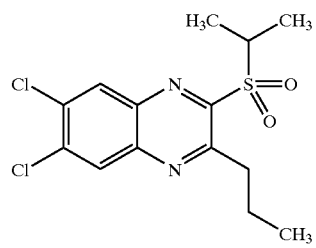

The title compound was obtained using the same procedure as described in example 34.

¹H NMR (CDCl₃): δ 1.09 (t, 3H), 1.52 (d, 6H), 1.94 (m, 2H), 3.40 (t, 2H), 4.37 (m, 1H), 8.20 (s, 1H), 8.24 (s, 1H).

MS (APCI positive) 347.0.

Example 101

6,7-Dichloro-2-[(1-phenyltetrazol-5-yl)sulfonyl]-3-propylquinoxaline

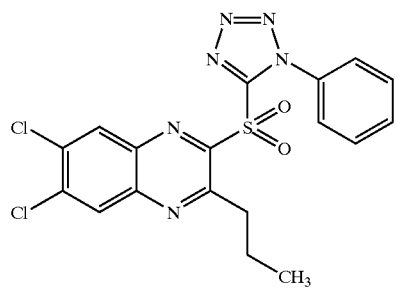

The title compound was prepared using the same procedure as described in example 34.

Example 102

N-[6,7-Dichloro-3-(methylsulfonyl)-2-quinoxalinyl] pyrazolidin-3-one

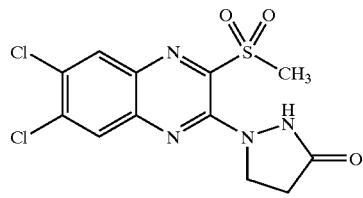

The title compound was prepared using the same procedure as described for the preparation of example 84.

$^1$H NMR (CDCl$_3$): δ 2.71 (t, 2H), 3.44 (s, 3H), 4.50 (t, 2H), 7.26 (bs, 1H), 7.90 (s, 1H), 8.03 (s, 1H).

MS (APCI positive) 334.0.

Example 103

N-[6,7-Dichloro-3-(methylsulfonyl)-2-quinoxalinyl] N-tert-butylamine

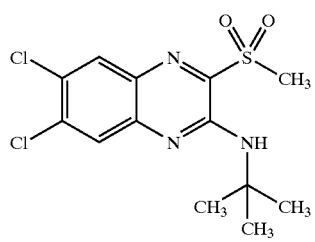

The title compound was prepared using the same procedure as described for the preparation of example 84.

$^1$H NMR (CDCl$_3$): δ 1.54 (s, 9H), 3.40 (s, 3H), 6.95 (bs, 1H), 7.81 (s, 1H), 7.92 (s, 1H).

MS (APCI positive) 348.0.

Example 104

N-[6,7-Dichloro-3-(methylsulfonyl)-2-quinoxalinyl]-N-isobutylamine

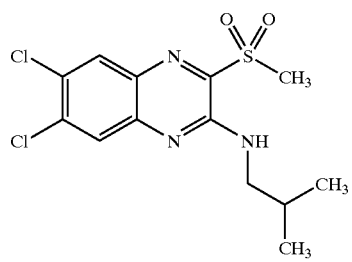

The title compound was prepared using the same procedure as described for the preparation of example 84.

$^1$H NMR (CDCl$_3$): δ 1.02 (d, 6H), 2.01 (m, 1H), 3.39 (d, 2H), 3.42 (s, 3H), 7.05 (bs, 1H), 7.82 (s, 1H), 7.95 (s, 1H).

MS (APCI positive) 348.0.

Example 105

N-[6,7-Dichloro-3-(methylsulfonyl)-2-quinoxalinyl]-N-(1,1,-dioxo-tetrahydro-thiophen-3-yl)amine

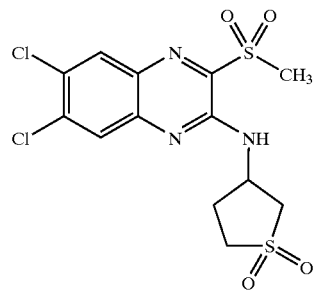

The title compound was prepared using the same procedure as described for the preparation of example 84.

$^1$H NMR (CDCl$_3$): δ 2.73 (m, 1H), 2.40 (m, 1H), 3.10 (dd, 1H), 3.23 (m, 1H), 3.39 (m, 1H), 3.44 (s, 3H), 3.73 (dd, 1H), 4.95 (m, 1H), 7.35 (d, 1H), 7.89 (s, 1H), 8.05 (s, 1H).

MS (APCI positive) 410.0.

Example 106

N-[6,7-Dichloro-3-(methylsulfanyl)-2-quinoxalinyl]-N'-acetylethylenediamine

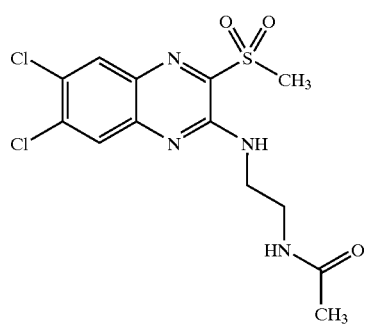

The title compound was prepared using the same procedure as described for the preparation of example 84.

$^1$H NMR (CDCl$_3$): δ 1.97 (s, 3H), 3.40 (s, 3H), 3.55 (q, 2H), 3.72 (q, 2H), 7.21 (b, 1H), 7.78 (s, 1H), 7.95 (s, 1H).

MS (APCI positive) 377.0.

Example 107

N-[6,7-Dichloro-3-(methylsulfonyl)-2-quinoxalinyl]-N-(1,1-dimethylbenzyl)amine

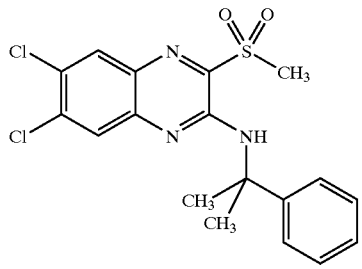

The title compound was prepared using the same procedure as described for the preparation of example 84.

¹H NMR (CDCl₃): δ1.86 (s, 6H), 3.44 (s, 3H), 7.20 (m, 1H), 7.29 (m, 2H), 7.47 (m, 3H), 7.49 (s, 1H), 7.89 (s, 1H).

MS (APCI positive) 410.0.

Example 108

N-[6,7-Dichloro-3-(methylsulfonyl)-2-quinoxalinyl]-N-(1,2,3,4-tetrahydro-naphthalene-1-yl)amine

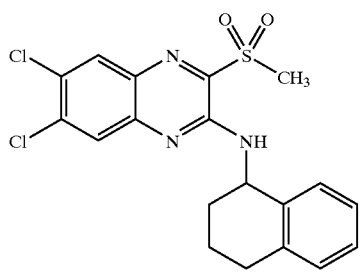

The title compound was prepared using the same procedure as described for the preparation of example 84.

¹H NMR (CDCl₃): δ 1.95 (m, 3H), 2.01 (m, 1H), 2.86 (m, 2H), 3.40 (s, 3H), 5.56 (m, 1H), 7.16 (d, 2H), 7.19 (d, 2H), 7.35 (d, 1H), 7.87 (s, 1H), 7.99 (s, 1H).

MS (APCI positive) 422.0.

Example 109

Methyl 3-{[(4-{[(6,7-dichloro-3-isopropyl-2-quinoxalinyl)sulfonyl]methyl}phenyl)sulfanyl]amino}propanoate

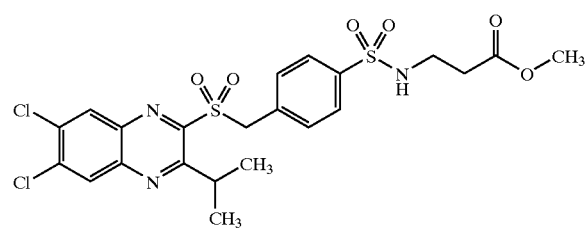

Using the same procedure as described for the preparation of example 35, the title compound was obtained as a white solid.

¹H NMR (CDCl₃): δ 1.39 (d, 6H), 2.56 (t, 2H), 3.22 (q, 2H), 3.67 (s, 3H), 4.05 (m, 1H), 7.70 (d, 2H), 7.88 (d, 2H), 8.26 (s, 1H), 8.29 (s, 1H).

MS (APCI positive) 560.0.

Example 110

6,7-Dichloro-2-[(1-methyl-1H-imidazol-2-yl)sulfonyl]-3-propylquinoxaline

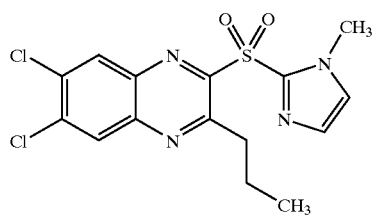

Using the same procedure as described for the preparation of example 34, the title compound was obtained as a yellow solid.

¹H NMR (CDCl₃): δ 1.10 (t, 3H), 2.00 (m, 2H), 3.47 (t, 2H), 4.04 (s, 3H), 7.22 (s, 1H), 7.29 (s, 1H), 7.96 (s, 1H), 8.22 (s, 1H).

MS (APCI positive) 385.0.

Example 111

6,7-Dichloro-2-(methylsulfonyl)-3-(1-pyrrolidinyl)quinoxaline

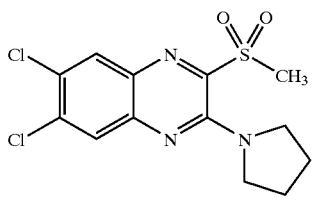

Using the same procedure as described in example 84, the title compound was obtained as a yellow solid.

¹H NMR (CDCl₃): δ 2.01 (m, 4H), 3.45 (s, 3H), 3.89 (m, 4H), 7.81 (s, 1H), 7.91 (s, 1H).

MS (APCI positive) 346.0.

Example 112

1-[6,7-Dichloro-3-(methylsulfonyl)-2-quinoxalinyl]-3-pyrrolidinol

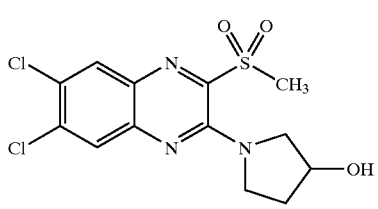

Using the same procedure as described in example 84, the title compound was obtained as a yellow solid.

$^1$H NMR (CDCl$_3$): δ 2.12 (m, 2H), 3.45 (s, 3H), 3.98 (m, 2H), 4.08 (m, 2H), 4.64 (m, 1H), 7.83 (s, 1H), 7.93 (s, 1H).
MS (APCI positive) 362.0.

Example 113

2-[6,7-Dichloro-3-(methylsulfonyl)-2-quinoxalinyl]-4-phenylsemicarbazide

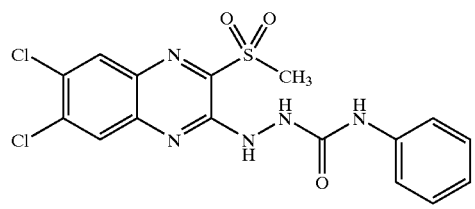

To a solution of 3,6,7-trichloro-2-(methylsulfonyl) quinoxaline (312 mg, 1.0 mmol) in DMF (10 ml) was added caesium carbonate (489 mg, 1.5 mmol) followed by 4-phenylsemicarbazide (182 mg, 1.2 mmol). The reaction was stirred overnight at room temperature. The product was purified by flash column chromatography using ethyl acetate:hexane 1:1 obtaining the title compound as a solid.

$^1$H NMR (DMSO-d$_6$): δ 3.55 (s, 3H), 6.95 (m, 1H), 7.24 (m, 2H), 7.43 (m, 2H), 8.02 (s, 1H), 8.34 (s, 1H), 8.53 (s, 1H), 8.95 (brd s, 1H), 9.01 (s, 1H).
MS (APCI positive) 425.9.

Example 114

(6,7-Dichloro-3-methylsulfonyl-8-nitroquinoxalin-2-yl)isopropylamine

To a stirred suspension of 6,7-dichloroquinoxaline-2,3-diol (1.0 g, 4.3 mmol) in concentrated sulfuric acid (20 ml) at 0° C. was added sodium nitrate (554 mg, 6.5 mmol) in portions over 15 minutes. The reaction mixture was stirred overnight at room temperature. The reaction was quenched by slowly pipetting into ice water. The precipitate was collected by vacuum filtration and the beige solid was washed with water. The nitrated product was suspended in phosphorous oxychloride, about 6 ml of DMF was added to make it homogeneous and the reaction was heated at reflux overnight. The reaction was quenched by slowly pipetting into ice water. The aqueous mixture was then extracted twice with ethyl acetate. The organic layers were combined and concentrated in vacuo to a beige solid. To a solution of the chlorinated product (1.57 g, crude) in DMF was added caesium carbonate (2.36 g, 7.2 mmol) followed by isopropyl amine (0.31 ml). The reaction mixture was stirred overnight at room temperature. The solvent was removed in vacuo. The solid was taken up in water and ethyl acetate. The layers were separated and the aqueous layer was extracted twice with ethyl acetate. The organic layers were combined and concentrated to a yellow solid that was purified by flash column chromatography using ethyl acetate:hexane 1:10. To a solution of the aminated product (588 mg, 1.7 mmol) in DMF (20 ml) was added methanesulfinic acid sodium salt (215 mg, 2.1 mmol). The solution was stirred overnight at room temperature. The final product was purified by flash column chromatography using ethyl acetate:hexane 1:5 obtaining the title compound as a yellow solid.

$^1$H NMR (CDCl$_3$): δ 1.29 (d, 6H), 3.42 (s, 3H), 4.25 (m, 1H), 7.13 (bd, 1H), 8.09 (s, 1H). MS (APCI positive) 378.9.

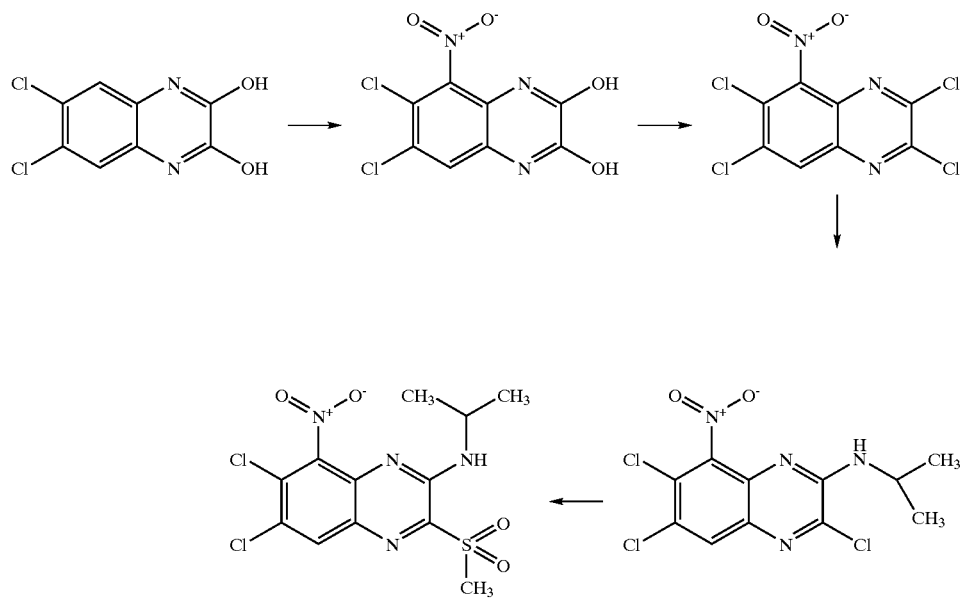

Example 115

N-(tert-Butyl)-N-{6,7-dichloro-3-[(6-fluoro-4H-1,3-benzodioxin-8-yl)methylsulfonyl]-2-quinoxalinyl}amine

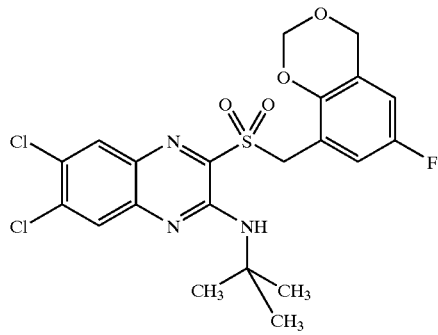

Using the same procedure as described for the preparation of example 35, the title compound was obtained as a yellow solid.

$^1$H NMR (CDCl$_3$): δ 1.40 (s, 9H), 4.71 (m, 6H), 6.73 (m, 1H), 7.05 (m, 2H), 7.79 (s, 1H), 8.00 (s, 1H).

MS (APCI positive) 500.0.

Example 116

N-(tert-Butyl)-N-{6,7-dichloro-3-{[4-(difluoromethoxy)benzyl]sulfonyl}-2-quinoxalinyl}amine

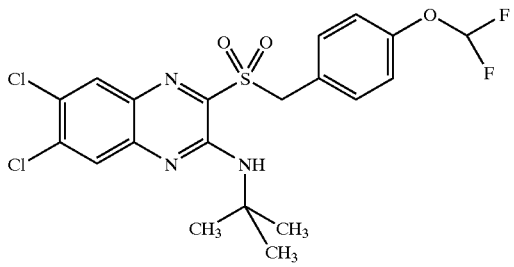

Using the same procedure as described for the preparation of example 35, the title compound was obtained as a yellow solid.

$^1$H NMR (CDCl$_3$): δ 1.40 (s, 9H), 4.75 (s, 2H), 6.25–6.74 (t, 1H), 6.99 (s, 1H), 7.07 (m, 2H), 7.29 (m, 2H), 7.79 (s, 1H), 8.01 (s, 1H).

MS (APCI positive) 490.0.

Example 117

4-[2-({3-[(6,7-Dichloro-3-isopropyl-2-quinoxalinyl)sulfonyl]propanoyl}amino)ethyl]morpholine-N-oxide

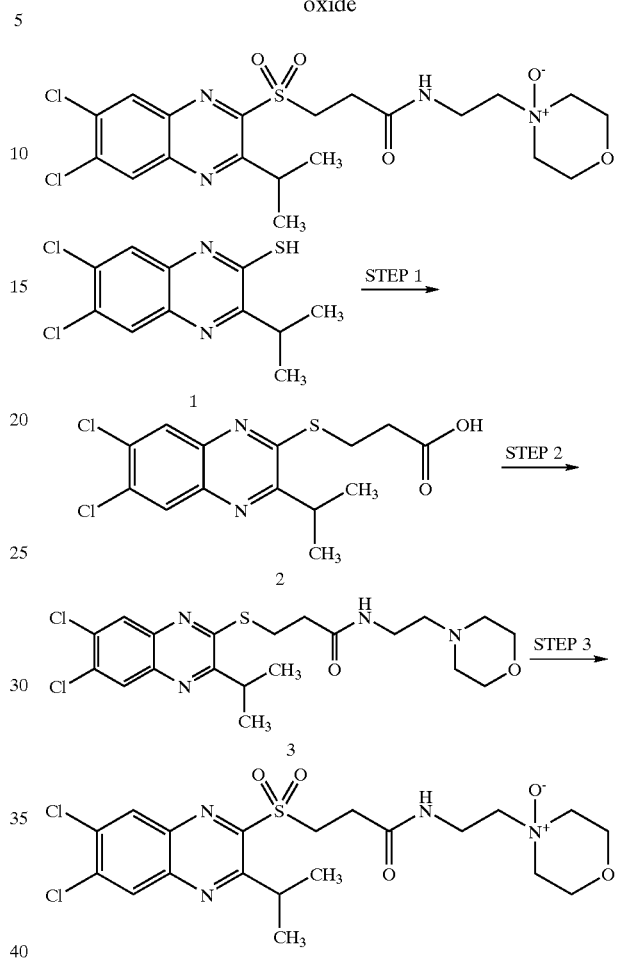

Step 1:

To a solution of 6,7-dichloro-3-isopropyl-2-mercaptoquinoxaline (800 mg, 2.94 mmol) (1) in DMF (20 ml) was added a small scoop of potassium carbonate followed by 3-mercapto-propionic acid (312 mg, 2.94 mmol). The reaction mixture was stirred at room temperature. After 5 hours, thin layer chromatography showed all starting material was gone. The solvent was removed in vacuo, the residue was dissolved in ethyl acetate and 10% HCl was added. The layers were separated and the aqueous layer was extracted twice with ethyl acetate. The organic layers were combined and concentrated under reduced pressure to obtain a pale yellow solid (2) (1.05 g) with the following data:

$^1$H NMR (CDCl$_3$): δ 1.26 (d, 6H), 2.80 (m, 2H), 3.27 (m, 1H), 3.48 (m, 2H), 7.87 (s, 1H), 8.09 (s, 1H).

MS (APCI positive): 345.0.

Step 2:

To a solution of the above acid (2) (160 mg, 0.465 mmol) and 1-(3-dimethylaminopropyl)-3-ethylcarbodiimide hydrochloride (89 mg, 0.558 mmol) in 3 ml of dichloromethane was added 4-(2-aminoethyl)morpholine (60 mg, 0.465 mmol). The reaction mixture was stirred at room temperature for 5 h. The solvent was removed and the residue was partitioned in water and ethyl acetate. The organic layer was separated and concentrated to a white solid (3). It was used in the next step without further purification.

Step 3:

To a suspension of 3-[(6,7-dichloro-3-isopropyl-2-quinoxalinyl)sulfanyl]-N-[2-(4-morpholinyl)-ethyl]propanamide (0.465 mmol) (prepared by using the method according to example 35) in dichloromethane (20 ml) was added mCPBA (1.16 mmol) at room temperature. The solution was stirred overnight and concentrated to a pale yellow foam. The crude material was then redissolved in ethyl acetate and washed with water and brine, dried over anhydrous magnesium sulfate, and concentrated to yield a beige solid. The title compound was isolated and purified by preparative HPLC chromatography to yield a white solid.

$^1$H NMR (CDCl$_3$): δ 1.34 (d, 6H), 2.87 (t, 2H), 3.30 (m, 2H), 3.42 (m, 2H), 3.57 (m, 2H), 3.79 m, 4H), 4.03 (m, 3H), 4.23 (t, 2H), 8.18 (s, 2H), 8.52 (bs, 1H).

MS (APCI positive): 505.1.

Example 118

Ethyl 3[({4-[6,7-dichloro-3-isopropyl-2quinoxalinyl]sulfonyl}butoxy)carbonyl]amino-propanoate

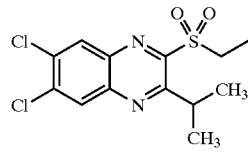

To a solution of 4-[(6,7-dichloro-3-isopropyl-2-quinoxalinyl)sulfanyl]-1-butanol (0.822 mmol) (prepared by using the method according to example 35) and ethyl 3-isocyanatopropionate (0.822 mmol) in toluene was added dibutyl tin dilaurate catalyst (0.01%). The resulting mixture was heated to 80° C. for 6 hours. The solvent was then evaporated and the resulting solid redissolved in ethyl acetate and washed twice with water, dried over magnesium sulfate, and concentrated further to a pale yellow solid (94%). The crude product was then suspended in dichloromethane (30 ml) and 2.1 equivalents of mCPBA were added. The resulting solution was stirred at room temperature overnight. The solvent was evaporated and the title compound was isolated and purified by column chromatography to yield a white solid (petroleum ether:ethyl acetate 80:20).

$^1$H NMR (CDCl$_3$): δ 1.17 (t, 3H), 1.35 (d, 6H), 1.82 (m, 2H), 1.98 (m, 2H), 2.45 (m, 2H), 3.36 (m, 2H), 3.70 (m, 2H), 4.07 (cm, 5H), 5.17 (bs, 1H), 8.12 (s, 1H), 8.18 (s, 1H).

MS (APCI positive): 520.1.

Example 119

Ethyl 3-[(3-{[6,7-dichloro-3-isopropyl-2-quinoxalinyl)sulfonyl]methyl}benzoyl)amino]-propanoate

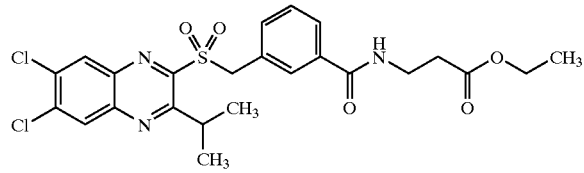

Using the procedure described in example 35, the title compound was isolated and purified by column chromatography (petroleum ether:ethyl acetate 80:20) to yield an off white solid (48%).

$^1$H NMR (CDCl$_3$): δ 1.20 (t, 3H), 1.31 (d, 6H), 2.57 (t, 2H), 3.65 (q, 2H), 3.98 (m, 1H), 4.10 (q, 2H), 4.98 (s, 2H), 6.80 (bs, 1H), 7.38 (m, 1H), 7.65 (m, 2H), 7.95 (s, 1H), 8.19 (s, 1H), 8.28 (s, 1H).

MS (APCI positive): 538.1.

Example 120

Ethyl 3-[(4-{[6,7-dichloro-3-isopropyl-2-quinoxalinyl)sulfonyl]methyl}benzoyl)amino]-propanoate

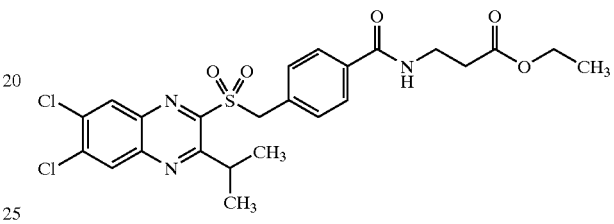

Using the procedure described in example 35, the title compound was isolated and purified by column chromatography (petroleum ether ethyl acetate 70:30) to yield a white solid.

$^1$H NMR (CDCl$_3$): δ 1.19 (t, 3H), 1.29 (d, 6H), 2.55 (t, 2H), 3.64 (m, 2H), 3.97 (m, 1H), 4.09 (q, 2H), 4.98 (s, 2H), 6.80 (bs, 1H), 7.53 (d, 2H), 7.69 (d, 2H), 8.20 (s, 2H).

MS (APCI positive): 538.1.

Example 121

3-[(4-{[(6,7-Dichloro-3-isopropyl-2-quinoxalinyl)sulfonyl]methyl}benzoyl)amino]-1-pyridine-N-oxide

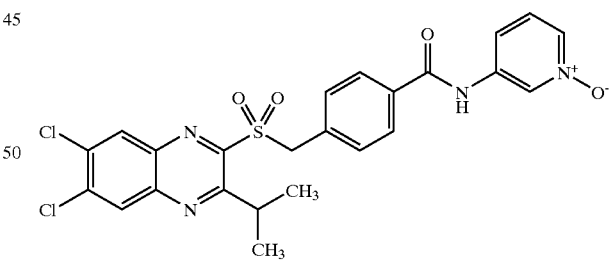

Using the procedure described in example 35, the title compound was isolated and purified by column chromatography (petroleum ether:ethyl acetate 50:50) to yield an off white solid (67%).

$^1$H NMR (DMSO-d$_6$): δ 1.28 (d, 6H), 3.94 (m, 1H), 5.33 (s, 2H), 7.39 (m, 1H), 7.63 (d, 1H), 7.70 (d, 2H), 7.90 (d, 2H), 7.97 (d, 1H), 8.51 (s, 1H), 8.69 (s, 1H), 8.76 (s, 1H), 10.55 (s, 1H).

MS (APCI positive): 531.0.

Example 122

4-{[(6,7-Dichloro-3-isopropyl-2-quinoxalinyl)sulfonyl]methyl}-N-(3-pyridinyl)benzamide

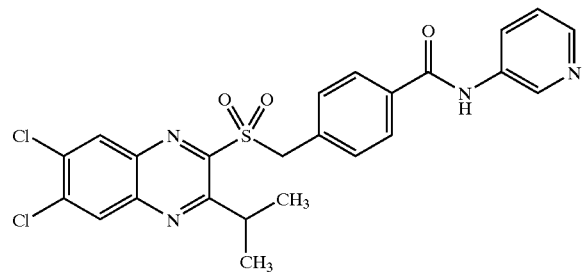

Using the procedure described in example 35, the title compound was purified by preparative HPLC chromatography.

$^1$H NMR (DMSO-d$_6$): δ 1.39 (d, 6H), 4.08 (m, 1H), 5.28 (s, 2H), 7.47 (m, 2H), 7.75 (d, 2H), 7.98 (d, 2H), 8.26 (bd, 1H), 8.36 (bs, 1H), 8.38 (s, 1H), 8.55 (s, 1H), 8.90 (bs, 1H).

MS (APCI positive): 515.1.

Example 123

5,6,7,8-Tetrachloro-2-isopropyl-3-(methylsulfonyl)quinoxaline

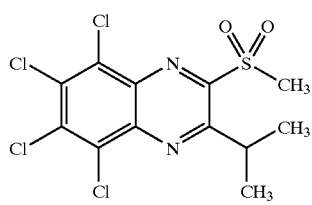

Using the procedure described in example 19, the title compound was isolated and purified by column chromatography (petroleum ether:ethyl acetate 90:10) to yield a light orange solid.

$^1$H NMR (CDCl$_3$): δ 1.35 (d, 6H), 3.48 (s, 3H), 4.12 (m, 1H).

MS (APCI positive): 388.9.

Example 124

5,6,7,8-Tetrachloro-2-isopropyl-3-[(1-methylimidazol-2-yl)sulfonyl]quinoxaline

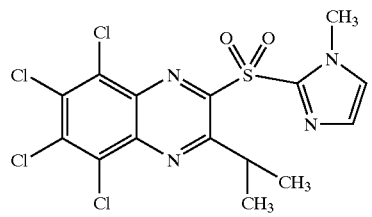

Using the procedure described in example 7, the title compound was isolated and purified by column chromatography (petroleum ether:ethyl acetate 80:20) to yield an off white solid.

$^1$H NMR (CDCl$_3$): δ 1.47 (d, 6H), 4.01 (s, 3H), 4.25 (m, 1H), 7.19 (s, 1H), 7.25 (s, 1H).

MS (APCI positive): 454.9.

Example 125

(6,7-Dichloro-3-methylsulfonylquinoxalin-2-yl)cyclopropylamine

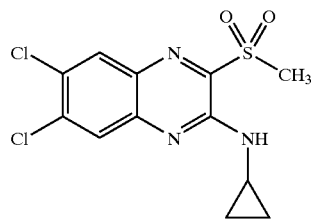

Using the procedure described in example 84, the title compound was isolated and purified by column chromatography (petroleum ether:ethyl acetate 90:10) to yield a yellow solid.

$^1$H NMR (CDCl$_3$): δ 0.55 (m, 2H), 0.85 (m, 2H), 2.86 (m, 1H), 7.03 (bs, 1H), 7.86 (s, 1H), 7.91 (s, 1H).

MS (APCI positive): 331.9.

Example 126

(6,7-Dichloro-3-methylsulfonylquinoxalin-2-yl)cyclopentylamine

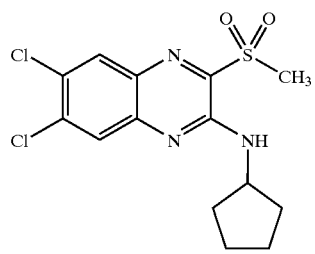

Using the procedure described in example 84, the title compound was isolated and purified by column chromatography (petroleum ether:ethyl acetate 90:10) to yield a yellow solid.

$^1$H NMR (CDCl$_3$): δ 1.56 (m, 2H), 1.75 (cm, 4H), 2.14 (m, 2H), 3.41 (s, 3H), 4.44 (m, 1H), 7.00 (bd, 1H), 7.84 (s, 1H), 7.96 (s, 1H).

MS (APCI positive): 360.0.

Example 127

6,7-Dichloro-2-[methoxy(methyl)amino]-3-(methylsulfonyl)quinoxaline

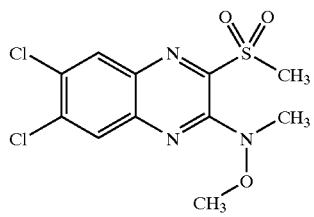

Using the procedure described in example 84, the title compound was isolated and purified by column chromatography (petroleum ether:ethyl acetate 70:30) to yield a yellow solid.

$^1$H NMR (CDCl$_3$): δ 3.33 (s, 3H), 3.39 (s, 3H), 3.86 (s, 3H), 7.92 (s, 1H), 8.01 (s, 1H).

MS (APCI positive): 336.0.

Example 128

N-{6,7-Dichloro-3-[1-methylimidazol-2-yl)sulfonyl]-2-quinoxalinyl}-N-isopropylamine

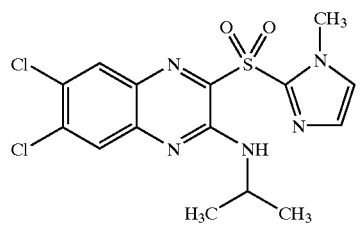

Using the procedure described in example 84, the title compound was isolated and purified by column chromatography (petroleum ether:ethyl acetate 70:30) to yield a yellow solid.

$^1$H NMR (CDCl$_3$): δ 1.34 (d, 6H), 4.15 (s, 3H), 4.38 (m, 1H), 7.22 (bm, 2H), 7.79 (s, 1H), 7.87 (s, 1H).

MS (APCI positive): 400.0.

Example 129

(6,7-Dichloro-3-methylsulfonylquinoxalin-2-yl)-sec-butylamine

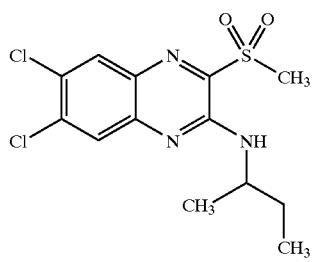

Using the procedure described in example 84, the title compound was isolated and purified by column chromatography (petroleum ether:ethyl acetate 90:10).

$^1$H NMR (CDCl$_3$): δ 1.00 (t, 3H), 1.29 (d, 3H), 1.66 (bm, 3H), 3.42 (s, 3H), 4.25 (m, 1H), 6.83 (bd, 1H), 7.82 (s, 1H), 7.96 (s, 1H).

MS (APCI positive): 348.0.

Example 130

(6,7-Dichloro-3-{[(6-fluoro-4H-1,3-benzodioxin-8-yl)methyl]sulfonyl}quinoxalin-2-yl)isopropylamine

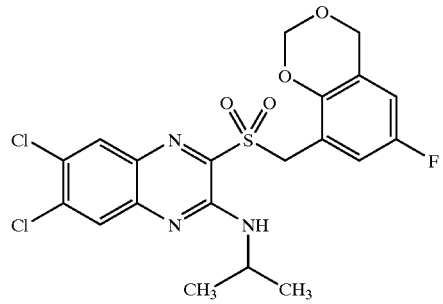

Using the procedure described in example 35, the title compound was isolated and purified by column chromatography (petroleum ether ethyl acetate 90:10) to yield a yellow solid.

$^1$H NMR (CDCl$_3$): δ 1.10 (d, 6H), 4.15 (m, 1H), 4.65 (s, 2H), 4.71 (s, 2H), 6.65 (m, 1H), 6.87 (m, 1H), 6.95 (dd, 1H), 7.73 (s, 1H), 7.94 (s, 1H).

MS (APCI positive): 486.0.

Example 131

3-{[6,7-Dichloro-3-(methylsulfonyl)-2-quinoxalinyl]-amino}2-azepanone

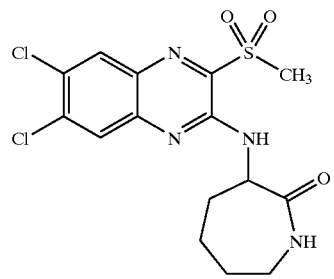

Using the procedure described in example 84, the title compound was isolated and purified by column chromatography (petroleum ether:ethyl acetate 80:20).

$^1$H NMR (CDCl$_3$): δ 1.96 (bm, 6H), 3.29 (m, 1H), 3.34 (s, 3H), 4.75 (m, 2H), 5.96 (bs, 1H), 7.76 (s, 1H), 7.94 (s, 1H), 8.27 (m, 1H).

MS (APCI positive): 403.0.

Example 132

(6,7-Dichloro-)-3-(methylsulfonyl)quinoxalin-2-yl)-1-ethylpropylamine

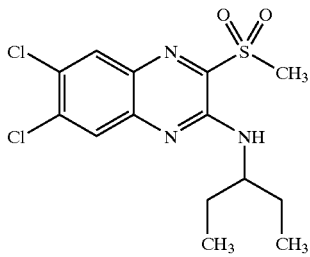

Using the procedure described in example 84, the title compound was isolated and purified by column chromatography (petroleum ether ethyl acetate 90:10) to yield a yellow solid.

$^1$H NMR (CDCl$_3$): δ 0.89 (t, 6H), 1.55 (cm, 4H), 3.35 (s, 3H), 4.11 (m, 1H), 6.71 (bd, 1H), 7.73 (s, 1H), 7.87 (s, 1H).

MS (APCI positive): 362.0.

Example 133

(7-Chloro-3-(methylsulfonyl)6-nitroquinoxalin-2-yl)sec-butylamine

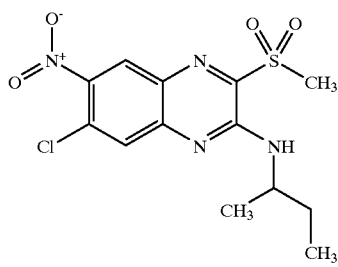

Using the procedure described in example 84, the title compound was isolated and purified by column chromatography (petroleum ether:ethyl acetate 90:10) to yield a yellow solid.

$^1$H NMR (CDCl$_3$): δ 1.01 (t, 3H), 1.31 (d, 3H), 1.69 (m, 2H), 3.46 (s, 3H), 4.30 (m, 1H), 7.12 (bd, 1H), 7.81 (s, 1H), 8.47 (s, 1H).

MS (APCI positive): 359.0.

Example 134

(6-Chloro-3-methylsulfonyl-7-nitro-8-trifluoromethylquinoxalin-2-yl)isopropylamine

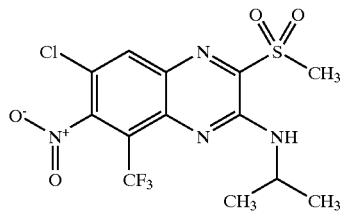

Using the procedure described in example 84, the title compound was isolated and purified by column chromatography (petroleum ether:ethyl acetate 80:20) to yield yellow crystals.

$^1$H NMR (CDCl$_3$): δ1.40 (d, 6H), 3.48 (s, 3H), 4.50 (m, 1H), 8.21 (s, 1H).

MS (APCI negative): 411.0.

Example 135

(6,7-Dichloro-3-(methylsulfonyl)=quinoxalin-2-yl)tert-pentylamine

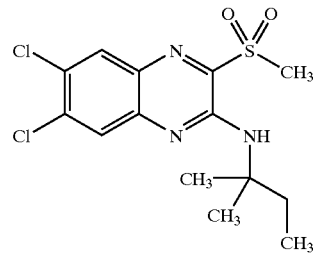

Using the procedure described in example 84, the title compound was isolated and purified by column chromatography (petroleum ether ethyl acetate 80:20) to yield a yellow solid.

$^1$H NMR (CDCl$_3$): δ 0.92 (t, 3H), 1.50 (s, 6H), 1.93 (q, 2H), 3.42 (s, 3H), 6.92 (bs, 1H), 7.81 (s, 1H), 7.94 (s, 1H).

MS (APCI positive): 362.0.

Example 136

(6,7-Dichloro-3-{[4-(difluoromethoxy)benzyl]sulfonyl}quinoxalin-2-yl)isopropylamine

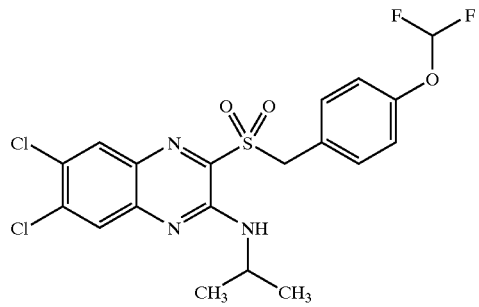

Using the procedure described in example 35, the title compound was isolated and purified by column chromatography (petroleum ether:ethyl acetate 90:10) to yield a yellow solid.

$^1$H NMR (CDCl$_3$): δ 1.19 (d, 6H), 4.22 (m, 1H), 4.77 (s, 2H), 6.26, 6.50, 6.74 (s, 1H), 6.86 (bd, 1H), 7.09 (d, 2H), 7.32 (d, 2H), 7.80 (s, 1H), 8.04 (s, 1H).

MS (APCI negative): 474.0.

Example 137

6,7-Dichloro-2-(isopropylsulfanyl)-3-(methylsulfonyl)quinoxaline

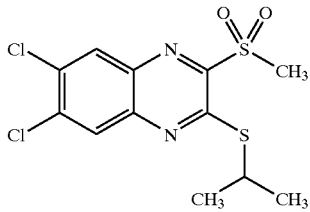

Using the procedure described in example 84 replacing 2-isopropylamine with isopropylmer-captane, the title compound was isolated and purified by column chromatography (petroleum ether:ethyl acetate 90:10).

$^1$H NMR (DMSO-$d_6$): δ 1.45 (d, 6H), 3.53 (s, 3H), 4.22 (m, 1H), 8.38 (s, 1H), 8.48 (s, 1H).

MS (APCI positive): 350.9.

Example 138

(6,7-Dichloro-3-[(1-methyl-1H-imidazol-2-yl)sulfonyl]quinoxalin-2-yl)-tert-butylamine

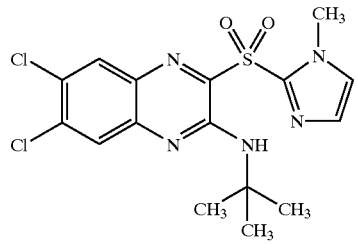

Using the procedure described in example 84, step 1 the following compound was made:

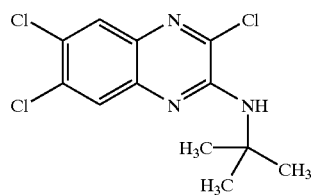

$^1$H NMR (CDCl$_3$): δ 1.56 (s, 9H), 5.62 (bs, 1H), 7.82 (s, 1H), 7.86 (s, 1H).

Using this compound and proceeding according to example 7, the title compound was isolated and purified by column chromatography (petroleum ether:ethyl acetate 80:20) to yield a yellow solid.

$^1$H NMR (CDCl$_3$): δ 1.56 (s, 9H), 4.15 (s, 3H), 7.17 (s, 1H), 7.25 (s, 1H), 7.33 (s, 1H), 7.79 (s, 1H), 7.83 (s, 1H).

MS (APCI positive): 413.9.

Example 139

(5-Chloro-3-methylsulfonyl-7-trifluoromethyl-2-quinoxalin-2-yl)-tert-butylamine

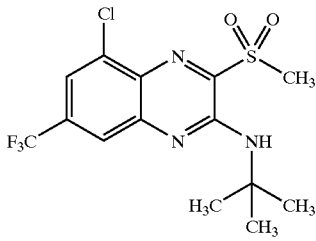

Using the procedure described in example 84, the title compound was isolated and purified by column chromatography (petroleum ether:ethyl acetate 80:20) to yield a yellow solid.

$^1$H NMR (CDCl$_3$): δ 1.62 (s, 9H), 3.45 (s, 3H), 7.20 (bs, 1H), 7.94 (s, 1H), 8.06 (s, 1H).

MS (APCI negative): 380.1.

Example 140

(6,7-Dichloro-3-nitroquinoxalin-2-yl)isopropylamine

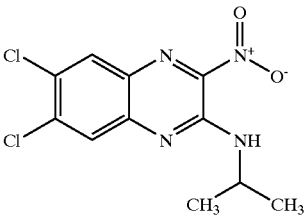

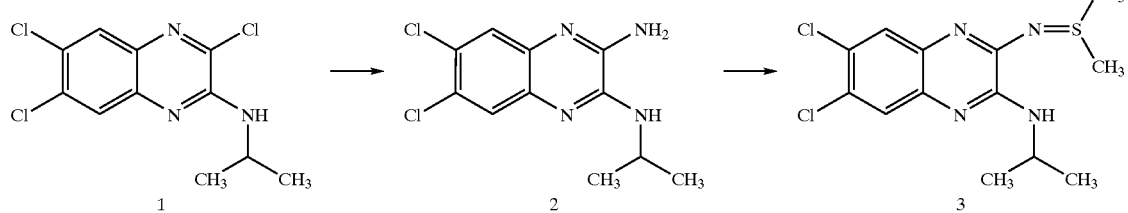

Ammonia gas was bubbled into a solution of 2,6,7-trichloro-3-(N-isopropyl)-quinoxaline (1) (1.11 mmol) (prepared as described in example 84) in DMF (30 ml) at 0° C. for 2 hours. The resulting solution was concentrated and (2) was isolated and purified by column chromatography (petroleum ether:ethyl acetate 90:10) to yield a pale yellow powder. At −78° C., trifluoromethanesulfonic acid anhydride (1.2 mmol) was added to DMSO (1.2 mmol) in dichloromethane (10 ml) under nitrogen atmosphere. To this mixture, (2) dissolved in 10 ml DMSO:dichloromethane (1:1) was added dropwise. The resulting solution was stirred overnight at room temperature. The solution was then washed with water (2×50 ml), brine, and dried over magnesium sulfate. The sulfimine (3) was isolated and purified by column chromatography (petroleum ether-ethyl acetate 75:35). (3) was oxidised with an excess of mCPBA (20 equivalents) in dichloromethane to yield the title compound, which was purified by column chromatography (petroleum ether:ethyl acetate 90:10) to yield an orange solid.

$^{1}$H NMR (CDCl$_{3}$): δ 1.35 (d, 6H), 4.49 (m, 1H), 7.45 (bs, 1H), 7.86 (s, 1H), 8.05 (s, 1H).

MS (APCI negative): 299.0.

Example 141

(3-Methylsulfonyl-6,7-dinitroquinoxalin-2-yl)-tert-butylamine

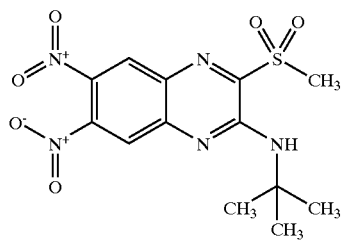

Using the procedure described in example 84, the title compound was isolated and purified by column chromatography (petroleum ether:ethyl acetate 80:20) to yield a yellow solid.

$^{1}$H NMR (CDCl$_{3}$): δ 1.56 (s, 9H), 3.46 (s, 3H), 7.43 (bs, 1H), 8.00 (s, 1H), 8.25 (s, 1H).

MS (APCI negative): 369.1.

Example 142

6,7-Dichloro-2-methanesulfonylquinoline-3-carboxylic Acid Methyl Ester

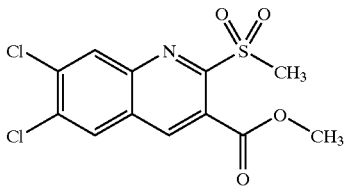

Step 1: Preparation of 2,6,7-trichloroquinoline-3-carboxylic Acid Methyl Ester

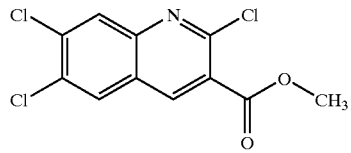

25% aqueous sodium hydroxide (75 ml) was cooled to 0° C., bromine (16.0 g, 0.1 mol) was added and the mixture was stirred to form a yellow solution of NaOBr. 4,5-Dichlorophthalimide (21.6 g, 0.1 mol) was dissolved in 5% aqueous sodium hydroxide (170 ml), the solution was cooled to 0° C. and added to the cold solution of NaOBr. The mixture was stirred vigorously for 5 min and then heated to 80° C. for 2 min. The reaction mixture was cooled and neutralised with concentrated hydrochloric acid. The precipitate was filtered off and washed with ice water. The product was recrystallised from a mixture of methanol and water. This afforded 14.8 g (72%) of 2-amino-4,5-dichlorobenzoic acid. M.p. 196–203° C.

The above 2-amino-4,5-dichlorobenzoic acid was reduced to 2-amino-4,5-dichlorobenzaldehyde according to the procedure described in: Cordi A. A.; Desos P.; Randle J. C. R.; Lepagnol J. *Bioorganic and Medicinal Chemistry* 1995 3, (2), 129–141.

Yield: 46%, m.p. 139–141° C.

The above 2-amino-4,5-dichlorobenzaldehyde was used for preparation of 6,7-dichloro-2(1H)-oxoquinoline-3-carboxylic acid methyl ester according to the procedure in: Desos P.; Lepagnol J.; Morain P., Lestage P.; Cordi A. A. *J. Med. Chem.* 1996, 39, 197–206.

Yield: 87%, m.p. >300° C.

The above ester (16.33 g, 0.05 mol) was refluxed in POCl$_{3}$ (46 ml, 0.5 mol) for 4 hours. POCl$_{3}$ was evaporated in vacuoi and the residue was mixed with ice and neutralised with sodium hydrogencarbonate. The precipitate was filtered off. The product was crystallised from tetrahydrofuranto yield 10.6 g (73%) of 2,6,7-trichloroquinoline-3-carboxylic acid methyl ester, m.p. 178.5–180° C.

$^{1}$H NMR (CDCl$_{3}$): δ 3.97 (s, 3H), 8.20 (s, 1H); 8.42 (s, 1H), 8.84 (s, 1H).

Calculated for C$_{11}$H$_{6}$Cl$_{3}$NO$_{2}$: C, 45.48%; H, 2.08%; N, 4.82%; Cl, 36.61%; Found: C, 45.18%; H, 2.30%; N, 4.75%; Cl, 36.51%.

Step 2: Preparation of 6,7-dichloro-2-methanesulfonylquinoline-3-carboxylic Acid Methyl To a suspension of 2,6,7-trichloroquinoline-3-carboxylic acid methyl ester (1 g, 3.44 mmol) in DMF (20 ml) was added sodium methanesulfinate (1.05 g, 10.3 mmol). The reaction mixture was stirred at 100° C. for 1 hour under nitrogen. The cooled mixture was partitioned between diethyl ether and water. The organic layer was separated and evaporated and the residue purified by flash column chromatography using dichloromethane:ethyl acetate (gradient) followed by recrystallisation from ethanol to yield 417 mg (36%) of the title compound as a white solid.

$^{1}$H NMR (CDCl$_{3}$): δ 3.48 (s, 3H), 4.05 (s, 3H), 8.10 (s, 1H), 8.37 (s, 1H), 8.59 (s, 1H).

MS (APCI (M+H)$^{+}$) m/z 335.

Calculated for C$_{12}$H$_{9}$Cl$_{2}$NO$_{4}$S: C, 43.13%; H, 2.71%; N, 4.19%; Found: C, 43.17%; H, 2.73%; N, 4.16%;

Example 143

6-Chloro-7-methylsulfanyl-2-(5-methyl-1,3,4-thiadiazol-2-ylsulfanyl)-3-trifluoromethyl-quinoxaline

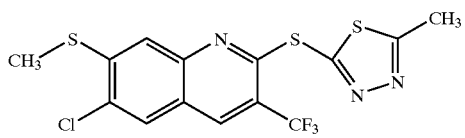

A mixture of 6-chloro-7-fluoro-3-trifluoromethyl-quinoxalin-2-ol and 7-chloro-6-fluoro-3-trifluoromethyl-quinoxalin-2-ol (4.1 g, prepared similarly as described above from 4-chloro-5fluoro-1,2-diaminobenzene and ethyl trifluoropyruvate) was dissolved in DMF (140 ml) and sodium hydrogen sulfide monohydrate (3.5 g, 47 mmol) was added. The reaction mixture was stirred at room temperature for 1 hour and then iodomethane (3.5 ml) was added. Stirring was continued for 10 minutes and the reaction mixture was poured on ice/water (500 ml). The separated crystals were filtered, dried and recrystallised from ethanol to afford 1.73 g (38%) of 6-chloro-7-methylsulfanyl-3-trifluoromethyl-1H-quinoxalin-2-one.

$^1$H NMR (DMSO-$d_6$): δ 2.58 (s, 3H), 7.18 (s, 1H), 8.02 (s, 1H), 13.02 (br s, 1H).

MS (APCI positive) m/z 294.

Preparation of 6-chloro-7-methylsulfanyl-2-(5-methyl-1,3,4-thiadiazol-2-ylsulfanyl)-3-trifluoromethylquinoxaline 2,6-Dichloro-7-methylsulfanyl-3-trifluoromethylquinoxaline (116 mg, 0.37 mmol, prepared similarly as described above from 6-chloro-7-methylsulfanyl-3-trifluoromethyl-1H-quinoxaline-2-one, dimethylaminopyridine and POCl$_3$) and 2-mercapto-5-methyl-1,3,4-thiadiazole (146 mg, 1.1 mmol) was dissolved in DMF (3.3 ml). Potassium carbonate (20 mg) was added and the reaction mixture was stirred at 50° C. for 2 hours. The cooled mixture was partitioned between diethyl ether and water. The organic layer separated, evaporated and the residue recrystallised from ethanol to afford 80 mg (50%) of the title compound as a yellow solid.

$^1$H NMR (CDCl$_3$): δ 2.64 (s, 3H), 2.92 (s, 3H), 7.50 (s, 1H), 8.15 (s, 1H).

MS (APCI (M+H)$^+$) m/z 409.

Example 144

2-Methyl-6,7-dinitro-3-phenylquinoxaline

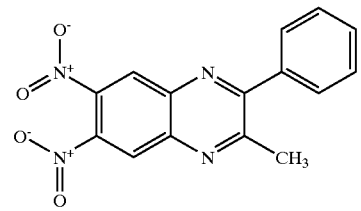

4,5-Dinitro-1,2-phenylenediamine (890 mg, 4.5 mmol) (G. W. H. Cheeseman, J. Org. Soc. 1170–5, 1962) was mixed with 1-phenyl-1,2-propanedione (800 mg, 5.4 mmol) in ethanol (18 ml). The mixture was heated to reflux for 4 hours. The ethanol was removed by evaporation and the remaining brown oil was suspended in dichloromethane (20 ml). Purification by column chromatography on silica gel eluting with dichloromethane followed by recrystallisation from ethanol yielded the title compound (200 mg, 14%).

$^1$H NMR (CDCl$_3$): δ 2.91 (s, 3H), 7.60 (m, 3H), 7.72 (m, 2H), 8.60 (s, 1H), 8.66 (s, 1H).

Example 145

6,7-Dinitro-2-phenyl-3-trifluoromethylquinoxaline

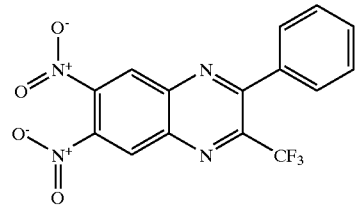

The title compound was prepared from 4,5-dinitro-1,2-phenylenediamine (890 mg, 4.5 mmol) and 3,3,3-trifluoro-1-phenyl-1,2-propanedione hydrate (1 g, 4.9 mmol) similarly as described in example 144.

$^1$H NMR (CDCl$_3$): δ 7.56 (m, 3H), 7.68 (m, 2H), 8.63 (s, 1H), 8.89 (s, 1H).

Example 146

6,7-Dinitro-2-(4-trifluoromethoxyphenyl)quinoxaline

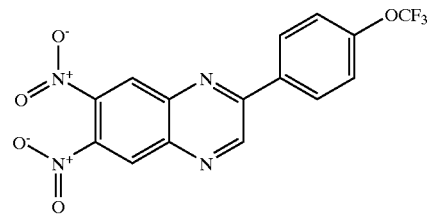

4,5-Dinitro-1,2-phenylenediamine (890 mg, 4.5 mmol) and 4-trifluoromehtoxyphenylacyl bromide (1.5 g, 5.4 mmol) were mixed in ethanol (18 ml). The mixture was heated at reflux. After 1 hour N-ethyldiisopropylamine (0.5 ml) was added and the reaction mixture refluxed for 3 more hours. A second amount of N-ethyldiisopropylamine (0.2 ml) was added followed by reflux for 1 hour. The ethanol was removed by evaporation and the remaining brown oil was suspended in dichloromethane (20 ml). Purification by column chromatography on silica gel eluting with dichloromethane followed by recrystallisation from ethanol yielded the title compound (413 mg, 28%).

$^1$H NMR (CDCl$_3$): δ 7.48 (d, 2H), 8.34 (d, 2H), 8.68 (s, 1H), 8.72 (s, 1H), 9.58 (s, 1H).

Example 147

6,7-Dinitro-2-(4-trifluoromethylphenyl)quinoxaline

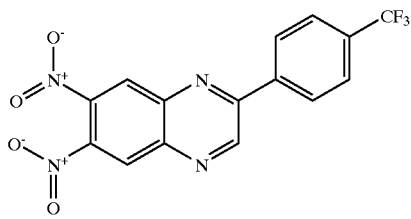

Prepared similarly as described in example 146 from 4,5-dinitro-1,2-phenylenediamine (890 mg, 4.5 mmol) and 4-(trifluoromethyl)phenylacyl bromide (1.44 g, 5.4 mmol) to yield the title compound (50 mg, 3%).

$^1$H NMR (CDCl$_3$): δ 7.90 (d, 2H), 8.41 (d, 2H), 8.72 (s, 1H), 8.75 (s, 1H), 9.63 (s, 1H).

Example 148

4-(6,7-Dinitroquinoxalin-2-yl)benzonitril

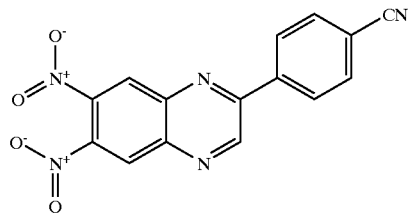

Prepared similarly as described in example 146 from 4,5-dinitro-1,2-phenylenediamine (890 mg, 4.5 mmol) and 4-cyanophenylacyl bromide (1.21 g, 5.4 mmol) to yield the title compound.

$^1$H NMR (CDCl$_3$): δ 7.92 (d, 2H), 8.42 (d, 2H), 8.73 (s, 1H), 8.75 (s, 1H), 9.62 (s, 1H).

Example 149

2-(3,4-Dichlorophenyl)-6,7-dinitroquinoxaline

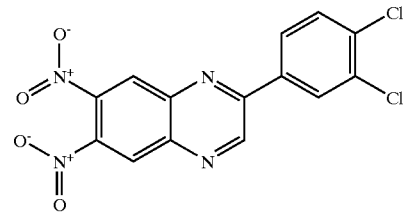

The oxidation of 3,4-dichloroacetophenone is a modification of a general procedure described in: Floyd M. B.; Du M. T.; Fabio P. F.; Jacob, L. A.; Johnson, B. D. *J. Org. Chem.* 1985 50, (25), 5022–5027.

48% aqueous HBr (8.8 M) (3.4 ml, 30 mmol) was slowly added to a stirred solution of 3,4-dichloroacetophenone (1.89 g, 10 mmol) in DMSO (17 ml). The solution was stirred in an open flask at 55° C. for 24 hours. The solution was poured onto ice, the solid product was filtered, washed with water, and redissolved in ethanol (18 ml). 4,5-Dinitro-1,2-phenylene-diamine (890 mg, 4.5 mmol) was added and the mixture was heated to reflux for 4 hours.

The ethanol was removed by evaporation and the remaining brown oil was suspended in dichloromethane (20 ml). Purification by column chromatography on silica gel eluting with dichloromethane followed by recrystallisation from ethanol yielded the title compound (70 mg, 4%).

$^1$H NMR (CDCl$_3$): δ 7.70 (d, 1H), 8.12 (dd, 1H), 8.42 (d, 1H), 8.70 (s, 1H), 8.74 (s 1H), 9.58 (s, 1H).

Example 150

2-(3,5-Bis-trifluoromethylphenyl)-6,7-dinitroquinoxaline

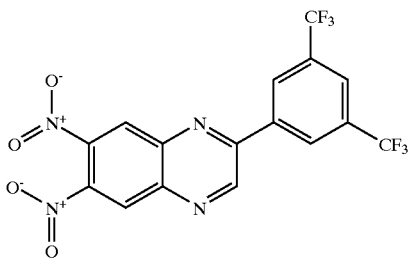

Prepared similarly as described in example 149 from 3,5-bis-(trifluoromethyl)acetophenone (2.56 g, 10 mmol) and 4,5-dinitro-1,2-phenylenediamine (890 mg, 4.5 mmol) to yield 200 mg (10%) of the title compound.

$^1$H NMR (CDCl$_3$): δ 8.15 (s, 1H), 8.74 (s, 2H), 8.78 (s, 1H), 8.80 (s, 1H), 9.60 (s, 1H).

Example 151

(3-Bromo-2-trifluoromethylquinoxalin-6-yl)phenyl Methanone

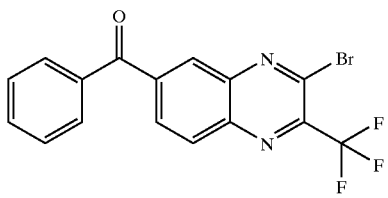

A mixture of 7-benzoyl-3-trifluoromethylquinoxalin-2 (1H)-one (3.0 g, 9.4 mmol) [*J. Org. Chem.* 57(21), 5630, 1992] and 40 ml of phosphorous tribromide was refluxed for 5 hours. The mixture was cooled and poured into ice water and the precipitate was isolated. The crude solid was dissolved in a mixture of diethylether and ethyl acetate (1:1), followed by addition of Norite A and anhydrous magnesium sulfate. The mixture was filtered and the solvent evaporated under reduced pressure. The residue was triturated with hexane, filtered off and dried to yield 1.9 g (53%) of the title compound as a pale yellow solid.

M.p. 152–54° C. $^1$H NMR (DMSO-d$_6$): δ 7.56–7.90 (m, 5H), 8.29 (dd, 1H), 8.38 (d, 1H), 8.44 (d, 1H).

Example 152

[3-(5-Methyl-[1,3,4]thiadiazol-2-ylsulfanyl)-2-trifluoromethylquinoxalin-6-yl]phenyl Methanone

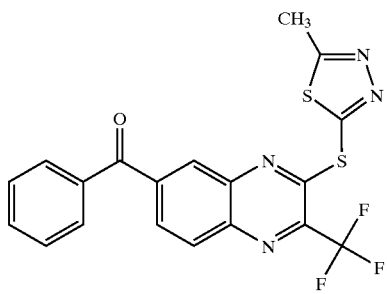

A mixture of (3-bromo-2-trifluoromethylquinoxalin-6-yl) phenyl methanone (144 mg, 0.299 mmol), 2-mercapto-5-methylthiadiazole (38 mg, 0.28 mmol) and caesium fluoride (55 mg, 0.36 mmol) in DMF (1.5 ml) was stirred for 16 hours at room temperature. The reaction mixture was purified by preparative HPLC (Gilson) to yield 35 mg (27%) of the title compound as a pale yellow solid.

M.p. 176–9° C. $^1$H NMR (DMSO-$d_6$): δ 2.82(s, 3H) 7.57–7.88 (m, 1H), 8.19 (dd, 5H), 8.30 (d, 1H), 8.43 (d, 1H).

Example 153

2-(5-Methyl-[1,3,4]thiadiazol-2-yl-sulfanyl)-3-trifluoromethylquinoxaline-6-carboxylic Acid Methyl Ester

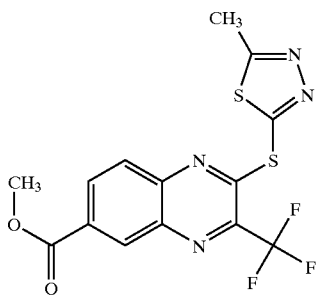

Step 1:
A mixture of methyl 3,4-diaminobenzoate (7.8 g, 46.9 mmol), ethyl trifluoropyruvate (8.0 g, 47.3 mmol) and a catalytic amount of p-toluenesulfonic acid in 100 ml of methanol was heated and stirred until no starting material could be detected by monitoring on TLC. The mixture was cooled to 50° C. and water was added until incipient precipitation. The precipitate was filtered off, washed with water and dried to yield 11.9 g (93%) of a 4:1 mixture of 2-oxo-3-trifluoromethyl-1,2-dihydro-quinoxaline-7-carboxylic acid methyl ester and 2-oxo-3-trifluoro-methyl-1,2-dihydroquinoxaline-6-carboxylic acid methyl ester, respectively.

Step 2:
The above isomeric mixture (2.0 g, 7.35 mmol) was brominated in analogy with the method outlined in example 151 to afford 1.69 g (69%) of a 4:1 mixture of 3-bromo-2-trifluoro-methylquinoxaline-6-carboxylic acid methyl ester and 2-bromo-3-trifluoromethyl-quinoxaline-6-carboxylic acid methyl ester, respectively.

Step 3:
The above mixture of bromides (1.32 g, 3.94 mmol) was reacted with 2-mercapto-5-methyl-thiadiazole in analogy with the method outlined in example 152 to afford the title compound as white needles.

M.p. 151–2° C. $^1$H NMR (CDCl$_3$): δ 2.94 (s, 3H) 4.05 (s, 3H) 8.05 (d, 1H), 8.48 (dd, 1H), 8.89 (d, 1H).

Example 154

3-Methanesulfonyl-2-trifluoromethylquinoxaline-6-carboxylic Acid Methyl Ester

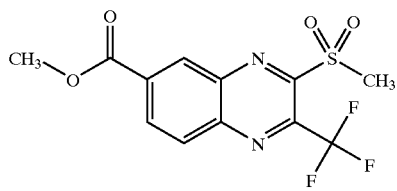

To a solution of a 4:1 mixture of 3-bromo-2-trifluoromethylquinoxaline-6-rboxylic acid methyl ester and 2-bromo-3-trifluoromethylquinoxaline-6-carboxylic acid methyl ester, respectively (0.3 g, 0.895) (see example 153, step 2) in 1 ml of DMF was added methanesulfinic acid, sodium salt (22 mg, 1.83 mmol). The reaction mixture was stirred at room temperature for two hours. Purification by HPLC afforded the title compound as a white solid.

M.p. 143–4° C. $^1$H NMR (DMSO-$d_6$): δ 3.67 (s, 3H), 4.02 (s, 3H), 8.50 (d, 1H), 8.60 (dd, 1H), 8.78 (d, 1H).

Example 155

2-Benzoxazol-2-yl-6,7-Dichloro-3-trifluoromethylquinoxaline

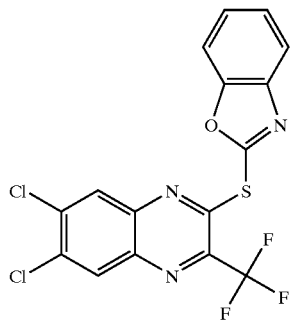

The title compound was prepared from 2-bromo-6,7-dichloro-3-trifluoromethylquinoxaline and 2-mercaptobenzoxazole in analogy with the method outlined in example 1.

M.p. 157–8° C. $^1$H NMR (DMSO-$d_6$): δ 7.43 7.58 (m, 2H), 7.78–7.90 (m, 2H), 8.20 (s, 1H), 8.78(s, 1H).

Example 156

6,7-Dichloro-2-(thiazol-2-ylsulfanyl)-3-trifluoromethyl-quinoxaline

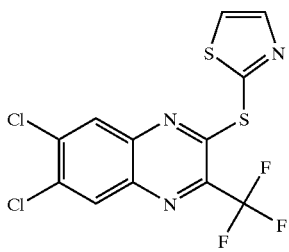

The title compound was prepared from 2-bromo-6,7-dichloro-3-trifluoromethylquinoxaline and 2-mercaptothiazole in analogy with the method outlined in example 1.

$^1$H NMR (DMSO-d$_6$): δ 8.08 (d, 1H), 8.12 (d, 1H), 8.38 (s, 1H), 8.67 (s, 1H).

Example 151

(2-Bromo-3-trifluoromethyl-quinoxalin-6-yl)phenyl Methanone

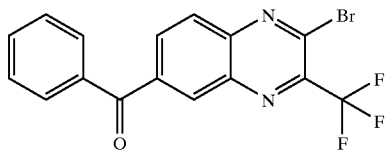

A mixture of 6-benzoyl-3-trifluoromethylquinoxalin-2(1H)-one (1.0 g, 3.13 mmol) [J. Org. Chem. 57(21). 5630, 1992] and 10 ml of phosphorous tribromide was refluxed for 5 hours. The mixture was cooled and poured into ice water and the precipitate was isolated, washed with water and dried. Yield 0.87 g (73%) of the title compound as beige crystals.

M.p. 124–6° C. $^1$H NMR (CDCl$_3$): δ 7.50–7.90 (m, 5H), 8.25 (d, 1H), 8.42 (dd, 1H), 8.57 (d, 1H).

Example 158

[2-(5-Methyl-[1,3,4]thiadiazol-2-ylsulfanyl)-3-trifluorophenylquinoxalin-6-yl]phenyl Methanone

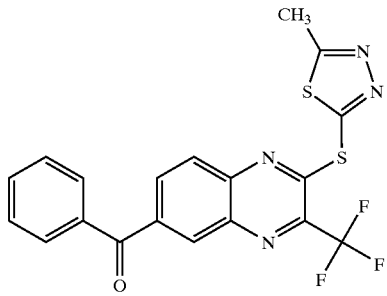

A mixture of (2-bromo-3-trifluoromethylquinoxalin-6-yl) phenyl methanone (100 mg, 0.263 mmol), 2-mercapto-5-methylthiadiazole (40 mg, 0.30 mmol) and caesium fluoride (54 mg, 0.36 mmol) in 1.0 ml of DMF was stirred for 16 hours at room temperature. The reaction mixture was purified by preparative HPLC (Gilson) to yield 44 mg (38%) of the title compound as a pale yellow solid.

M.p. 160–2° C. $^1$H NMR (DMSO-d$_6$): δ 2.78(s, 3H) 7.60–7.90 (m, 5H), 8.25 (d, 1H), 8.38 (dd, 1H), 8.44 (d, 1H).

Analysis: Calculated for C$_{19}$H$_{11}$F$_3$N$_4$O$_1$S$_2$: C, 52.77; H, 2.56; N, 12.96%. Found: C, 52.56; H, 2.51; N, 12.89%.

Example 159

6,7-Dichloro-2-methanesulfonyl-3-methoxyquinoxaline

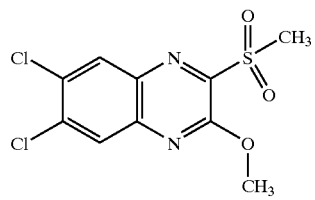

Triethyl amine (210 mg, 2 mmol) was added to a suspension of 2,3,5,6-tetrachloroquinoxaline (268 mg, 1 mmol) in methanol (25 ml). The reaction mixture was heated at reflux for 6 hours, cooled to room temperature and filtered. The filtrate was dissolved in DMF (20 ml). To this solution were added sodium hydrosulfide hydrate (56 mg, 0.75 mmol) and potassium carbonate (100 mg). The reaction mixture was stirred at room temperature for 0.5 hours. Iodomethane (131 mg, 1 mmol) was added, and the mixture was stirred for 10 min. Water (100 ml) was added and the water phase was extracted with dichloromethane (3×30 ml). The organic extracts were dried and evaporated and filtered through a short silica column with dichloromethane:hexane (1:20). The organic phase was evaporated and the residue was dissolved in dichloromethane (15 ml). 3-Chloroperoxybenzoic acid (100 mg) was added and the reaction mixture was stirred at room temperature for 190 min. Dichloromethane was evaporated and the residue was dissolved in ether (40 ml). The organic phase was washed with a saturated sodium hydrogen carbonate solution (3×20 ml), dried over magnesium sulfate and evaporated. Hexane (5 ml) was added to the residue and the title compound was filtered off and dried. Yield 30 mg, M.p. 216–9° C.

Example 160

6,7-Dichloro-3,4-dihydro-2H-1-thia-9,10-diaza-anthracene 1,1-dioxide

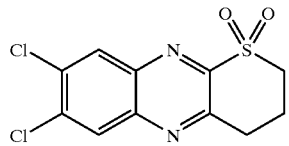

Step 1:
1,2-Diamino-4,5-dichlorobenzene (1.63 g, 9.22 mmol), dissolved in a small amount of DMF, as added dropwise to a stirred solution of 5-chloro-2-oxo-pentanoic acid ethyl ester (1.50 g, 9.22 mmol) [J. H. Hoare, P. Yates *J. Org. Chem.* 1983, 4, 3333] in a mixture of DMF:glacial acetic acid 7:3 (5 ml). After stirring for 3 days at room temperature, the solvent was removed in vacuo leaving a dark coloured solid. Ethyl acetate was added and the insoluble material was removed by filtration over a short pad of silica. The filtrate was evaporated in vacuo, and the residue was purified by flash column chromatography (ethyl acetate:heptane 25:75), to yield 25% of 6,7-dichloro-3-(3-chloropropyl)-1H-quinoxalin-2-one as a yellow solid.

$^1$H NMR (DMSO-d$_6$): δ 2.21 (quintet, 2H), 2.95 (t, 2H), 3.74 (t, 2H), 7.42 (s, 1H), 7.88 (s, 1H), 12.45 (br.s, 1H).
Step 2:
6,7-Dichloro-3-(3-chloropropyl)-1H-quinoxalin-2-one (0.68 g, 2.33 mmol) was added to POCl$_3$ (10 ml) and the resulting mixture was heated under reflux for 0.5 hours. The reaction mixture was poured onto ice and extracted with dichloromethane (3×). The combined organic layers were dried over anhydrous sodium sulfate, filtered and evaporate in vacuo. The resulting oil was purified by flash column chromatography (dichloromethane) to yield 21% of 2,6,7-trichloro-3-(3-chloropropyl)quinoxaline as a colourless oil.

$^1$H NMR (CDCl$_3$): δ 2.41 (quintet, 2H), 3.29 (t, 2H), 3.75 (t, 2H), 8.07 (s, 1H), 8.14 (s, 1H).
Step 3:
To a solution of 2,6,7-trichloro-3-(3-chloropropyl) quinoxaline (0.15 g, 0.48 mmol) in dry DMF (50 ml) were added sodium hydrosulfide (0.11 g, 1.44 mmol) and potassium carbonate (0.20 g, 1.45 mmol). The reaction mixture was stirred for 4 days at room temperature. The solvent was evaporated in vacuo, followed by the addition of water. The resulting mixture was extracted with dichloromethane (3×). The combined organic layers were dried over anhydrous sodium sulfate, filtered and evaporated in vacuo to yield 6,7-dichloro-3,4-dihydro-2H-1-thia-9,10-diaza-anthracene (>100%) as a solid.

$^1$H NMR (CDCl$_3$): δ 2.36 (quintet, 2H), 3.18 (t, 2H), 3.28 (t, 2H), 7.94 (s, 1H), 7.98 (s, 1H).
MS (APCI (M+H)$^+$) m/z 271.0.
Step 4:
To a solution of 6,7-dichloro-3,4-dihydro-2H-1-thia-9,10-diaza-anthracene (0.15 g, 0.55 mmol) in dichloromethane (10 ml) was added 3-chloroperoxybenzoic acid (0.23 g, 1.16 mmol). The reaction mixture was stirred overnight at room temperature. The solvent was removed in vacuo. The product was purified by flash column chromatography using ethyl acetate:petroleum ether 1:1. After evaporation of the solvent, the residue was redissolved in dichloromethane and washed with sat. aqueous NaHCO$_3$. The organic layer was evaporated to yield 31% of the title compound as a grey solid, which was washed with methanol, water and acetone, respectively.

$^1$H NMR (DMSO-d$_6$): δ 2.47 (m, 2H), 3.37 (t, 2H), 3.84 (m, 2H), 8.46 (s, 1H), 8.62 (s, 1H).
MS APCI (M+1)$^+$ m/z 303.0, (2M+Na)$^+$ m/z 629.0.

Example 161

Ethyl 6,7-dinitro-3-(2-pyridinyl)-2-quinoxalinecarboxylate

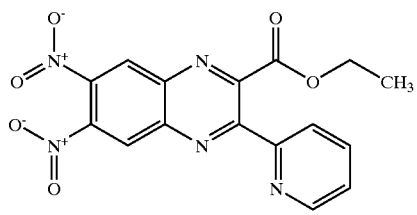

To a solution of ethyl picolinoylacetate (5.17 mmol) in dioxane (30 ml) was added selenium dioxide (1.5 equivalents). The resulting solution was heated to reflux for 3 hours. The solvent was concentrated and the resulting oil was redissolved in ethyl acetate and washed with water (2×), brine, and dried over magnesium sulfate. The desired product was used directly in the condensation reaction previously described in example 144 to give the title compound as a beige solid. Isolation and purification was achieved by flash column chromatography (ethyl acetate:petroleum ether 20:80).

$^1$H NMR (DMSO-d$_6$): δ 1.27 (t, 3H), 4.43 (q, 2H), 7.69 (m, 1H), 8.17 (m, 1H), 8.48 (d, 1H), 8.76 (m, 1H), 9.14 (d, 2H).
MS (APCI positive): 370.0.

Example 162

6,7-Dinitro-2-(4-nitrophenyl)-3-trifluoromethyl) quinoxaline

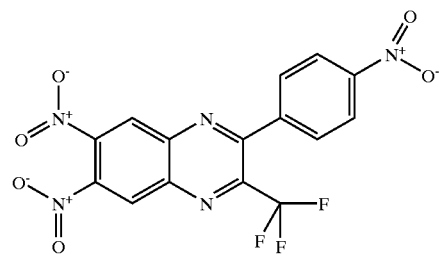

To a solution of (6,7-dinitro-2-chloro-3-trifluoromethyl) quinoxaline in toluene under a nitrogen atmosphere was added potassium carbonate (0.958 mmol), 4-nitrophenylboronic acid (0.958 mmol), and 10% tetrakis (triphenylphosphine)palladium(0). The resulting mixture was heated at reflux overnight. The toluene was concentrated and the resulting residue was resuspended in ethyl acetate and filtered through a celite cake. Isolation and purification by flash column chromatography yielded the title compound as an off white solid.

$^1$H NMR (CDCl$_3$): δ 7.85 (d, 2H), 8.43 (d, 2H), 8.77 (s, 1H), 8.90 (s, 1H).
MS (APCI negative): 409.1.

Example 163

2-[2,4-Bis(trifluoromethyl)phenyl]-6,7-dinitro-3-(trifluoromethyl)quinoxaline

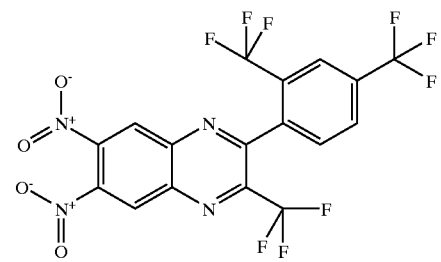

Using the procedure described in example 162, the title compound was obtained as a cream coloured solid upon isolation and purification by flash column chromatography (ethyl acetate:petroleum ether 30:70).

$^1$H NMR (DMSO-d$_8$): δ 8.14 (d, 1H), 8.44 (m, 2H), 9.30 (s, 1H), 9.45 (s, 1H).
MS (APCI negative): 500.0.

Example 164

2-[3,5-Bis(trifluoromethyl)phenyl]6,7-dinitro-3-(trifluoromethyl)quinoxaline

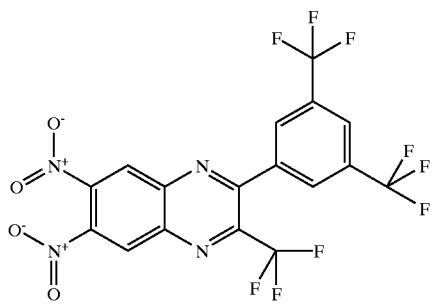

Using the procedure described in example 162, the title compound was obtained as an off white solid upon isolation and purification by flash column chromatography (ethyl acetate:petroleum ether 20:80).

$^1$H NMR (DMSO-d$_6$): δ 8.30 (bs, 3H), 9.13 (s, 1H), 9.22 (s, 1H).

MS (APCI negative): 500.0.

Example 165

Ethyl 3-[3,5-bis(trifluoromethyl)phenyl]-6,7-dinitro-2-quinoxaline Carboxylate

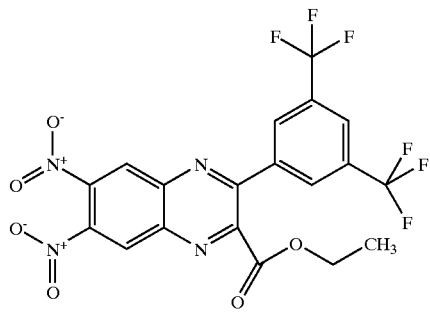

Using the procedure described in example 162, the title compound was obtained as an off white solid upon isolation and purification by preparative HPLC.

$^1$H NMR (CDCl$_3$): δ 1.36 (t, 3H), 4.49 (q, 2H), 8.13 (s, 1H), 8.29 (s, 2H), 8.81 (s, 1H), 8.85 (s, 1H).

MS (APCI negative): 504.0.

Example 166

Ethyl 6,7-dinitro-3-(4-nitrophenyl)-2-quinoxaline Carboxylate

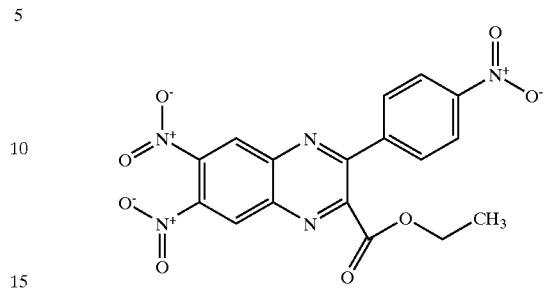

Using the procedure described in example 162, the title compound was obtained upon isolation and purification by flash column chromatography (ethyl acetate:petroleum ether 20:80).

$^1$H NMR (CDCl$_3$): δ 1.23 (t, 3H), 4.32 (q, 2H), 7.89 (d, 2H), 8.31 (d, 2H), 8.64 (s, 1H), 8.72 (s, 1H).

MS (APCI negative): 413.1.

Example 167

6,7-Dinitro-2-(2-nitrophenyl)-3-(trifluoromethyl)quinoxaline

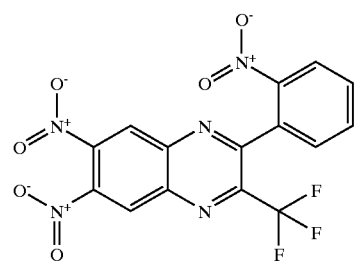

Using the procedure described in example 162, the title compound was obtained as a mustard yellow solid upon isolation and purification by preparative HPLC.

$^1$H NMR (DMSO-dB): δ 7.92 (m, 1H), 8.01 (m, 1H), 8.11 (m, 1H), 8.49 (d, 1H), 9.24 (s, 1H), 9.41 (s, 1H).

MS (APCI negative): 409.0.

Example 168

Methyl 4-[6,7-dinitro-3-(trifluoromethyl)-2-quinoxalinyl]-3-nitrobenzoate

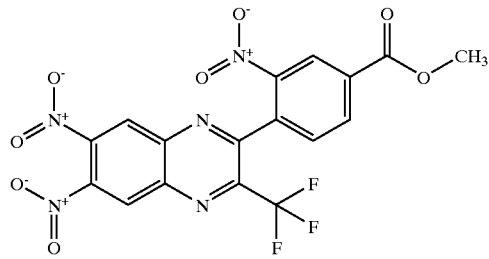

Using the procedure described in example 162, the title compound was obtained as an off white solid upon isolation and purification by preparative HPLC.

$^1$H NMR (CDCl$_3$): δ 4.08 (s, 3H), 7.66 (d, 1H), 8.55 (d, 1H), 8.70 (s, 1H), 8.94 (s, 1H), 9.05 (s, 1H).
MS (APCI negative): 467.1.

Example 169

6-Chloro-3-(3-methylbutylsulfonyl)-2-trifluoromethyl-quinoxaline

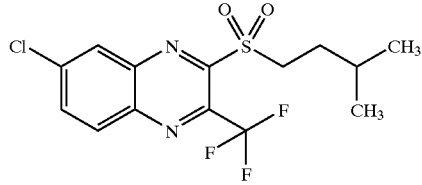

The starting material 3,6-dichloro-2-trifluoromethylquinoxaline was prepared according to the general method (A) and further reacted in analogy with the synthetic principles outlined in example 20.

$^1$H NMR (CDCl$_3$): δ 1.02 (d, 6H), 1.80 (m, 3H), 3.75 (m, 2H), 8.00 (dd, 1H), 8.23 (dd, 1H), 8.25(d, 1H).

Example 170

6-Chloro-2-(3-methylbutyl-1-sulfonyl)-3-trifluoromethyl-quinoxaline

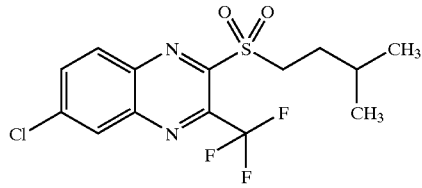

The starting material 2,6-dichloro-3-trifluoromethylquinoxaline was prepared according to the general method (A) and further reacted in analogy with the synthetic principles outlined in example 20.

$^1$H NMR (DMSO-d$_6$): δ 0.93 (d, 6H), 1.70 (m, 3H), 3.87 (m, 2H), 8.26 (dd, 1H), 8.39 (d, 1H), 8.59 (d, 1H).

Analysis: Calculated for C$_{14}$H$_{14}$ClF$_3$N$_2$O$_2$S: C, 45.85; H, 3.85; N, 7.64; S 8.74; Cl; 9.67%. Found: C, 45.96; H, 3.80; N, 7.58; S 9.04; Cl; 9.92%.

Example 171

6-Chloro-2-(3-methylbutylsulfonyl)quinoxaline

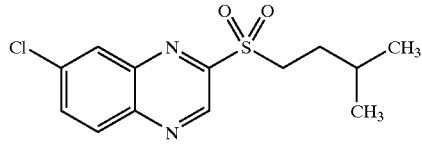

The starting material 2,7-dichloroquinoxaline was prepared according to the general method (A) and further reacted in analogy with the synthetic principles outlined in example 20.

M.p. 120–1° C. $^1$H NMR (CDCl$_3$): δ 0.92 (d, 6H), 1.70 (m, 3H), 3.5z5 (m, 2H), 7.90 (dd, 1H), 8.20 (d, 1H), 8.28 (dd, 1H).

Analysis: Calculated for C$_{13}$H$_{15}$ClN$_2$O$_2$S: C, 52.26; H, 5.06 N, 9.38%. Found: C, 52.42; H, 5.03 N, 9.31%.

In a similar way as described in the foregoing examples the following compounds may be prepared:

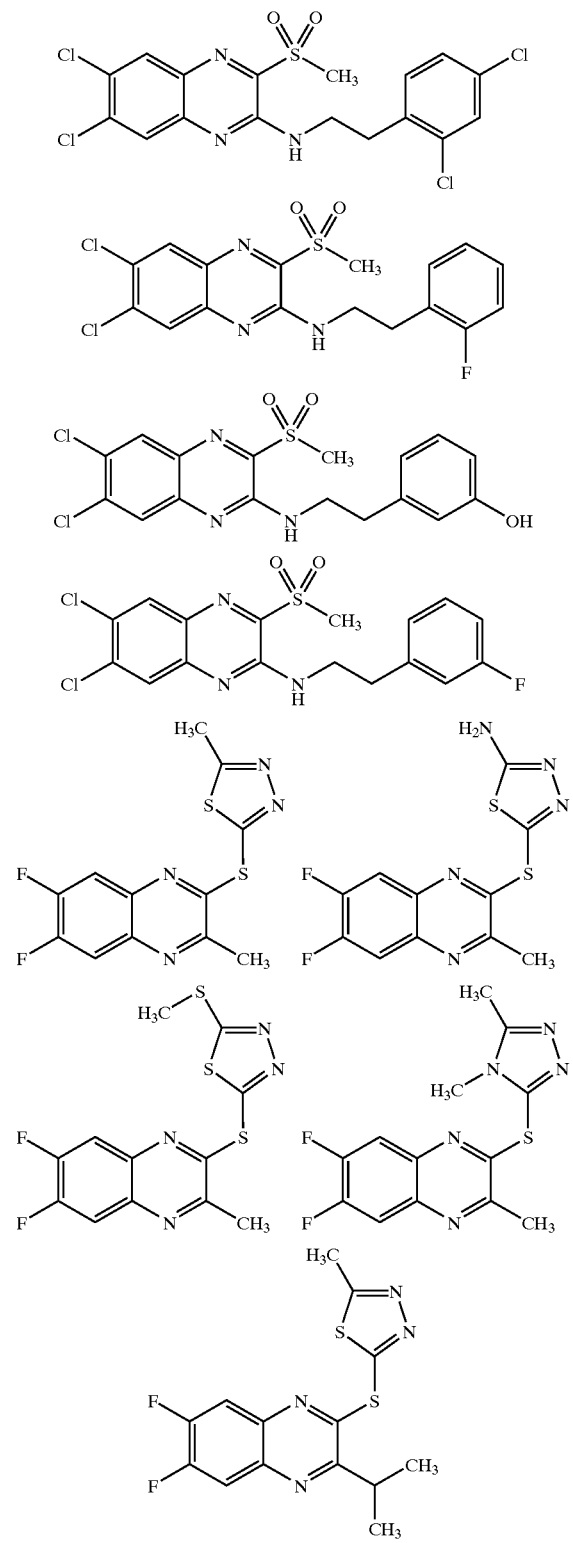

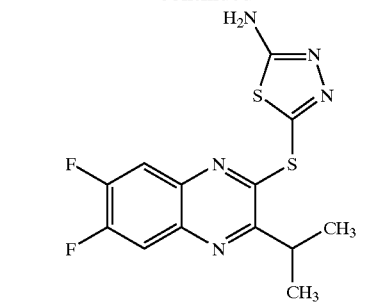
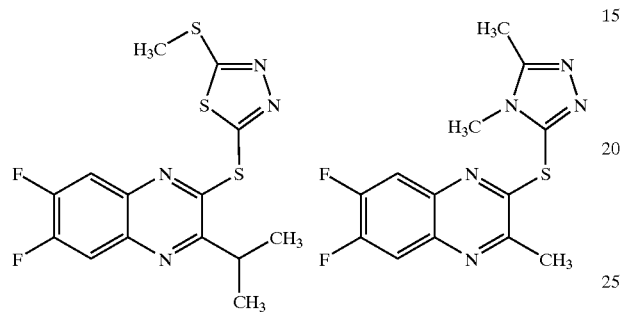
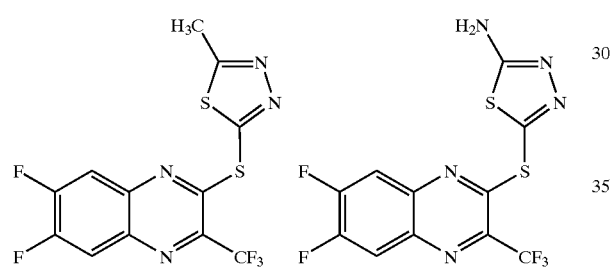
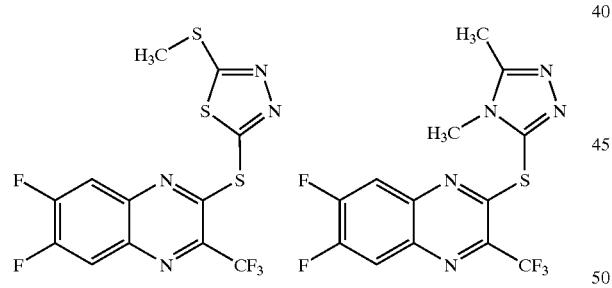
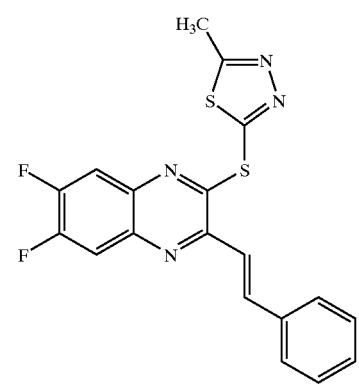
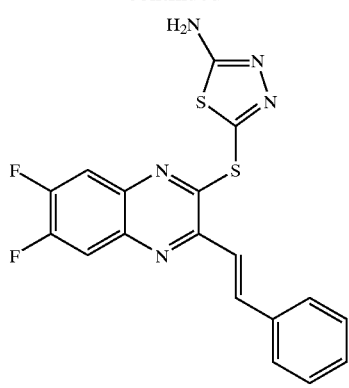
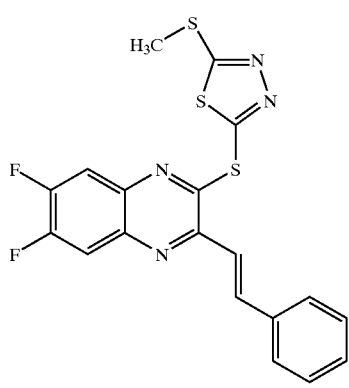
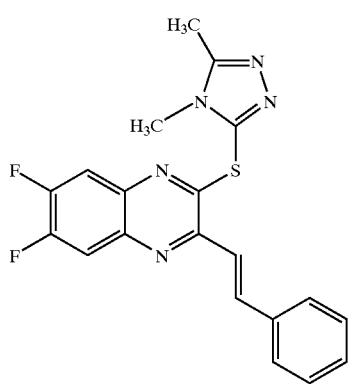
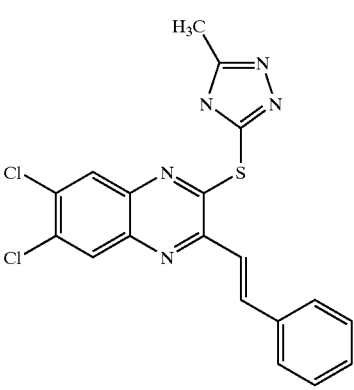

115
-continued
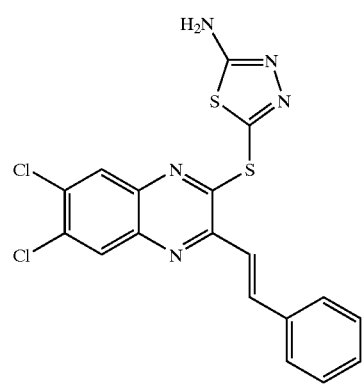
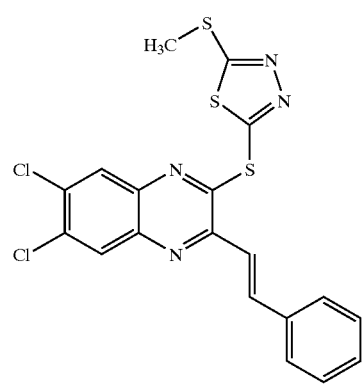
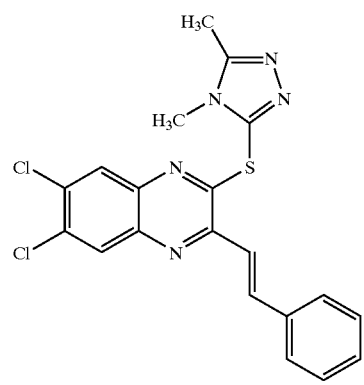
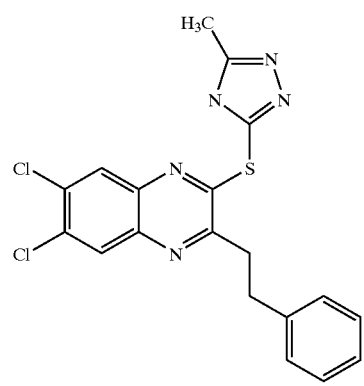
116
-continued
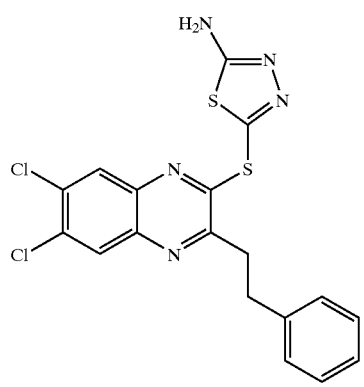
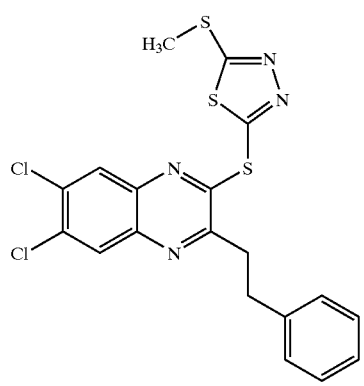
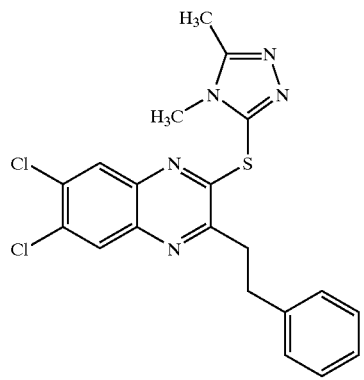
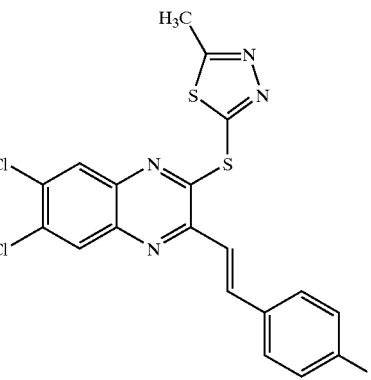

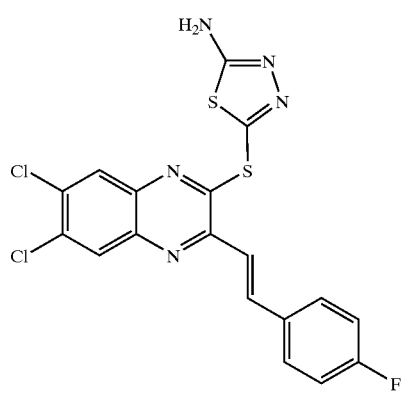
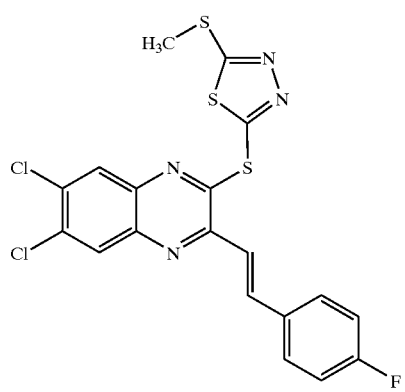
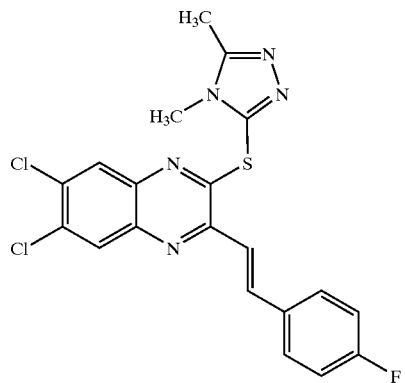
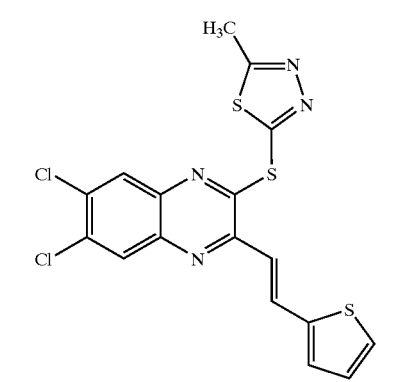
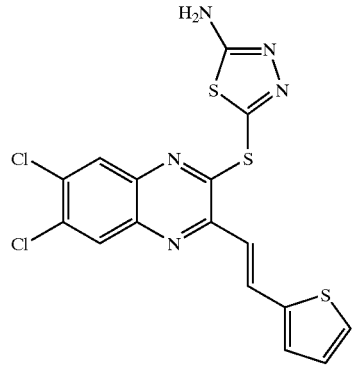
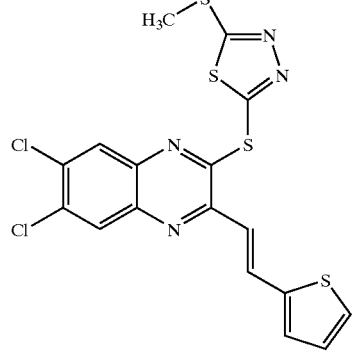
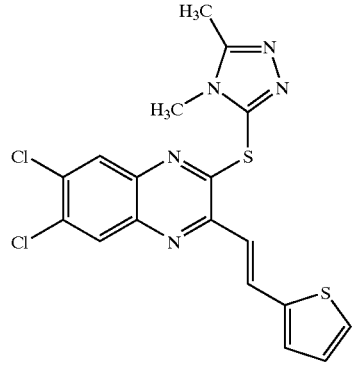
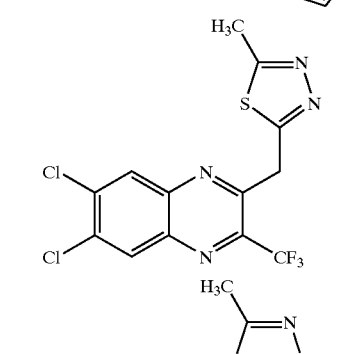
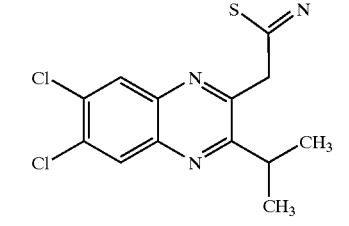

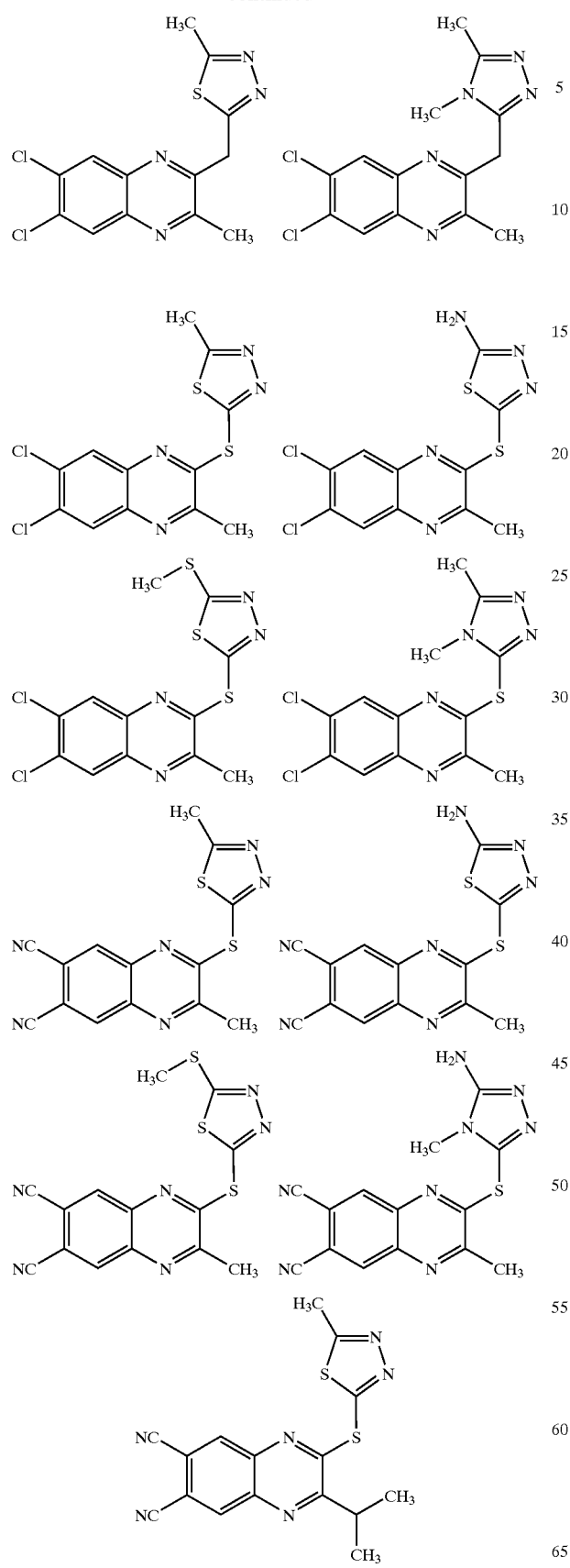
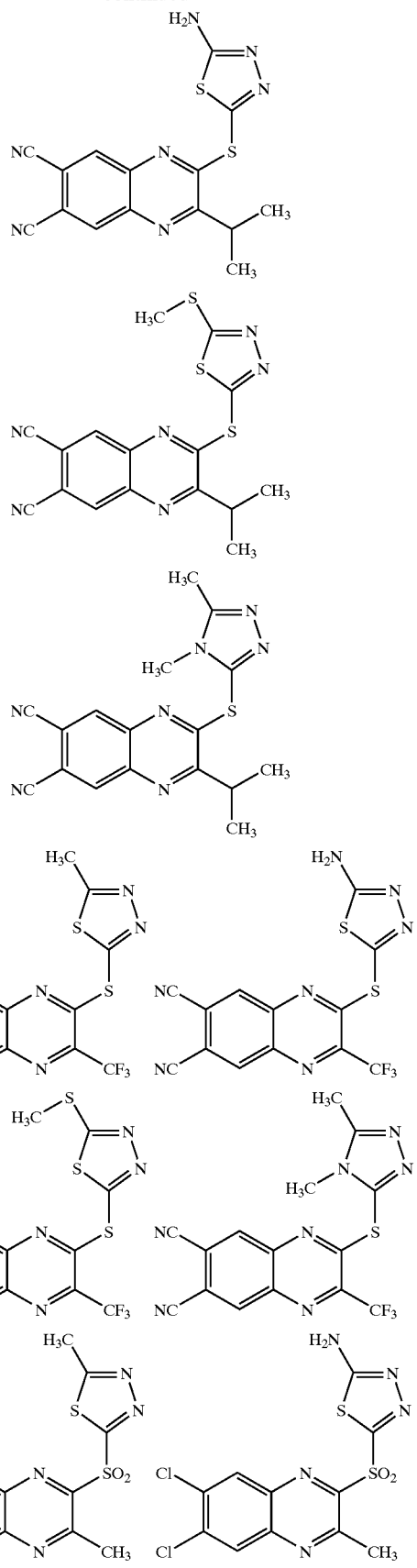

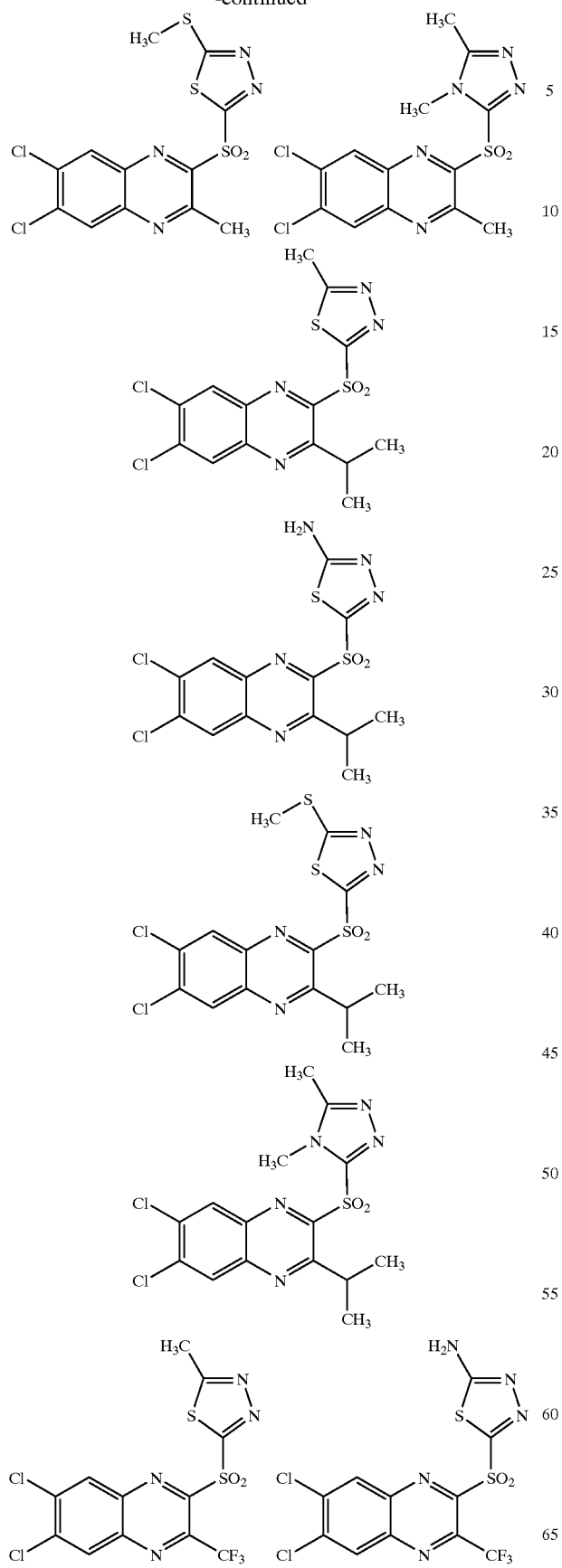
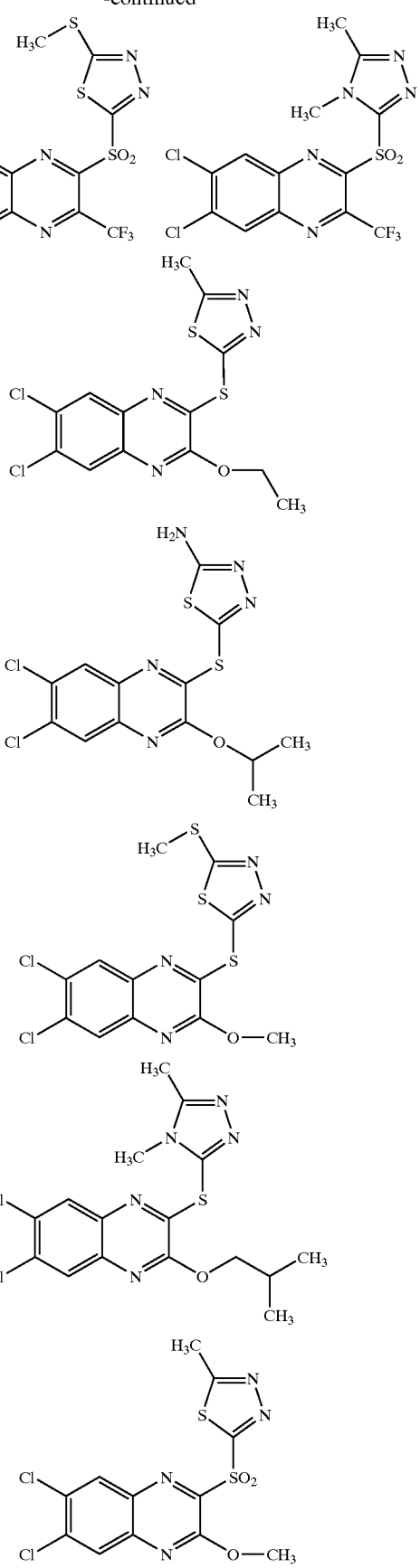

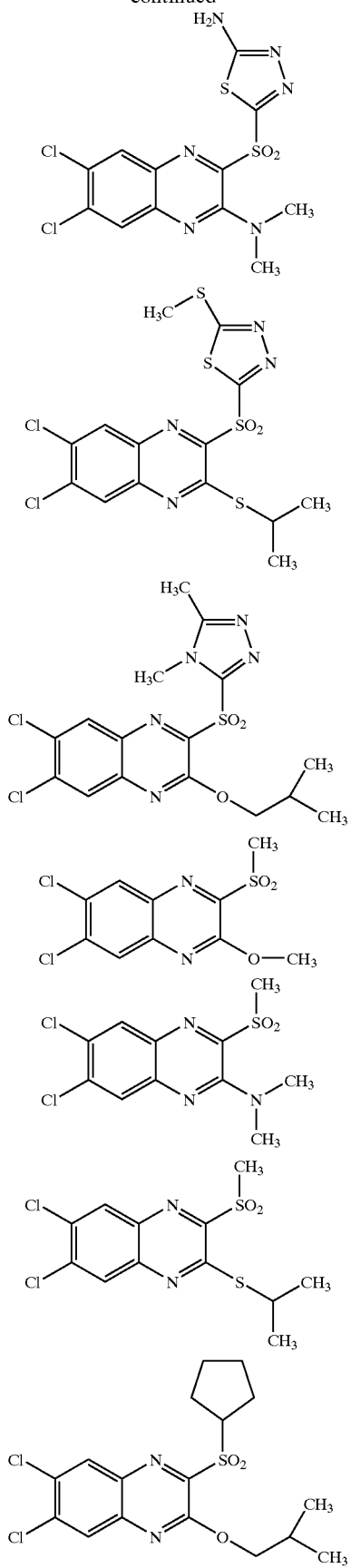
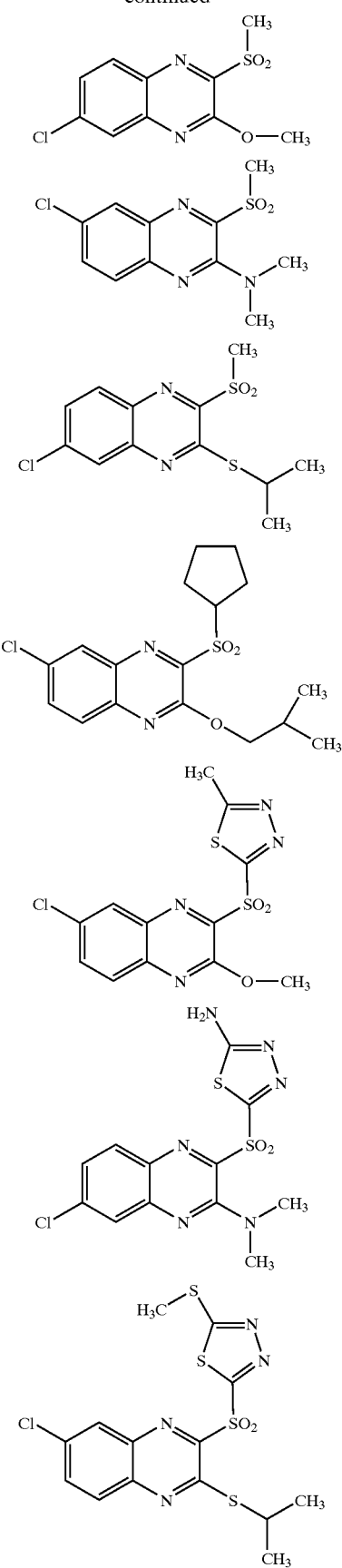

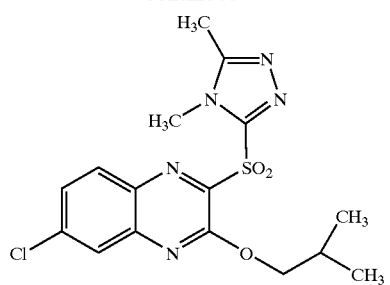
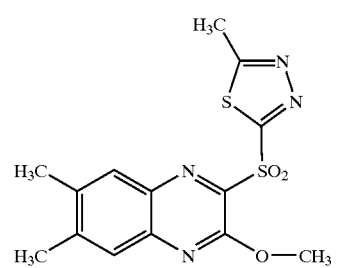
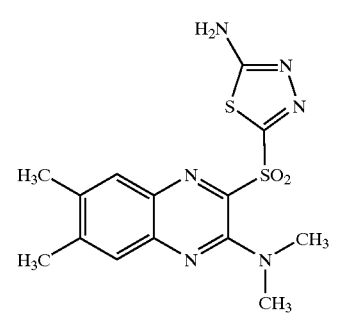
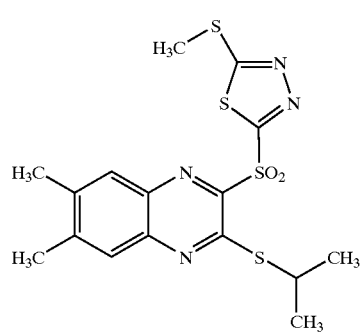
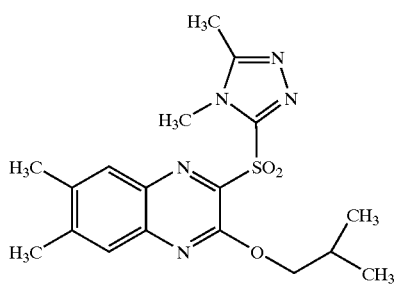
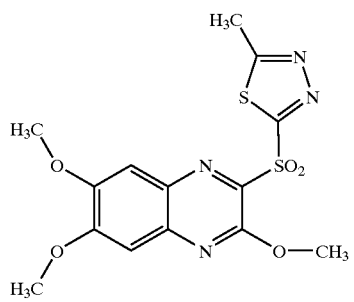
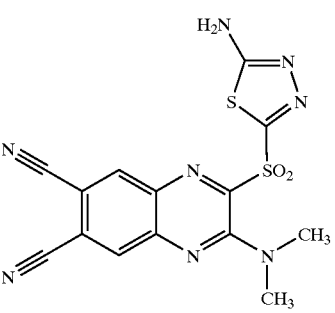
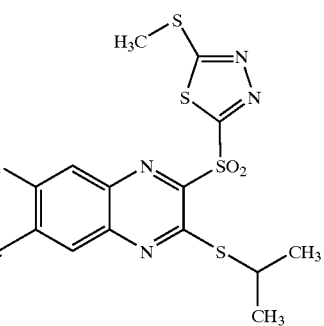
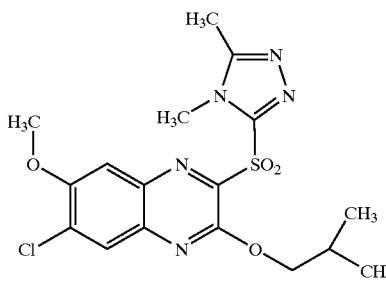
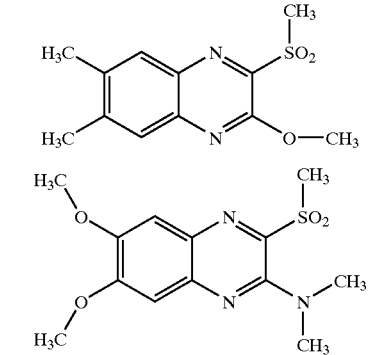

-continued

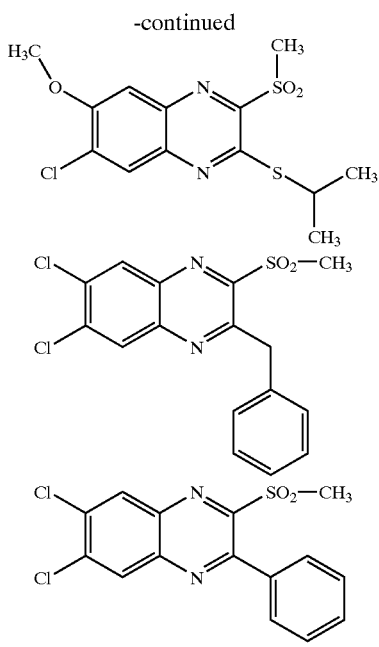

Example 172

Determination of $EC_{50}$

Stimulation of cAMP Formation in a Cell Line Expressing the Cloned Human GLP-1 Receptor In order to demonstrate the efficacy of the GLP-1 agonists, their ability to stimulate formation of cAMP in a cell line expressing the cloned human GLP-1 receptor was tested. The $EC_{50}$ value was calculated from the dose-response curve. Baby hamster kidney (BHK) cells expressing the human pancreatic GLP-1 receptor were used (Knudsen and Pridal, 1996, Eur. J. Pharm. 318, 429–435).

Two different protocols were used:
Method 1:

Plasma membranes were prepared (Adelhorst et al, 1994, J. Biol. Chem. 269, 6275) by homogenisation in buffer (10 mmol/l Tris-HCl and 30 mmol/l NaCl pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk A/S, Bagsvaerd, Denmark)). The homogenate was centrifuged on top of a layer of 41 w/v % sucrose. The white band between the two layers was diluted in buffer and centrifuged. Plasma membranes were stored at −80° C. until use.

The assay was carried out in 96-well microtiter plates in a total volume of 200 μl. The resulting concentration in the assay was 50 mmol/l Tris-HCl, pH 7.4, 1 mmol/l EGTA, 1.5 mmol/l $MgCl_2$, 1.85 mmol/l ATP, 20 μM GTP (guanosine triphosphate), 1 mmol/l 3-isobutyl-1-methylxanthine, 0.01% Tween-20 and 0.1% bovine serum albumin (Reinst, Behringwerke AG, Marburg, Germany). Compounds to be tested for agonist activity were dissolved and diluted in DMSO. GLP-1 was dissolved and diluted in buffer. For GLP-1 test, diluted GLP-1 was added in 35 μl buffer and 10 μl DMSO added extra. For compounds, 10 μl compound in DMSO was added. 1–4 μg plasma membrane in 50 μl buffer was added and the mixture was incubated for 2 hours at 37° C. The reaction was stopped by the addition of 25 μl of 0.5 mol/l HCl. Samples were diluted 5 to 10 fold before analysis for cAMP by a scintillation proximity assay (RPA 538, Amersham, UK). In this assay, GLP-1 was measured with a potency ($EC_{50}$) of 37±23 pM (n=10).

Method 2:

Membranes were prepared as follows. Suspended cells from one 10 layer cell factory were transferred to 250 ml Sorwall tubes (for GSA rotor and centrifuged at 10.000 g for 10 min at 4° C. 100 ml 25 mM Hepes (pH 7.4), 2.5 mM $CaCl_2$, 1 mM $MgCl_2$, 250 mg/l bacitracin, 0.1 mM Pefabloc (homogenizing buffer) were added to the cell pellet which was then homogenised for 2×10 sec. on Ultra-turex (on ice). 100 ml extra homogenising buffer was added and cell nuclei was spun down at 2000 g for 15 min, 4° C. (without brakes). The supernatant containing membranes was transferred to 200 ml tubes (for Sorwall A-621 rotor) and centrifuged at 40.000 g for 45 min at 4° C. The pellet and 100 ml homogenising buffer were homogenised for 2×10 sec. on Ultra-turex (on ice). 100 ml extra homogenising buffer was added and centrifugation continued at 40.000 g for 45 min at 4° C. The membrane pellet was resuspended in 10 ml 25 mM Hepes (pH 7.4), 2.5 mM $CaCl_2$, 1 mM $MgCl_2$ using Ultra-turex 2×10 sec. (on ice). After protein determination 10 v/v % 25 mM Hepes (pH 7.4), 2.5 mM $CaCl_2$, 1 mM $MgCl_2$, 1% BSA, 0.5 mg/ml bacitracin, 2.5 M sucrose was added. The membranes were stored at −80° C. until use.

The assay was carried out in 96-well microtiter plates in a total volume of 200 μl. To 195 μl (50 mmol/l Tris-HCl, pH 7.4, 1 mmol/l EGTA, 1.5 mmol/l $MgCl_2$, 1.85 mmol/l ATP, 20 μM GTP, 1 mmol/l 3-isobutyl-1-methylxanthine and 0.1% bovine serum albumin (Reinst, Behringwerke AG, Marburg, Germany)), 32 μg plasma membrane protein was added. Compounds to be tested for agonist activity were dissolved and diluted in DMSO. GLP-1 was dissolved and diluted in 0.2% Tween-20. For GLP-1 test, diluted GLP-1 was added in 5 μl 0.2% Tween-20 and 5 μl DMSO added extra. For compounds, 5 μl in DMSO was added and 5 μl 0.2% Tween-20 added extra. The mixture was incubated for 2 hours at 37° C. The reaction was stopped by the addition of 50 μl of 0.5 mol/l HCl. Samples were diluted 5 to 10 fold before analysis for cAMP by a scintillation proximity assay (RPA 538, Amersham, UK). In this assay, GLP-1 was measured with a potency ($EC_{50}$) of 400±200 pM (n=10).

In the following Table the results are given for a representative selection of the present compounds:

| Compound, Example No | $EC_{50}$ (nM) | $E_{max}$ (%) |
|---|---|---|
| 6 | 170* | 94 |
| 7 | 78 *(KHP21298) | 120 |
| 19 | 160 *(KHP21698) | 120 |
| 20 | 68* | 140 |
| 25 | * | 15 at 33.000 nM |
| 29 | * | 13 at 33.000 nM |
| 56 | 78* | 130 |
| 46 | *>33.000 | 0 |
| 47 | 10.000* | 50 |
| 2 | 310* | 100 |
| 65 | 650** | 53 |
| 92 | 770** | 53 |
| 103 | 50** | 80 |
| 137 | 660*** | 46 |
| 138 | 540*** | 72 |
| 135 | 290*** | 76 |
| 136 | 820*** | 64 |
| 108 | 680*** | 54 |
| 169 | ** | 19 at 1000 nM |
| 171 | ** | 27 at 33000 nM |

-continued

| Compound, Example No | EC$_{50}$ (nM) | E$_{max}$ (%) |
|---|---|---|
| 170 | ** | 33 at 1000 nM |
| 156 | ** | 42 at 10.000 nM |
| 147 | ** | 31 at 1000 nM |
| 145 | ** | 36 at 330 nM |
| 157 | ** | 15 at 3300 nM |

EC$_{50}$ was calculated in relation to the GLP-1 curve. EC$_{50}$ for the compound is thus defined as the concentration of compound giving the same response as the EC$_{50}$ for GLP-1.
*Method 1, one representative experiment
**Method 2, one representative experiment
***Method 2, average of two experiments

Example 173

Competition Binding Assay, Compounds do not Compete with $^{125}$I-GLP-1

Plasma membranes were prepared from BHK cells. Binding assays were carried out in poly-propylene tubes. The buffer was 25 mM HEPES, 0.1% BSA, pH 7.4. GLP-1 and test compounds were dissolved and diluted as described in 172. Tracer (labelled GLP-1) was prepared as described in (28). Test compound+tracer (30.000 cpm)+plasma membranes (0.5–2 μg) were mixed and tubes incubated at 37° C. for 1 hour. Non-specific binding was determined with 10$^{-7}$ M GLP-1. Bound and unbound tracer were separated by vacuum filtration. The filters were counted in a γ-scintillation counter. The binding of the tracer in the absence of the test compounds and GLP-1 was set to 100%. A compound which does not compete with GLP-1 in a competition binding assay will not displace the tracer. Therefore, the tracer will display an unchanged binding of 100% in this assay whereas different concentrations of GLP-1 will compete with the tracer resulting in a decreased binding of the tracer in the range of between 0 and up to 100%.

Example 174

Competition Binding Assay, Compounds Potentiate Binding of $^{125}$I-GLP-1

Plasma membranes were prepared as in example 172. Binding assays were carried out in polypropylene tubes. The buffer was 25 mM HEPES, 0.1% BSA, pH 7.4. GLP-1 and test compounds were dissolved and diluted as described in example 172. Tracer (labelled GLP-1) was prepared as described in (28). Test compound+tracer (30.000 cpm)+plasma membrane (0.5–2 μg) were mixed and tubes incubated at 370° C. for 1 hour. Non-specific binding was determined with 10$^{-7}$ M GLP-1. Bound and unbound tracer were separated by vacuum filtration. The filters were counted in a γ-scintillation counter. The binding of the tracer in the absence of the test compounds and GLP-1 was set to 100%. A compound which does not compete with GLP-1 in a competition binding assay will not displace the tracer. Therefore, the tracer will display an unchanged binding of 100% in this assay whereas compounds of this invention that potentiate GLP-1 binding result in binding of the tracer in the range above 100% to 300% or above.

Example 175

Saturation Experiments, Compounds Stabilize Another Conformation of the Receptor than that GLP-1 Stabilize Physiologically Plasma membranes were prepared as in example 172. Binding assays were carried out in filter microtiter plates (MADV N65, Millipore). The buffer was 50 mM HEPES, 5 mM EGTA, 5 mM MgCl$_2$, 0.005% Tween 20, pH 7.4. GLP-1 and test compounds was dissolved and diluted as described in example 172. Tracer (labelled GLP-1) was prepared as described in (28) and diluted in buffer. 165 μl buffer+10 μl DMSO with or without 10 μM 6,7-dichloro-2-trifluoromethyl-3-(5-methyl-1,3,4-thiadiazol-2-ylsulfanyl) quinoxaline (example 2)+25 μl of different dilutions of tracer+25 μl plasma membrane (0.5–2 μg) was mixed and plates incubated at 25° C. for 2 hours. Non-specific binding was determined with 10$^{-6}$ M GLP-1. Bound and unbound tracer were separated by vacuum filtration (Millipore vacuum manifold). The plates were washed once with 150 μl buffer/well, and air dried for a couple of hours, whereupon filters were separated from the plates using a Millipore Puncher. The filters were counted in a γ-scintillation counter. The specific binding (total minus non-specific) was then plotted vs the concentration of tracer added. A curve fitting program (eg the saturation/scatchard template in GraphPad Prism®) then determined the number of binding sites and the affinity. There may be more than one binding site with different affinities. When such an experiment is performed with GLP-1 one may observe one or two different binding sites dependent on the temperature at which the experiment is performed.

A saturation plot for GLP-1 in the absence of 6,7-dichloro-2-trifluoromethyl-3-(5-methyl-1,3,4-thiadiazol-2-ylsulfanyl)-quinoxaline (example 2) at 30° C. resulted in the following result:

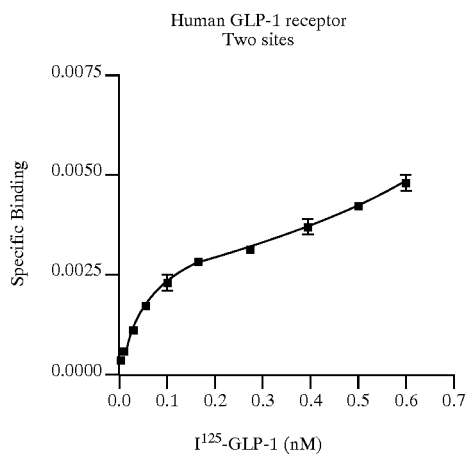

The data were equivalent with two binding sites: one had a K$_d$ of 790 pM and a B$_{max}$ of 6.5 pM. The other a K$_d$ of 26 pM and a B$_{max}$ of 2.0 pM.

Also the Scatchard plot clearly shows the presence of two binding sites as one straight line can not be fitted through the data points.

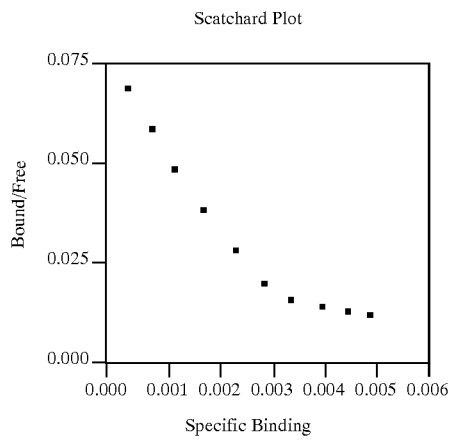

Scatchard Plot

A saturation plot for GLP-1 in the presence of 6,7-dichloro-2-trifluoromethyl-3-(5-methyl-1,3,4-thiadiazol-2-ylsulfanyl)-quinoxaline (example 2) at 30° C. resulted in the following:

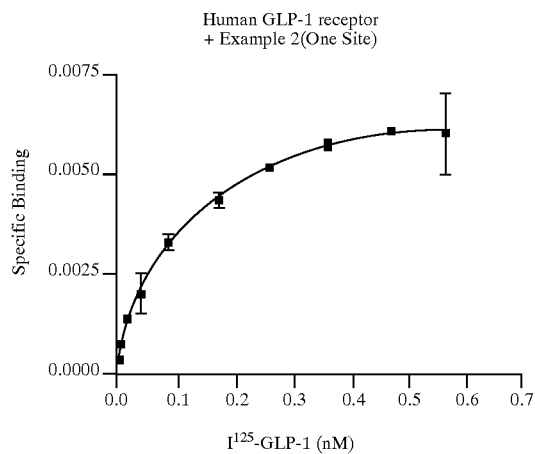

These data were in agreement with one binding site, $K_d$ 120 pM and $B_{max}$ of 7.5 pM. Also, the Scatchard plot clearly show that in the presence of 6,7-dichloro-2-trifluoromethyl-3-(5-methyl-1,3,4-thiadiazol-2-ylsulfanyl)quinoxaline (example 2) there is now only one class of binding sites with affinity for GLP-1. And this binding site is characterized by having a affinity for GLP-1 between the high and low existing in the absence of 6,7-dichloro-2-trifluoromethyl-3-(5-methyl-1,3,4-thiadiazol-2-ylsulfanyl)quinoxaline (example 2). 6,7-dichloro-2-trifluoro-methyl-3-(5-methyl-1,3,4-thiadiazol-2-ylsulfanyl)quinoxaline (example 2) has then changed the affinity of the receptor for GLP-1 meaning that the conformation of the receptor must be different otherwise it would not have a changed affinity for GLP-1. Example 172 shows that the conformation that 6,7-dichloro-2-trifluoromethyl-3-(5-methyl-1,3,4-thiadiazol-2-ylsulfanyl)-quinoxaline (example 2) stabilises must be an active conformation otherwise 6,7-dichloro-2-trifluoromethyl-3-(5-methyl-1,3,4-thiadiazol-2-ylsulfanyl) quinoxaline (example 2) would not be an agonist.

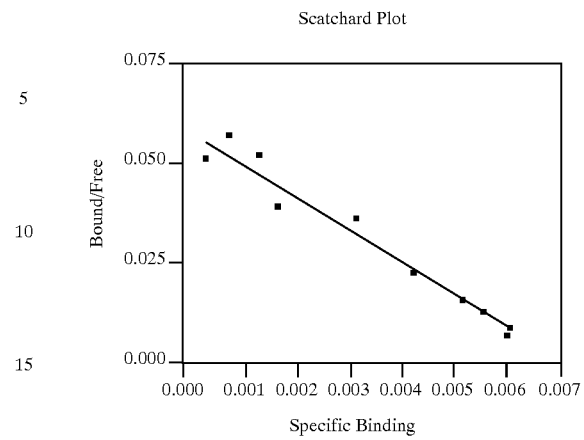

Scatchard Plot

Example 176

Stimulation of cAMP Formation in a Cell Line Expressing the Cloned Human Glucagon Receptor, Compounds Selective for the GLP-1 Receptor The procedure in example 172 was followed except a cell line using the human glucagon receptor was used (P. Madsen, L. B. Knudsen, F. C. Wiberg and R. D. Carr, Discovery and SAR of the first non-peptide competitive glucagon receptor antagonist. *J. Med. Chem*, 41 (1998), 5150–57.)

In this assay glucagon was measured with an $EC_{50}$ of 8.4 pM. 6,7-dichloro-2-trifluoromethyl-3-(5-methyl-1,3,4-thiadiazol-2-ylsulfanyl)quinoxaline (example 2) had no measurable activity. Concentrations tested was up to 100 $\mu$M.

From the foregoing, it will be appreciated that, although specific embodiments of the invention have been described herein for the purposes of illustration, various modifications may be made without deviating from the spirit and scope of the invention as defined by the appended claims.

REFERENCES

1. Holst J J. Annual Review of Physiology 1997;59:257–271.
2. Nauck M A, Heimesaat M M, Ørskov C, Holst J J, Ebert R, Creutzfeldt W. Preserved incretin activity of GLP-1(7-36amide) but not of synthetic human GIP in patients with type 2-diabetes mellitus. J. Clin. Invest. 1993;91:301–307.
3. Willms B, Werner J, Holst J J, Ørskov C, Creutzfeldt W, Nauck M. Gastric emptying, glucose responses, and insulin secretion after a liquid test meal: effects of exogenous GLP-1(7-36)amide in type 2 (noninsulin-dependent) diabetic patients. J. Clin. Endocrinol. Metab. 1996;81:327–332.
4. Qualmann C, Nauck M, Holst J J, Ørskov C, Creutzfeldt W. Insulinotropic actions of intravenous glucagon-like peptide-1 [7-36 amide] in the fasting state in healthy subjects. Acta Diabetologica, 1995;32:13–16.
5. Nathan D M, Schreiber E, Fogel H, Mojsov S, Habener J F. Insulinotropic action of GLP-1-87-37) in diabetic and non-diabetic subjects. Diabetes care 1992;15:270–276.
6. Nauck M A, Kleine N, Ørskov C, Holst J J, Willms B, Creutzfeldt W. Normalization of fasting hyperglycemia by exogenous GLP-1 (7-36amide) in type 2-diabetic patients. Diabetologia 1993;36:741–744.

7. Kreymann B, Ghatai M A, Williams G, Bloom S R. GLP-1 7-36: a physiological incretin in man. Lancet 1987;II:1300–1304.
8. Rachman J, Barrow B A, Levy J C, Turner R C. Near-normalization of diurnal glucose concentrations by continous administration of GLP-1 in subjects with NIDDM. Diabetologia 1997;40(2):205–211.
9. Gutniak M K, Linde B, Holst J J, Efendic S. Subcutaneous injection of the incretin hormone GLP-1 abolishes postprandial glycemia in NIDDM. Diabetes Care 1994;17(9): 10391044.
10. Nauck M A, Wollschläger D, Werner J, Holst J J, Ørskov C, Creutzfeldt W, Willms B. Effects of subcutaneous GLP-1 (7-36)amide in patients with NIDDM. Diabetologia 1996;39:1546–1553.
11. Creutzfeldt W, Kleine N, Willms B, Ørskov C, Holst J J, Nauck M A. Glucagonostatic actions and reduction of fasting hyperglycemia by exogenous glucagon-liem, peptide-1(7-36amide) in type I diabetic patients. Diabetes Care 1996;19:580–586.
12. Fehmann, H. C. and Habener, J. F. Insulinotropic hormone GLP-1-(7-37) stimulation of proinsulin gene expression and proinsulin biosynthesis in insulinoma βTC1-cells. Endocrinology 1992;130:159–66.
13. Wang, Y., Egan, J. M., Raygada, M., Nadiv, O., Roth, J. and Montrose-Rafizadeh, M. GLP-1 affects gene transcription and mRNA stability of components of the insulin secretory system in RIN 1046–38 cells. Endocronology 1995;136:4910–4917.
14. Wang, Y., Perfetti, R., Greig, N., Holloway, H. W., DeOre K. A., Montrose-Rafizadeh, M., Elahi, D. and Egan, J. M. GLP-1 can reverse the age-related decline in glucose tolerance in rats. J. Clin. Invest. 1997;99:2883–2889.
15. Edvell, A., Lindström, P. Initiation of increased pancreatic islet growth in young normoglycaemic mice (Umeå +/?). Endocrinology 1999;140(2):778–783.
16. Buteau, J., Roduit, R., Susini, S., Prentki, M. GLP-1 promotes DNA synthesis, activates phosphatidylinositol-3-kinase and increases transcription factor pancreatic and duodenal homeobox gene 1 (PDX-1) DNA binding activity in beta (INS-1)-cells. Diabetologia 1999;42(7): 856–864.
17. Gang, X., Stoffers, D. A., Habener, J. F., Bonner-Weir, S. Exendin-4 stimulates both beta-cell replication and neogenesis, resulting in increased beta-cell mass and improved glucose tolerance in diabetic rats. Diabetes 1999;48:2270–2276.
18. Nauck M, Stöckmann R, Ebert R, Creutzfeldt W: Reduced incretin effect in type-2 (non-insulin-dependent) diabetes. *Diabetologia* 29: 46–52, 1986.
19. Hoist J J, Gromada J, Nauck M A: The pathogenesis of non-insulin dependent diabetes mellitus involves a defective expression of the GIP receptor. *Diabetologia* 40: 984–986, 1997.
20. Nauck M A, Heimesaat M M, Ørskov C, Hoist J J, Ebert R, Creutzfeldt W: Preserved incretin activity of GLP-1 (7-36amide) but not of synthetic human GIP in patients with type 2-diabetes mellitus. *J Clin Invest* 36: 741–744, 1993.
21. Nauck M A, Heimesaat M M, Ørskov C, Hoist J J, Ebert R, Creutzfeldt W. Preserved incretin activity of GLP-1 (7-36amide) but not of synthetic human GIP in patients with type 2-diabetes mellitus. J. Clin. Invest. 1993;91:301–307.
22. Flint, A., Raben, A., Astrup, A., Hoist, J. J. GLP-1 promotes satiety and suppresses energy intake in humans. J. Clin. Invest. 1998;101:515–520.
23. Näslund, E., Gutniak, M. K., Skogar, S., Rössner, S. and Hellström, P. M. GLp-1 increases the period of postprandial satiety and slows gastric emptying in obese humans. Am. J. Clin. Nutr. 1998 in press.
24. Näslund, E. and Hellström, P. M. GLP-1 in the pathogenesis of obesity. Drug News Perspect. 1998;11(2): 92–97.
25. Ranganath, L. R., Beethy, J. M., Moragn, L. M., Wright, J. M., Howland, R. and Marks, V. Attenuated GLP-1 secretion in obesity: cause or consequence. Gut 1996;38:916–919.
26. Näslund, E., Gryback, P., Backman, L., Jacobsson, H., Hoist, J. J., Theodorsson, E. and Hellström, P. M. Small bowel gut hormones: correlation to fasting antroduodenal motility and gastric emptying. Dig. Dis. Sci. 1998 in press.
27. Deacon, C. F., M. A. Nauck, M. Toft-Nielsen, L. Pridal, B. Willms and J. J. Hoist, Both subcutaneous and intravenously administered GLP-1 are rapidly degraded from the N-terminus in type-2 diabetic patients and in healthy subjects, Diabetes 1995; 44: 1126.
28. Knudsen, L. B., and Pridal, I., GLP-1(9-36)amide is a major metabolite of GLP-1(7–36)amide after in vivo administration to dogs and it acts as an antagonist on the pancreatic receptor. Eur. J. Pharm. 1996; 318: 429–435.
29. Horn, F., Bywater, R., Krause, G., Kuipers, W., Oliveira, L., Paiva, A. C. M., Sander, C. and Vriend, G., The interaction of class B G Protein-Coupled receptors with their hormones. Receptors and Channels 1998; 5: 305–314.
30. Adelhorst, K., Heedegaard, B. B., Knudsen, L. B. and Kirk, O., Structure activity studies of GLP-1, J. Biol. Chem. 1994; 269(9): 6275–6279.
31. Gether, U. and Kobilka, B. K, G protein-coupled receptors. II. Mechanism of agonist activation. J. Biol. Chem. 1998; 273(29): 17979–17982.
32. Hulme, E. C., Receptor-Ligand interactions, A practical approach. IRL Press 1992: 86–89.

We claim:
1. A compound of formula (I);

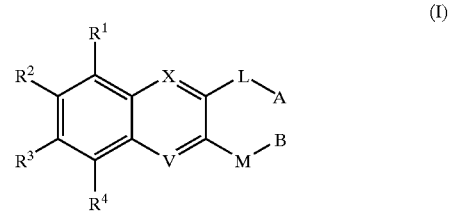

wherein
$R^1$, $R^2$, $R^3$ and $R^4$ independently are hydrogen, halogen, —$CF_3$ or —$NO_2$, X and V are =N—,
L is —$SO_2$—$CH_2$—,
M is —$NR^9$—$CH_2$, —$SO_2$-alkylene, —S-alkylene, —SO-alkylene, —NH—, —$NH_2$ or a valence bond,
wherein $R^9$ is hydrogen, lower allyl, cycloalkyl or a heteroaryl which is a 3 to 10 membered ring containing one or more heteroatoms selected from nitrogen, oxygen and sulfur,
in which the cycloalkyl and heteroaryl rings may optionally be substituted with one or more substituents independently selected from halogen, lower alkyl, lower alkanoyl, —OH, —$CH_2OH$, —$NO_2$, —CN, —C(O)OH, —O-lower alkyl, —C(O)$OCH_3$, —C(O)$NH_2$, —$OCH_2C(O)NH_2$, —$NH_2$, —N$(CH_3)_2$, —CH$(CH_3)_2$, —$SO_2NH_2$, —$OCHF_2$, —$CF_3$ and —$OCF_3$, as well as any optical or geometric isomer or mixture of optical or geometric isomers, or any tautomeric form thereof or a pharmaceutically acceptable salt thereof.

2. A compound of formula (V):

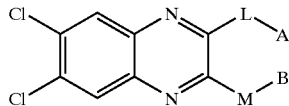

(V)

wherein

L is —SO₂—CH₂—, —S—, or —SH,

M is —NR⁹—CH₂, —SO₂-alkylene, —S-alkylene, —SO-alkylene, —NH—, —NH₂ or a valence bond, wherein R⁹ is hydrogen, lower alkyl, cycloalkyl or a heteroaryl which is a 3 to 10 membered ring containing one or more heteroatoms selected from nitrogen, oxygen and sulfur, in which the cycloalkyl and heteroaryl rings may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂—OCH₂C(O)NH₂, —NH₂, —N(CH₃)₂, —CH₂N(CH₃)₂, —SO₂NH₂, —OCHF₂, —CF₃ and —OCF₃, A and B independently are hydrogen or lower alkyl, as well as any optical or geometric isomer or mixture of optical or geometric isomers ar any tautomeric form thereof or a pharmaceutical acceptable salt thereof.

3. A pharmaceutical composition comprising a compound according to claim 1 together with a pharmaceutically acceptable carrier or excipient.

4. A pharmaceutical composition according to claim 3 in unit dosage form, said composition comprising from about 0.05 mg to about 1000 mg of the compound.

5. A method for the treatment of disorders or diseases wherein an activation of the human GLP-1 receptor is beneficial, said method comprising administering to a subject in need thereof an effective amount of a compound of formula (I):

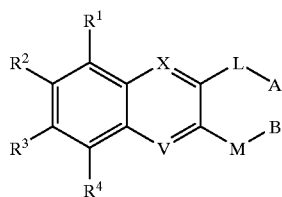

(I)

wherein

R¹, R², R³ and R⁴ independently are hydrogen, halogen, —CF₃ or —NO₂,

X and V are =N—,

L is —SO₂—CH₂—, —S—, —SH, —NH₂ or —NH—,

M is —NR⁹—CH₂, —SO₂-alkylene, —S-alkylene, —SO-alkylene, —NH—, —NH₂ or a valence bond, wherein R⁹ is hydrogen, lower alkyl, cycloalkyl or a heteroaryl which is a 3 to 10 membered ring containing one or more heteroatoms selected from nitrogen, oxygen and sulfur, in which the cycloalkyl and heteroaryl rings may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₃, —OCHF₂, —CF₃ and —OCF₃, A and B independently are hydrogen or lower alkyl, as well as any optical or geometric isomer or mixture of optical or geometric isomers, or any tautomeric form thereof or a pharmaceutically acceptable salt thereof.

6. The method according to claim 5 wherein the effective amount of the compound is in the range of from about 0.05 mg to about 2000 mg per day.

7. A pharmaceutical composition according to claim 3 in unit dosage form, said composition comprising from about 0.1 mg to about 500 mg of the compound.

8. A pharmaceutical composition according to claim 3 in unit dosage form, said composition comprising from about 0.5 mg to about 200 mg of the compound.

9. The method according to claim 5 wherein the effective amount of the compound is in the range of from about 0.1 mg to about 1000 mg per day.

10. The method according to claim 5 wherein the effective amount of the compound is in the range of from about 0.5 mg to about 500 mg per day.

11. A pharmaceutical composition comprising a compound according to claim 2 together with a pharmaceutically acceptable carrier or excipient.

12. A pharmaceutical composition according to claim 11 in unit dosage form, said composition comprising from about 0.05 mg to about 1000 mg of the compound.

13. A pharmaceutical composition according to claim 11 in unit dosage form, said composition comprising from about 0.1 mg to about 500 mg of the compound.

14. A pharmaceutical composition according to claim 11 in unit dosage form, said composition comprising from about 0.5 mg to about 200 mg of the compound.

15. A method for the treatment of disorders or diseases wherein an activation of the human GLP-1 receptor is beneficial, said method comprising administering to a subject in need thereof an effective amount of a compound of formula (V):

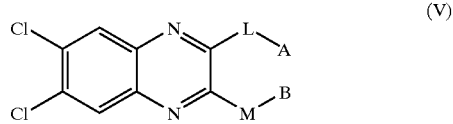

(V)

L is —SO₂—CH₂—, —S—, —SH, —NH₂ or —NH—,

M is —NR⁹—CH₂, —SO₂-alkylene, —S-alkylene, —SO-alkylene, —NH—, —NH₂ or a valence bond, wherein R⁹ is hydrogen, lower alkyl, cycloalkyl or a heteroaryl which is a 3 to 10 membered ring containing one or more heteroatoms selected from nitrogen, oxygen and sulfur, in which the cycloalkyl and heteroaryl rings may optionally be substituted with one or more substituents independently selected from halogen, lower alkyl, lower alkanoyl, —OH, —CH₂OH, —NO₂, —CN, —C(O)OH, —O-lower alkyl, —C(O)OCH₃, —C(O)NH₂, —OCH₂C(O)NH₂, —NH₂, —N(CH₃)₂, —CH₂N(CH₃)₂, —SO₂NH₃, —OCHF₂, —CF₃ and —OCF₃, A and B independently are hydrogen or lower alkyl, as well as any optical or geometric isomer or mixture of optical or geometric isomers, or any tautomeric form thereof or a pharmaceutically acceptable salt thereof.

16. The method according to claim 15 wherein the effective amount of the compound is in the range of from about 0.05 mg to about 2000 mg per day.

17. The nod according to claim 15 wherein the effective amount of the compound is in the range of from about 0.1 mg to about 1000 mg per day.

18. The method according to claim 15 wherein the effective amount of the compound is in the range of from about 0.5 mg to about 500 mg per day.

19. A compound selected from the group consisting of
6,7-Dichloro-3-methyl-2-(methylsulfonyl)quinoxaline,
(6,7-Dichloro-3-methylsulfonylquinoxalin-2-yl)amine,
6,7-Dichloro-2-methylsulfonyl-3-(methylsulfonyl)methyl-quinoxaline,
6,7-Dichloro-2-isopropyl-3-(isopropyl-2-sulfonyl) quinoxaline,
6,7-Dichloro-2-isopropyl-3-(methylsulfonyl)quinoxaline,
6,7-Dichloro-2-(isopropylsulfonyl)-3-[(isopropylsulfonyl)methyl]quinoxaline,
6,7-Dichloro-2-isobutyl-3-(methylsulfonyl)quinoxaline,
2-(Sec-butyl)-6,7-dichloro-3-(methylsulfonyl)quinoxaline,
N-[6,7-Dichloro-3-methylsulfonyl)-2-quinoxalinyl]-N-isopropylamine,
N-(6,7-Dichloro-3-(methylsulfonyl)-2-quinoxalinyl)-N-methyl-N-isopropylamine,
N-(6,7-Dichloro-3-(methylsulfonyl)-2-quinoxalinyl)-ethylamine,
N-(6,7-Dichloro-3-(methylsulfonyl)-2-quinoxalinyl)-N,N-dimethylamine,
6,7-Dichloro-3-ethyl-2-(methylsulfonyl)quinoxaline,
6,7-Dichloro-2-(methylsulfonyl)-3-hexylquinoxaline,
6,7-Dichloro-2-(methylsulfonyl)-3-propylquinoxaline,
6,7-Dichloro-2-(isopropylsulfonyl)-3-propylquinoxaline,
N-[6,7-Dichloro-3-(methylsulfonyl)-2-quinoxalinyl]-N-tert-butylamine,
N-[6,7-Dichloro-3-methylsulfonyl)-2-quinoxalinyl]-N-isobutylamine,
5,6,7,8-Tetrachloro-2-isopropyl-3-(methylsulfonyl) quinoxaline,
(6,7-Dichloro-3-methylsulfonylquinoxalin-2-yl) cyclopropylamine,
(6,7-Dichloro-3-methylsulfonylquinoxalin-2-yl) cyclopentylamine,
(6,7-Dichloro-3-methylsulfonylquinoxalin-2-yl)sec-butylamine,
(6,7-Dichloro-)-3-(methylsulfonylquinoxalin-2-yl)-1-ethylpropylamine;
(7-Chloro-3-(methylsulfonyl)-6-nitroquinoxalin-2-yl)sec-butylamine,
(6-Chloro-3-methylsulfonyl-7-nitro-8-trifluoromethylquinoxalin-2-yl)isopropylamine,
(6,7-Dichloro-3-(methylsulfonyl)-quinoxalin-2-yl)tert-pentylamine,
6,7-Dichloro-2-(isopropylsulfanyl)-3-(methylsulfonyl) quinoxaline,
(5-Chloro-3-methylsulfonyl-7-trifluoromethyl-2-quinoxalin-2-yl)-tert-butylamine,
(3-Methylsulfonyl-6,7-dinitroquinoxalin-2-yl)-tert-butylamine,
6-Chloro-2-(3-methylbutylsulfonyl)quinoxaline,
(6,7-Dichloro-3-methanesulfonylquinoxalin-2-yl)-[2-(2,4-dichlorophenyl)ethyl]amine,
(6,7-Dichloro-3-methanesulfonylquinoxalin-2-yl)-[2-(3-fluorophenyl)ethyl]amine,
3-[2-(6,7-Dichloro-3-methanesulfonyl-quinoxalin-2-ylamino)ethyl]phenol,
(6,7-Dichloro-3-methanesulfonylquinoxalin-2-yl)-[2-(3-fluorophenyl)ethyl]amine,
(6,7-Dichloro-3-methanesulfonylquinoxalin-2-yl) dimethylamine,
6,7-Dichloro-2-isopropylsulfanyl-3-methanesulfonylquinoxaline,
(6-Chloro-3-methanesulfonylquinoxalin-2-yl) dimethylamine,
6,7-Dichloro-3-isopropylsulfanyl-3-methanesulfonylquinoxaline,
(6,7-Dichloro-3-methanesulfonylquinoxalin-2-yl)-[2-(2,4-dichlorophenyl)ethyl]amine,
(6,7-Dichloro-3-methanesulfonylquinoxalin-2-yl)-[2-(2-fluorophenyl)ethyl]amine,
3-[2-(6,7-Dichloro-3-methanesulfonyl-quinoxalin-2-ylamino)ethyl]phenol,
(6,7-Dichloro-3-methanesulfonylquinoxalin-2-yl)-[2-(3-fluorophenyl)ethyl]amine,
(6,7-Dichloro-3-methanesulfonylquinoxalin-2-yl) dimethylamine,
6,7-Dichloro-2-isopropylsulfanyl-3-methanesulfonylquinoxaline,
(6-Chloro-3-methanesulfonylquinoxalin-2-yl) dimethylamine, and
6-Chloro-3-isopropylsulfanyl-2-methanesulfonylquinoxaline
as well as any optical or geometric isomer or mixture of optical or geometric isomers, or any tautomeric form therof or a pharmaceutically acceptable salt thereof.

20. A pharmaceutical composition comprising a compound according to claim 19 together with a pharmaceutically acceptable carrier or excipient.

21. A pharmaceutical composition according to claim 20 in unit dosage form, said composition comprising from about 0.05 mg to about 1000 mg of the compound.

22. A pharmaceutical composition according to claim 20 in unit dosage form, said composition comprising from about 0.1 mg to about 500 mg of the compound.

23. A pharmaceutical composition according to claim 20 in unit dosage form, said composition comprising from about 0.5 mg to about 200 mg of the compound.

24. A method for the treatment of disorders or diseases wherein an activation of the human GLP-1 receptor is beneficial, said method comprising administering to a subject in need thereof an effective amount of a compound of claim 19.

25. The method according to claim 24 wherein the effective amount of the compound is in the range of from about 0.05 mg to about 2000 mg per day.

26. The method according to claim 24 wherein the effective amount of the compound is in the range of from about 0.1 mg to about 1000 mg per day.

27. The method according to claim 24 wherein the effective amount of the compound is in the range of from about 0.5 mg to about 500 mg per day.

* * * * *

UNITED STATES PATENT AND TRADEMARK OFFICE
CERTIFICATE OF CORRECTION

PATENT NO. : 6,927,214 B1 Page 1 of 1
APPLICATION NO. : 09/483504
DATED : August 9, 2005
INVENTOR(S) : Teng et al.

It is certified that error appears in the above-identified patent and that said Letters Patent is hereby corrected as shown below:

Column 134, line 66, Claim 1 – Change "-CH(CH$_3$)$_2$-" to -- -CH$_2$N(CH$_3$)$_2$- --

Column 134, after line 67, Claim 1 – insert "A and B independently are hydrogen or lower alkyl,"

Column 135, line 31, Claim 2 – Change "ar any tautomeric" to --or any tautomeric--

Column 138, line 1, Claim 19 – Change "-2-yl)-[2(3-fluorophenyl)ethy]amine," to -- -2-yl)-[2-(2-fluorophenyl0ethyl]amine,--

Signed and Sealed this

Eighteenth Day of September, 2007

JON W. DUDAS
*Director of the United States Patent and Trademark Office*